United States Patent [19]

Light et al.

[11] 4,126,570
[45] Nov. 21, 1978

[54] PROCESS OF ENHANCING THE AROMA OF A DETERGENT WITH NORBORNANE DERIVATIVES

[75] Inventors: Kenneth K. Light, Long Branch; James M. Sanders, Eatontown; Manfred H. Vock, Locust, all of N.J.; Edward J. Shuster, Brooklyn, N.Y.; Joaquin Vinals, Red Bank, N.J.; William L. Schreiber, Jackson, N.J.; John B. Hall, Rumson, N.J.; Denis E. Hruza, Sr., Bricktown, N.J.; Venkatesh Kamath, Red Bank, N.J.; Braja D. Mookherjee, Holmdel, N.J.; Ching Y. Tseng, Middletown, N.J.; Mark A. Sprecker, Sea Bright, N.J.

[73] Assignee: International Flavors & Fragrances Inc., New York, N.Y.

[21] Appl. No.: 860,139

[22] Filed: Dec. 13, 1977

Related U.S. Application Data

[62] Division of Ser. No. 765,847, Feb. 4, 1977, Pat. No. 4,076,853.

[51] Int. Cl.² .............................................. C11D 3/50
[52] U.S. Cl. .................................. 252/89 R; 252/522; 260/586 G; 426/538; 252/108
[58] Field of Search ............................ 252/89 R, 522; 260/586 G

[56] References Cited
U.S. PATENT DOCUMENTS 4,076,854  2/1978  Light et al. .......................... 252/522

Primary Examiner—Mayer Weinblatt

Attorney, Agent, or Firm—Arthur L. Liberman; Franklin D. Wolffe; Harold Haidt

[57] ABSTRACT

Norbornane derivatives are used in detergents. Specifically,

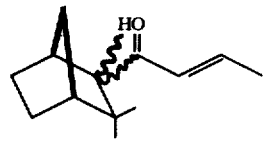

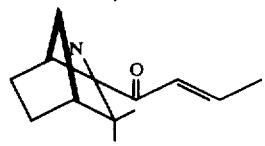

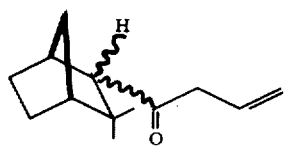

and

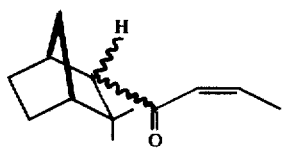

and mixtures of same or a mixture of 2-(2-butenoyl)-3,3-dimethylnorbornane; 2-(3-butenoyl)-3,3-dimethylnorbornane; 2-(2-butenoyl)-3,3-dimethylnorbornane and alpha-allyl-3,3-dimethyl-2-norbornanemethanol are used.

6 Claims, 60 Drawing Figures

NMR SPECTRUM FOR EXAMPLE II.

SOLVENT: $CDCl_3$
SWEEP WIDTH: 1000 cps

IR SPECTRUM FOR EXAMPLE II

NMR SPECTRUM FOR EXAMPLE III: CIS ISOMER

IR SPECTRUM FOR "CIS" ISOMER, ACCORDING TO EXAMPLE III

NMR SPECTRUM FOR EXAMPLE III: ALLYLIC ISOMER.

IR SPECTRUM FOR ALLYLIC ISOMER, ACCORDING TO EXAMPLE III

NMR SPECTRUM FOR EXAMPLE XI: ENDO ISOMER

IR SPECTRUM "ENDO ISOMER" FOR EXAMPLE XI

NMR SPECTRUM FOR EXAMPLE XII, FRACTION 7

Solvent: $CDCL_3$
Sweep Width: 1000 cps.

IR SPECTRUM FOR EXAMPLE XII, FRACTION 7

FIG. II
NMR SPECTRUM FOR EXAMPLE XVII.
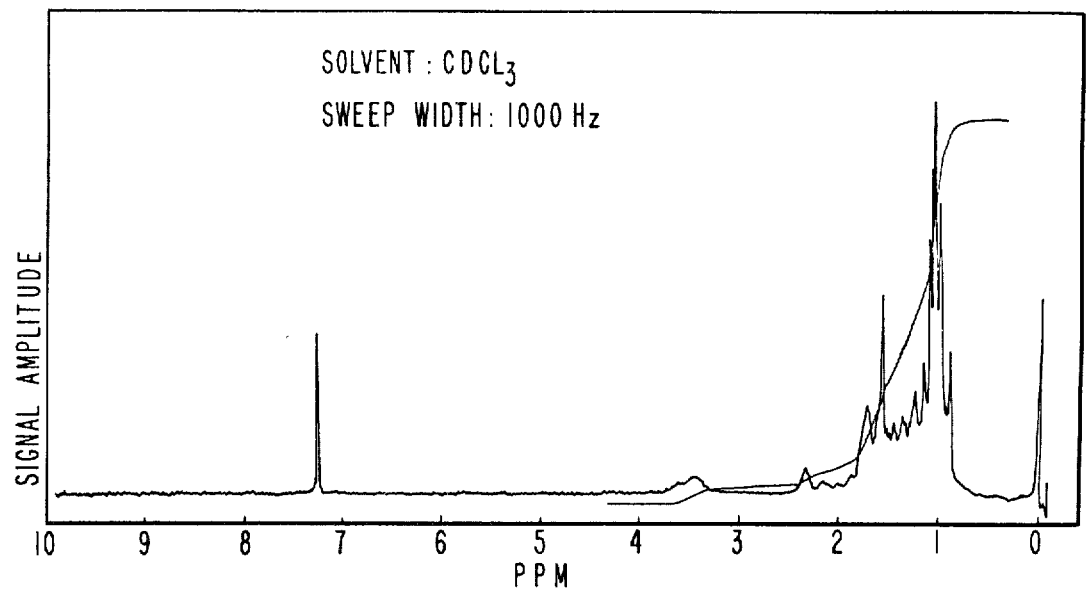
FIG. 12
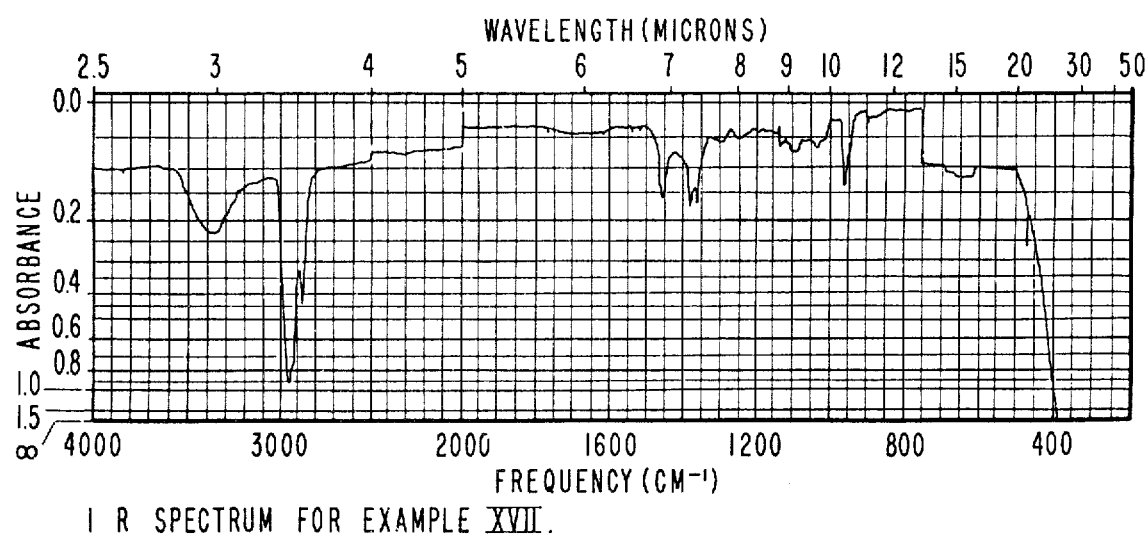
IR SPECTRUM FOR EXAMPLE XVII.

NMR SPECTRUM FOR EXAMPLE XIX

IR SPECTRUM FOR FRACTION 5 OF EXAMPLE XIX

GLC PROFILE FOR EXAMPLE XX

NMR SPECTRUM: ACCORDING TO EXAMPLE XX

IR SPECTRUM: ACCORDING TO EXAMPLE XX

NMR SPECTRUM FOR EXAMPLE XX.

IR SPECTRUM FOR EXAMPLE XX

GLC PROFILE FOR EXAMPLE XXI

NMR SPECTRUM FOR EXAMPLE XXI
(MIXTURE OF 2 KETONES AND KETO-ETHER)

IR SPECTRUM FOR EXAMPLE XXI

NMR SPECTRUM FOR EXAMPLE XXII, FRACTION 4

IR SPECTRUM FOR EXAMPLE XXII

NMR SPECTRUM FOR EXAMPLE XXII, FRACTION 2, PART A.

SOLVENT: $CDCl_3$
SWEEP WIDTH: 1000 CPS.

IR SPECTRUM FOR EXAMPLE XXII, FRACTION 2, PART B.

NMR SPECTRUM FOR EXAMPLE XXIII, FRACTION 4.

SOLVENT: $CDCl_3$
SWEEP WIDTH: 1500 Hz.

IR SPECTRUM FOR EXAMPLE XXIII, FRACTION 4, PART B.

GLC PROFILE FOR EXAMPLE XXIV

NMR SPECTRUM FOR EXAMPLE XXIV

SOLVENT: $CDCL_3$
SWEEP WIDTH: 2000 Hz.

NMR SPECTRUM FOR EXAMPLE XXIV

SOLVENT: $CDCL_3$
SWEEP WIDTH: 2000 Hz.

NMR SPECTRUM FOR EXAMPLE XXV, PART A.

IR SPECTRUM FOR EXAMPLE XXV, PART A.

NMR SPECTRUM FOR EXAMPLE XXV, PART B

SOLVENT: CDCL₃
SWEEP WIDTH: 1000 cps

IR SPECTRUM FOR EXAMPLE XXV, PART B.

NMR SPECTRUM FOR EXAMPLE XXVI

IR SPECTRUM FOR EXAMPLE XXVI

NMR SPECTRUM FOR EXAMPLE XXVIII

IR SPECTRUM FOR EXAMPLE XXVIII

NMR SPECTRUM FOR EXAMPLE XXIX

IR SPECTRUM FOR EXAMPLE XXIX

NMR SPECTRUM FOR EXAMPLE XXX

IR SPECTRUM FOR EXAMPLE XXX

GLC PROFILE FOR EXAMPLE XXXI

FIG.51
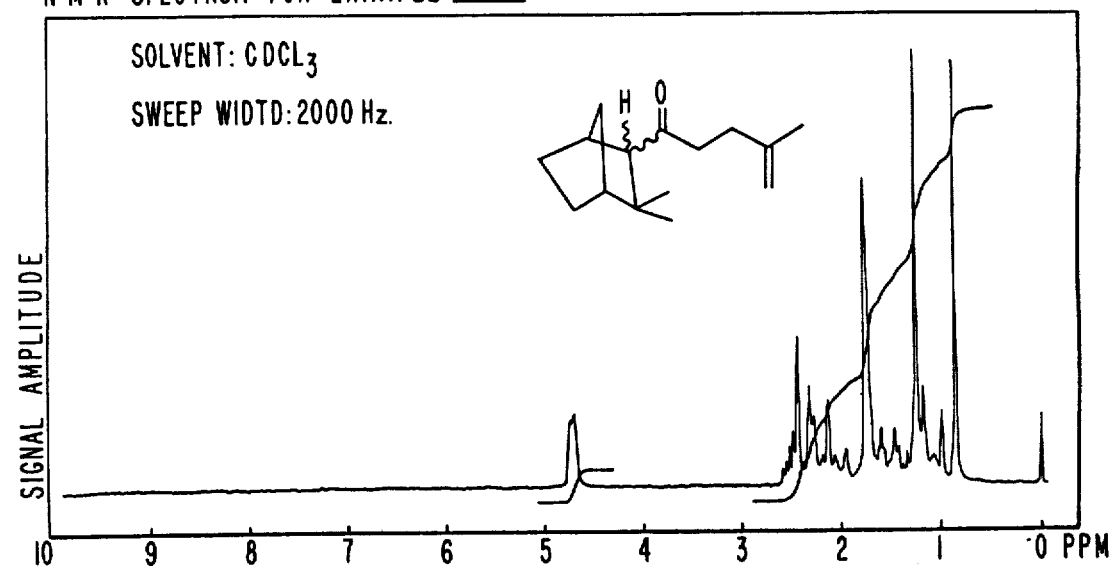
NMR SPECTRUM FOR EXAMPLE XXXI
FIG.52
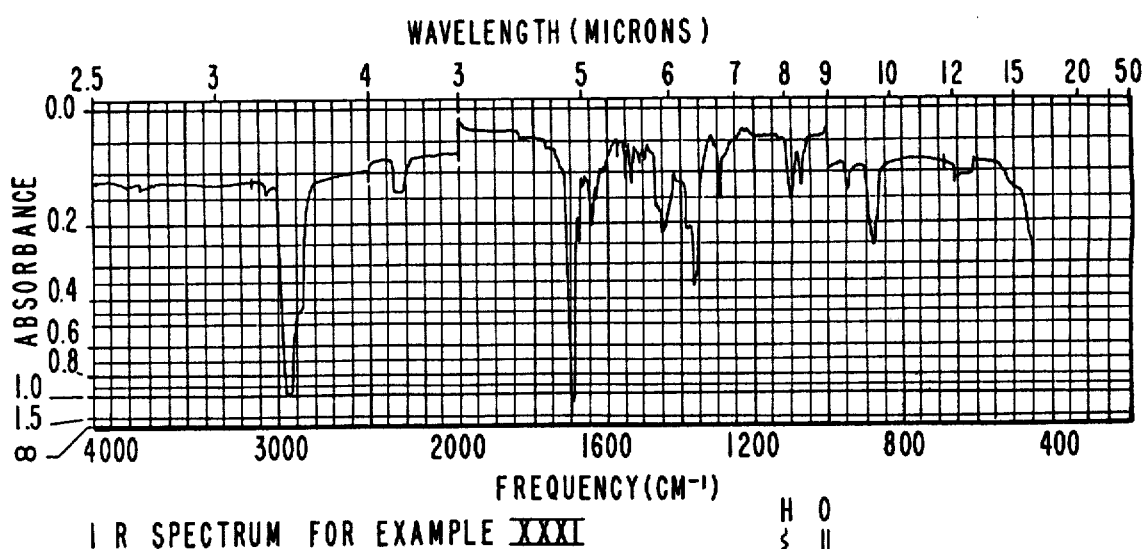
IR SPECTRUM FOR EXAMPLE XXXI
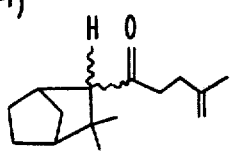

NMR SPECTRUM FOR EXAMPLE XXXI

IR SPECTRUM FOR EXAMPLE XXXI

FIG.55
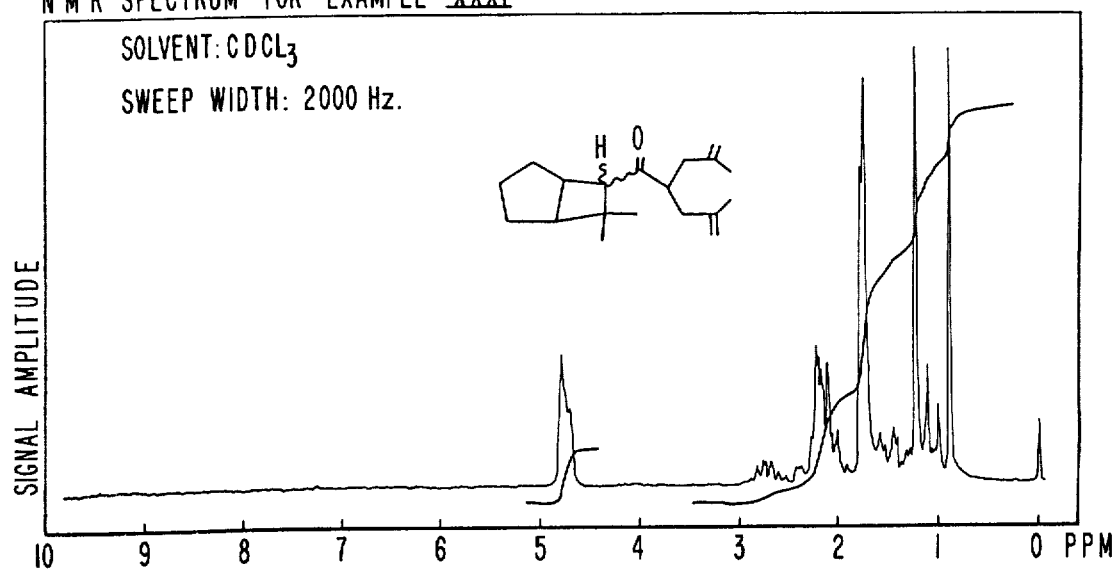
NMR SPECTRUM FOR EXAMPLE XXXI
FIG.56
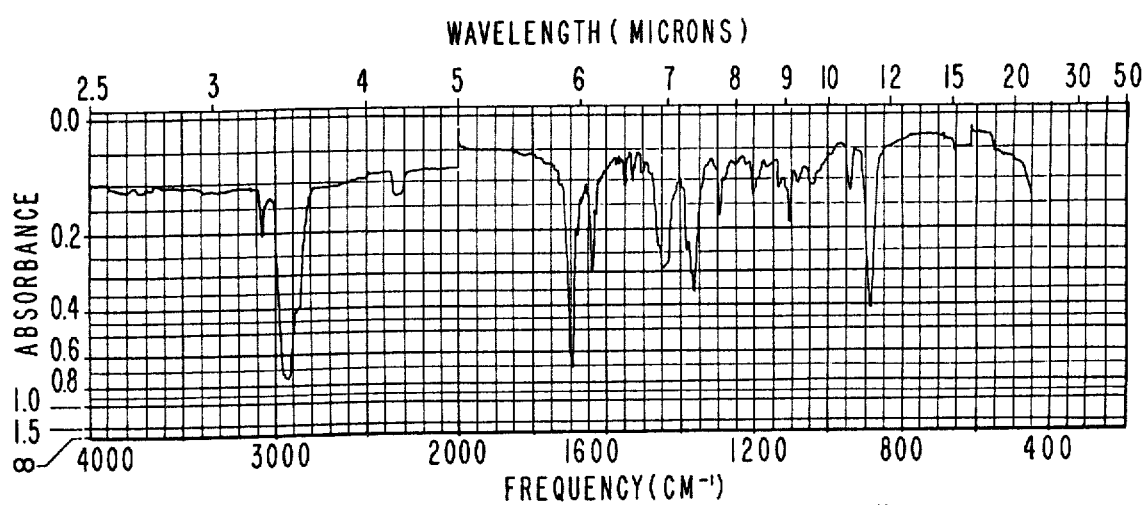
IR SPECTRUM FOR EXAMPLE XXXI
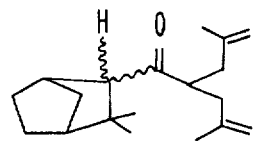

EXAMPLE IXI

EXAMPLE IXI

EXAMPLE IXI

EXAMPLE IXI

PROCESS OF ENHANCING THE AROMA OF A DETERGENT WITH NORBORNANE DERIVATIVES

This application is a divisional of U.S. application for letters patent Ser. No. 765,847, filed on Feb. 4, 1977, now U.S. Pat. No. 4,076,853, issued on Feb. 28, 1978.

BACKGROUND OF THE INVENTION

The present invention relates to substituted norbornane derivatives of the genus of compounds having the structure.

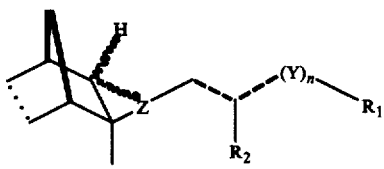

wherein each of the dashed lines represents a carbon-carbon single bond or a carbon-carbon double bond with the proviso that at least one of the dashed lines is a carbon-carbon single bond; wherein $n$ is 0 or 1 with the proviso that $n$ is 1 when both dashed lines are carbon-carbon single bonds and $n$ is 0 when one of the dashed lines is a carbon-carbon double bond; wherein $R_1$ and $R_2$ are each the same or different hydrogen or lower alkyl; wherein Y is:

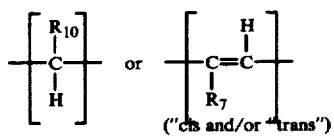

wherein Z is one of the moieties:

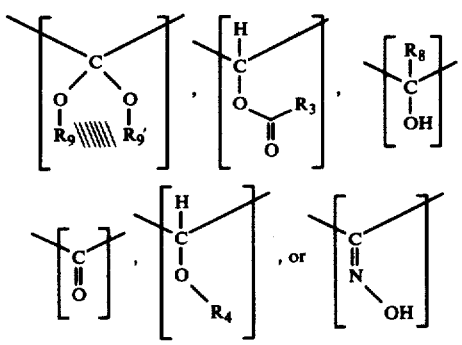

wherein $R_3$ and $R_4$ are each alkyl; wherein $R_7$, $R_8$ and $R_{10}$ are each the same or different hydrogen or lower alkyl; wherein $R_9$ and $R_9'$ taken separately are the same or different lower alkyl, or taken together is lower alkylene; wherein the dotted line represents a carbon-carbon single bond or a carbon-carbon double bond; and wherein each of the wavy lines represents, in the alternative, exo or endo isomers, produced by the novel processes of our invention, and to novel compositions using one or more of such substituted norbornane derivatives to alter, modify or enhance the flavor and/or aroma of consumable materials or impart flavor and/or aroma to consumable materials.

There has been considerable work performed relating to substances which can be used to impart (modify, augment or enhance) flavors and fragrances to (or in) various consumable materials. These substances are used to diminish the use of natural materials, some of which may be in short supply, and to provide more uniform properties in the finished product.

Fruity, piney/green, winey, fruity-estery, cedarwood, floral, woody, balsam tree resin-like, sweet, fruity berry, incense, minty, balsam, blueberry, piney, green fruity and/or pine needle/green aromas with piney, eugenol/clove, spicey, fruity, winey, sweet, banana-like, estery, balsam tree resin-like, woody, incense, warm tea-like, floral, cedarwood, rosey, berry, tea, astringent, bitter, camphoraceous green/earthy, green, minty, earthy, red beet-like, balsam natural-like, balsam resin-like, rum-like and/or blueberry tastes are particularly desirable for may uses in foodstuff flavors, chewing gum flavors, toothpaste flavors and medicinal product flavors.

Sweet, woody, fruity, cooling aroma prior to smoking and sweet, natural tobacco like smoke flavor characteristics in the mainstream on smoking are desirable in tobaccos and in tobacco flavoring compositions.

Intense and pleasant, twiggy, melony, sweet, woody, fruity, spicey (nutmeg, pepper), herbaceous, fir-balsam, thujone-like, cedar leaf, camphoraceous, musty, minty, fresh cut pine/spruce, artemesia, natural-like, cresylic, borneol aromas with strong armoise-like undertones are desirable in several types of perfume compositions, perfumed articles and colognes.

U.S. Pat. No. 3,852,358 issued on Dec. 3, 1974, discloses a process for producing 2-acetyl-3,3-dimethyl-5-norbornene in both the exo and endo forms which have uses in perfumery and other fragrance applications. These compounds have the structures:

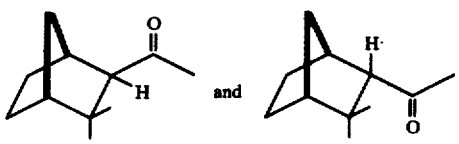

These compounds, produced by reaction of cyclopentadiene with mesityl oxide, are starting materials for producing a number of the compounds of our invention. However, the compounds of our invention have unexpected, unobvious and advantageous properties when compared with the 2-acetyl-3,3-dimethyl-5-norbornene of U.S. Pat. No. 3,852,358.

U.S. Pat. No. 3,942,761 discloses the use in perfumery of 4-(2'-norbornyl)-2-butanones having the structure:

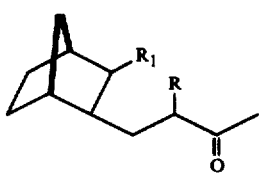

wherein $R_1$ is hydrogen or methyl and R is hydrogen or lower alkyl containing from 1 to 8 carbon atoms. Such compounds have structures which are different in kind from the structures of the compounds of our invention. Also disclosed as intermediates for producing the foregoing compounds are compounds having the generic structure:

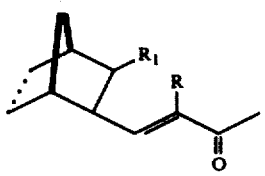

wherein the dotted line is a carbon-carbon single bond or a carbon-carbon double bond. In addition, the following reaction sequence is set forth therein:

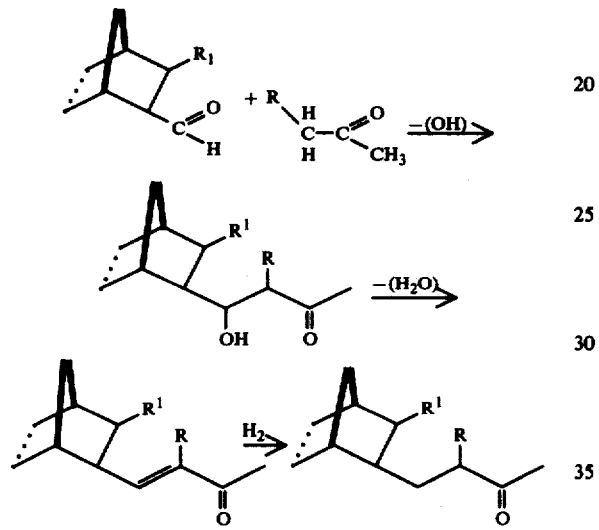

Arctander, "Perfume and Flavor Chemicals", 1969, Vol. 1, discloses the use in perfume compositions and in foodstuff flavors of "fenchone", "fenchyl alcohol", "camphene carbinol", and "camphene carbinyl acetate", thus:

(i) "1385: FENCHONE
laevo-Fenchone. (dextro- is known but less common as a fragrance material).
1,3,3-Trimethyl-2-norbornanone.
1,3,3-Trimethyl bicyclo-1,2,2-heptanone-2.

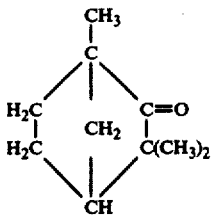

Warm-camphoraceous, powerful and diffusive, basically sweet odor.
Warm, somewhat burning and bitter taste with a medicinal note.
This ketone finds some use as a masking odor in industrial fragrances. It is also used in the reconstruction of Fennel Oil and a few other essential oils.

In spite of its rather unpleasant taste, it is used in various Berry complex flavors, in Spice complexes and in certain types of Liquer flavoring.
The concentration used is about 0.1 to 5 ppm in the finished product".

(ii) "1387: FENCHYL ALCOHOL
1,3,3-Trimethyl-2-norbornanol.
1,3,3-Trimethyl bicyclo-1,2,2-heptanol-2.
2-Fenchanol.
Fenchol.

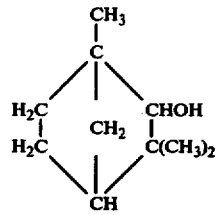

The racemic alpha-Fenchol has a somewhat lower melting point, and the beta-Fenchols are all liquid at room temperature.
Fenchol made by reduction of Fenchone from Cedarleaf oil is usually a mixture of several isomers, including the crystalline alpha-isomers. The beta-isomer forms a crystalline Hydrate which may be solid at room temperature.
Almost insoluble in water, soluble in alcohol, miscible with oils. Powerful and diffusive, Camphor-like, but sweeter and more Citrus-like almost Lime-like odor with more or less of an earthy-dry character, according to the composition and isomer-ratio.
The taste is somewhat bitter-Lime-like, camphoraceous and slightly woody-musty.
This interesting alcohol (or mixed alcohols) finds use in perfume compositions ranging from woody or herbaceous to Citrus-Lime and even certain floral types. It produces power and "lift" to floral fragrances, and solid background to Lime and other Citrus bases, having the advantage over the Terpenes in being very stable in soap.
Fenchyl alcohol is also used in flavor compositions such as Strawberry and other berries, Lime and Spice, etc.
The concentration is normally low, e.g. 0.2 up to 5 ppm in the finished product".

(iii) "1028: 3,3-DIMETHYL-$\Delta^2$, beta-NORBORNANE-2-ETHANOL "Camphene carbinol".

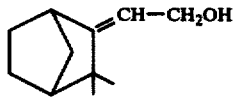

Sweet-camphoraceous, warm and soft odor with a woody undertone. Upon standing it may develop an odor resembling that of Celluloid.
Although rarely offered commercially, this chemical could find some use in perfume compositions of the woody, Oriental and orrisy type, in new variations of Pine fragrances, and in various soap and detergent perfumes".

(iv) "1029: 3,3-DIMETHYL-$\Delta^2$- beta-NORBORNANE-2-ETHYLACETATE

"Camphene carbinyl acetate".

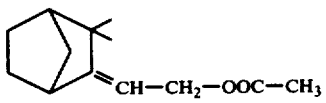

Mild and sweet-toothy odor with a floral-piney undertone. The commercial products are probably not well-defined single chemicals, and great variations in odor have been observed.

This ester has been developed in line with the research on Sandalwood type odors. The parent alcohol "Camphene carbinol" was once considered useful as a Sandalwood type material, but it has found more use as a sweetening and enriching ingredient in sophisticated Pine fragrances. The title ester finds limited use in perfume compositions of woody character, Fougeres, Pine fragrances, etc. and it blends very well with the Cyclohexanol derivatives, Ionones, iso-Bornylacetate, Nitromusks, etc.".

U.S. Pat. No. 3,928,456 discloses monocyclic compounds having the generic structure:

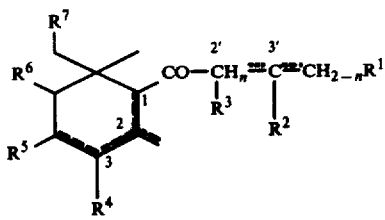

containing one double bond in position 2'-or 3'- of the acyl side-chain and either one double bond in position 1- or 2-(as shown in the above formula, the double bond in the 2 position can be either in the cycle or the side chain), or two conjugated double bonds in positions 1- and 3- of the cycle, the double bonds being represented by dotted lines, and wherein n is zero or 1, $R^1$, $R^2$ and $R^3$ represent hydrogen or one of them a lower alkyl radical, such as methyl or ethyl, and the others hydrogen, and $R^4$, $R^5$, $R_6$ and $R^7$ represent hydrogen or one of them a lower alkyl radical, such as methyl or ethyl, and the others hydrogen, as being useful in perfumery and food flavors and also flavors, beverages, animal feeds and tobaccos. Specifically disclosed in this patent is a compound having the structure:

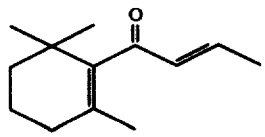

U.S. application for letters patent Ser. No. 551,030, filed on Feb. 19, 1975 discloses, interalia, perfumery uses of compounds having the structures:

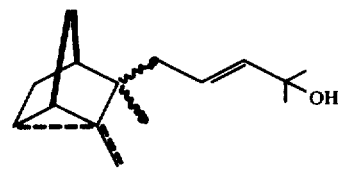

and

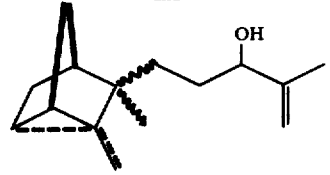

wherein one of the dashed lines is a carbon-carbon bond and each of the wavy lines is a carbon-carbon single bond, one of the carbon-carbon single bonds represented by the wavy line being epimeric with respect to the other of the carbon-carbon single bonds represented by the wavy line.

In addition, various processes and compounds relating to the synthesis of synthetic sandalwood oil components are described in the following U.S. Patents:

(i) Perfume Compounds And Process For Preparing Same-3,673,261 issued June 27, 1972:

COMPOUNDS

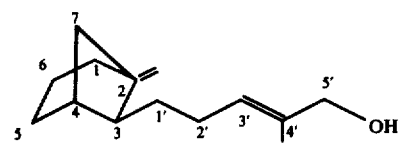

2-methylene-3-exo-(trans-4'-methyl-5'-hydroxypent-3'-enyl)bicyclo[2.2.1]heptane; trans-3-normethylbeta-santalol

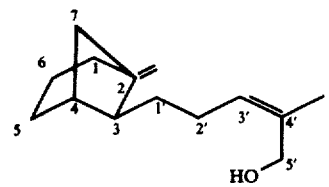

2-methylene-3-exo-(cis-4'-methyl-5'-hydroxypent-3'-enyl)-bicyclo[2.2.1]heptane; cis-3-normethyl-beta-santalol

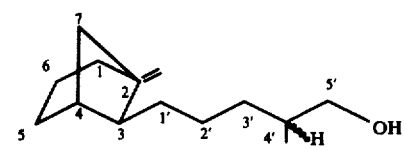

2-methylene-3-exo-(4'-methyl-5'-hydroxypentyl)-bicyclo[2.2.1]heptane; 3-normethyldihydro-beta-santalol (ii) Dihydro-beta-santalol and Processes For Preparing Dihydro-beta-santalol From 3-Endo-Methyl-3-Exo-(4'-Methyl-5'-Hydroxyphenyl)-Norcamphor-3,673,263 issued June 27, 1972:

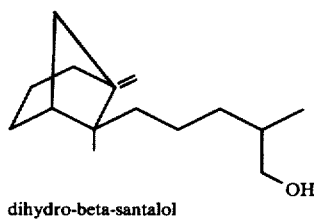

dihydro-beta-santalol (iii) Process For Preparing Beta-Santalol From 3-Methylnorcamphor - 3,662,008 issued May 9, 1972:

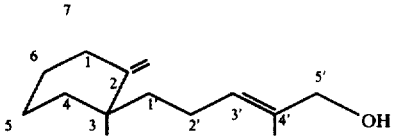

endo-3-methyl-exo-3-(cis-5'-hydroxy-4'-methylpent-3'-enyl)-2-methylenebicyclo[2.2.1]heptane

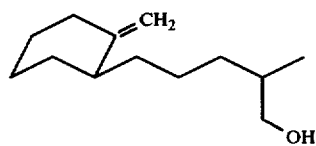

endo-3-methyl-exo-3-(trans-5'-hydroxy-4'-methylpent-3'-enyl)-2-methylenebicyclo[2.2.1]heptane (iv) Process For Preparing Dihydro-Beta-Santalol From 3-Endo-Methyl-3-Exo-(4'-Methyl-5'-Hydroxypentyl)-Norcamphor - 3,673,266, issued June 27, 1972:

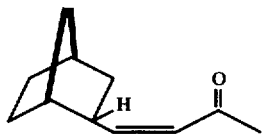

dihydro-beta-santalol

None of the compounds disclosed in either U.S. Pat. No. 3,928,456 or U.S. application for letters patent Ser. No. 551,030, filed Feb. 19, 1975 have properties even closely similar to the properties of the compounds of the instant application.

Chem. Abstracts, Vol. 84, 73728n (abstract of Karaev, et al, Zh.Org.Khim. 1975, 11(12), 2622) discloses preparation of the compound:

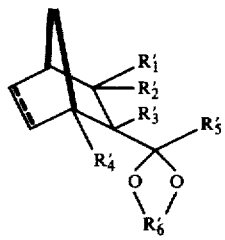

by reaction of:

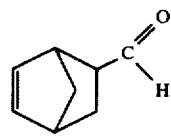

with

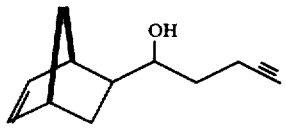

to form:

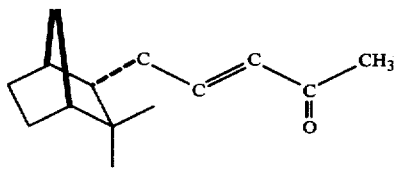

followed by isomerization with HgO/H$_2$SO$_4$.

Klein and Rojahn, Chem.Abstracts, Vol. 84, 90327y (1976) discloses the use of compounds having the structure:

(wherein the dashed line is a single or double bond) as an intermediate in the preparation of beta-santalol; but no organoleptic properties of these norbornane derivatives are disclosed. U.S. Pat. No. 3,748,344, issued on July 24, 1973, discloses that chemical compounds characterized by the structural formula:

wherein the dashed line represents the presence of a single or a double bond wherein $R_1'$, $R_2'$, $R_3'$, and $R_4'$ each represent hydrogen or lower methyl and $R_5'$ represents hydrogen or lower alkyl and $R_6'$ represents a polymethylene radical of from 2 to 4 carbon atoms which is unsubstituted or substituted with lower alkyl, which "as a whole exhibits a characteristic, pleasant, strong and long lasting aroma which is highly useful in the preparation of fragrance compositions and perfume products". Various notes are described such as green, cuminic, walnut, raw potato, earthy, camphoraceous, civet, walnut bark, neroli, anise, vegetable, menthone, animal, minty, eucalyptol, cucumber, pine and fecal. The specific ketals of our invention are not disclosed in U.S. Pat. No. 3,748,344.

In addition, U.S. Pat. No. 3,748,344 discloses as chemical intermediates for preparing the above ketal, a compound having the generic structure:

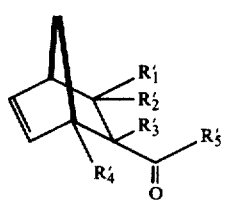

wherein $R_1'$, $R_2'$, $R_3'$, $R_4'$, and $R_5'$ have the same meaning as defined above.

However, the specific genuses and compounds of our invention are not set forth in U.S. Pat. No. 3,748,344 and all uses of them as chemical intermediates for this genus of ketones is set forth in U.S. Pat. No. 3,748,344 at column 3, lines 61-70.

No prediction of the organoleptic properties of the compounds of the instant invention can be made by a study of the disclosure of U.S. Pat. No. 3,748,344.

Chemical Abstracts, Vol. 71, 49664z (abstract of SadykhZade, et al (U.S.S.R.). Dokl. Akad. Nauk Azerb. SSR 1968, 24(11), 38-41) discloses the synthesis of exo and endo forms of the compounds having the structures:

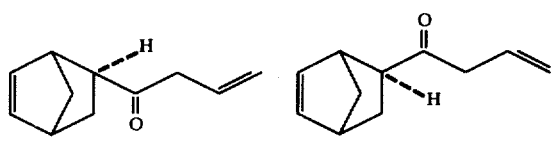

Chemical Abstracts, Vol. 81, 135512m (abstract of Akhmedov, I.M., et al (Inst. Georg. Fiz. Khim., Baku, U.S.S.R.). Dokl. Akad. Nauk Az. SSR 1974, 30(4), 18-21) discloses the synthesis of the compound having the structure:

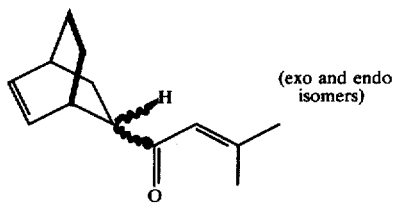

(exo and endo isomers)

None of the Chemical Abstracts references discloses compounds which have a close structural relationship to the compound of the instant invention. In any event, the organoleptic properties of the compounds of the Chemical Abstract references are different in kind from those of the compounds of the instant invention.

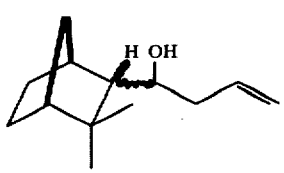

as synthesized in Example II.

Figure 2:
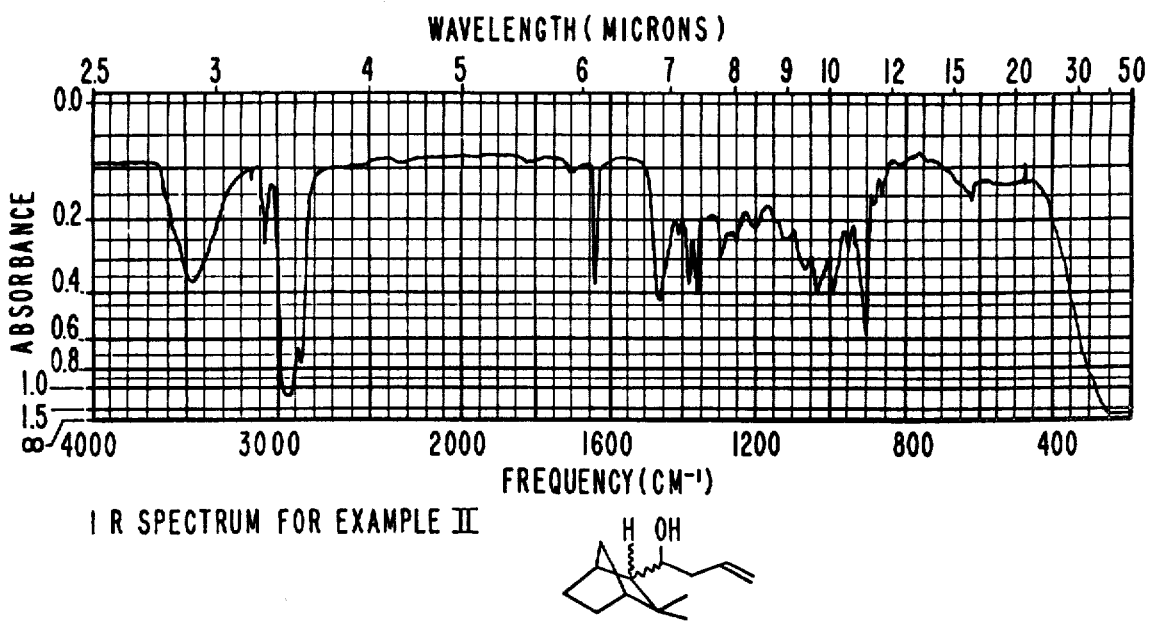

FIG. 2 illustrates the Infrared spectrum of the compound having the structure:

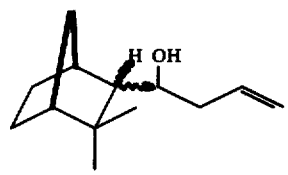

as synthesized in Example II.

Figure 3:
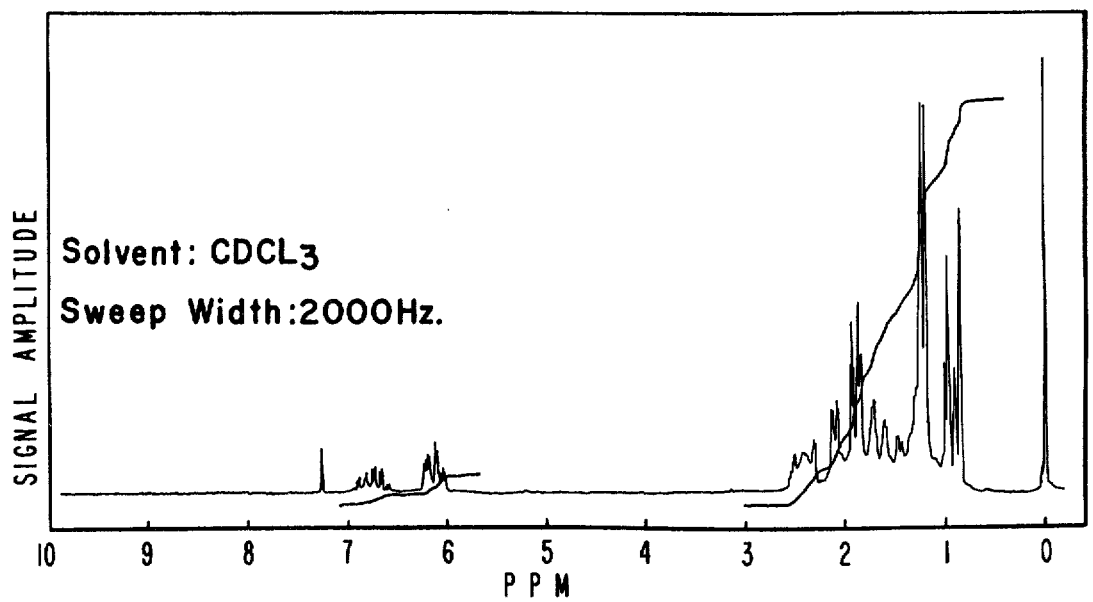

FIG. 3 illustrates the NMR spectrum of the cis isomer, having the structure:

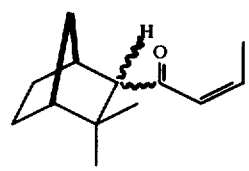

produced according to Example III.

Figure 4:
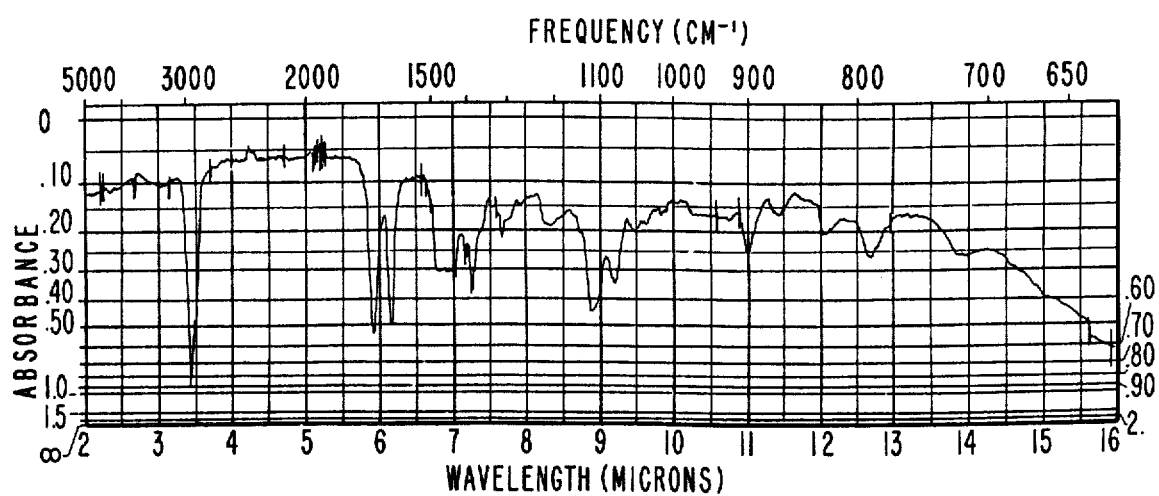

FIG. 4 illustrates the Infrared spectrum of the cis isomer, having the structure:

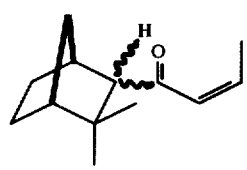

as synthesized in Example III.

Figure 5:
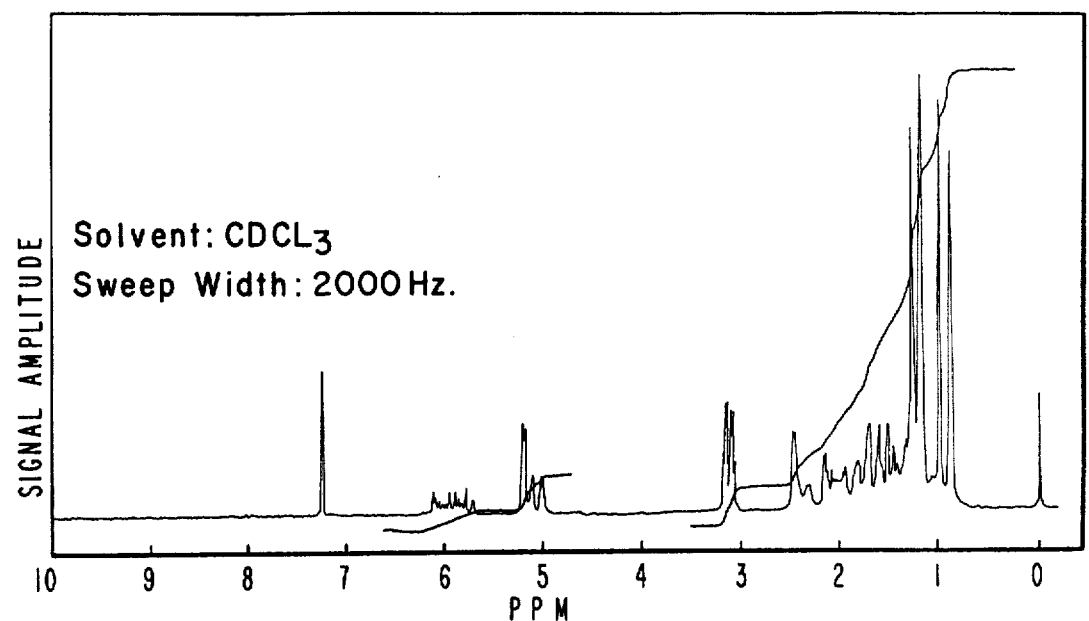

FIG. 5 illustrates the NMR spectrum of the compound having the structure:

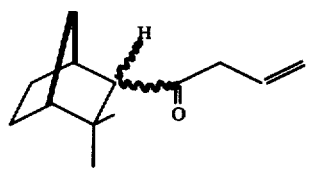

as synthesized in Example III.

Figure 6:
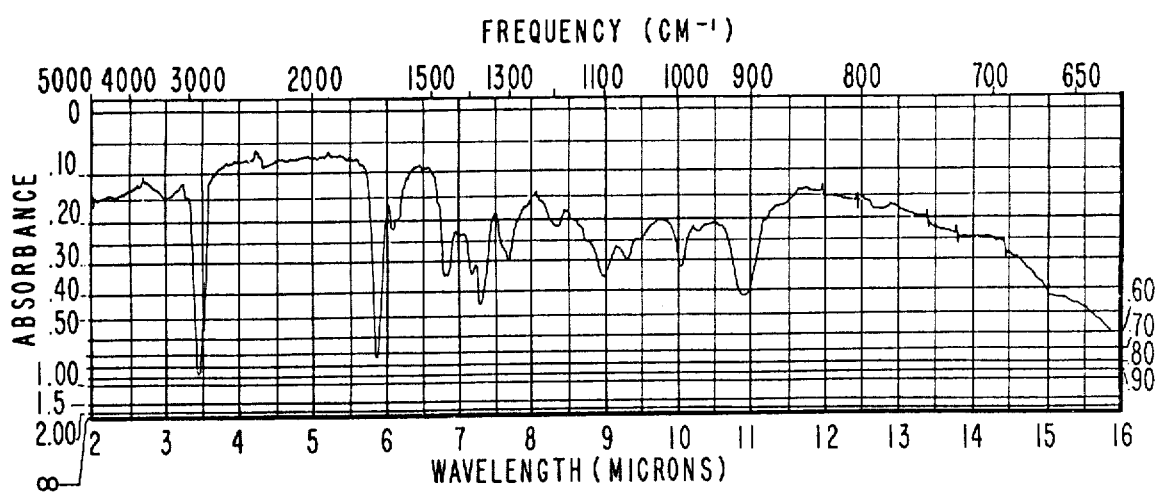

FIG. 6 illustrates the Infrared spectrum of the compound having the structure:

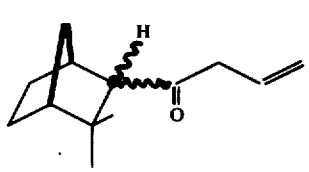

as synthesized in Example III.

Figure 7:
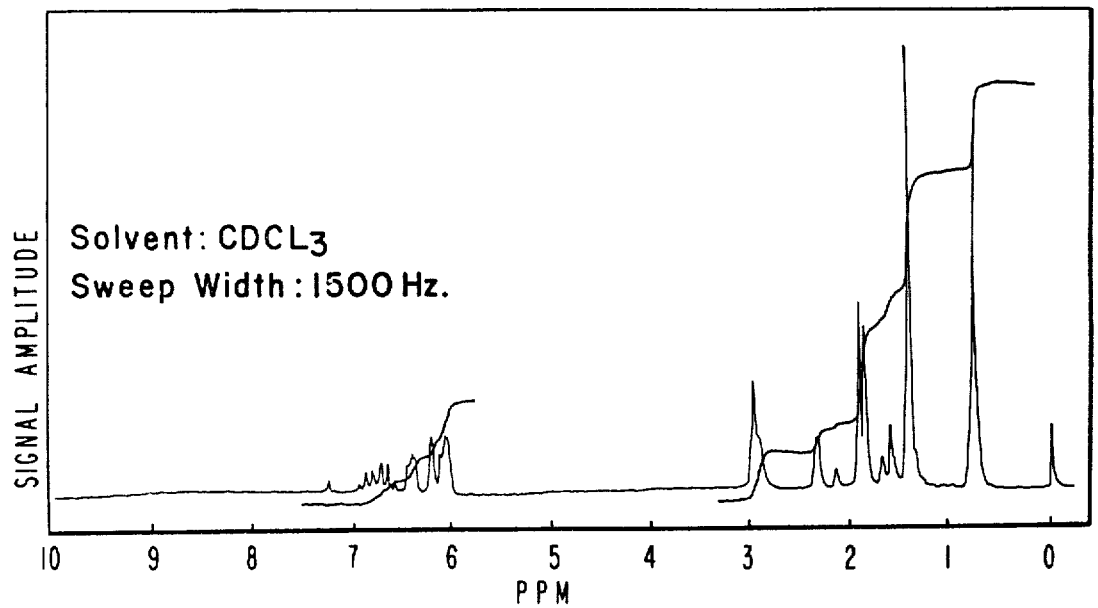

FIG. 7 illustrates the NMR spectrum of the compound having the structure:

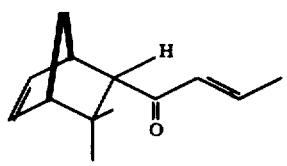

as synthesized in Example XI.

Figure 8:
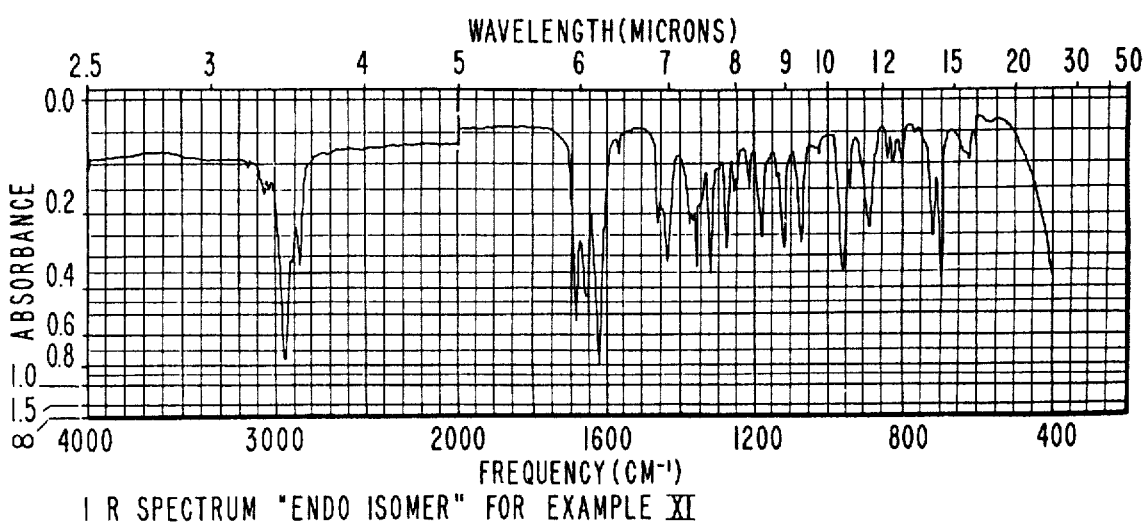

FIG. 8 illustrates the Infrared spectrum of the compound having the structure:

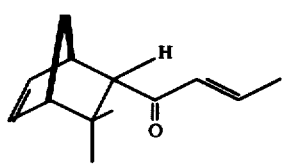

as synthesized in Example XI.

Figure 9:
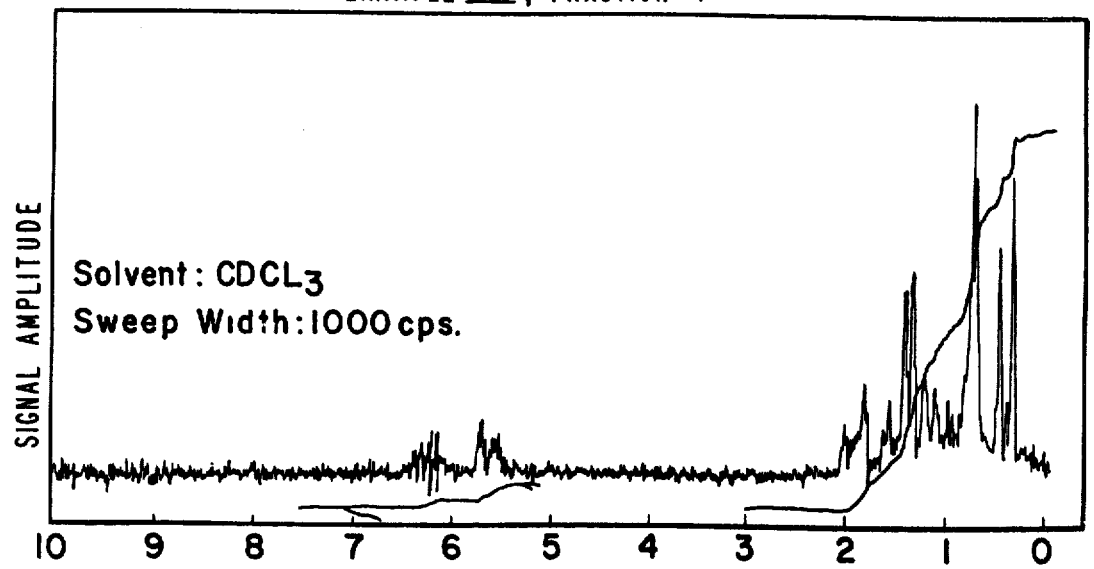

FIG. 9 illustrates the NMR spectrum for fraction 7 of Example XII containing primarily a compound having the structure:

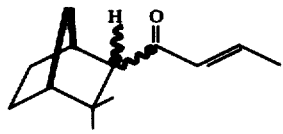

Figure 10:
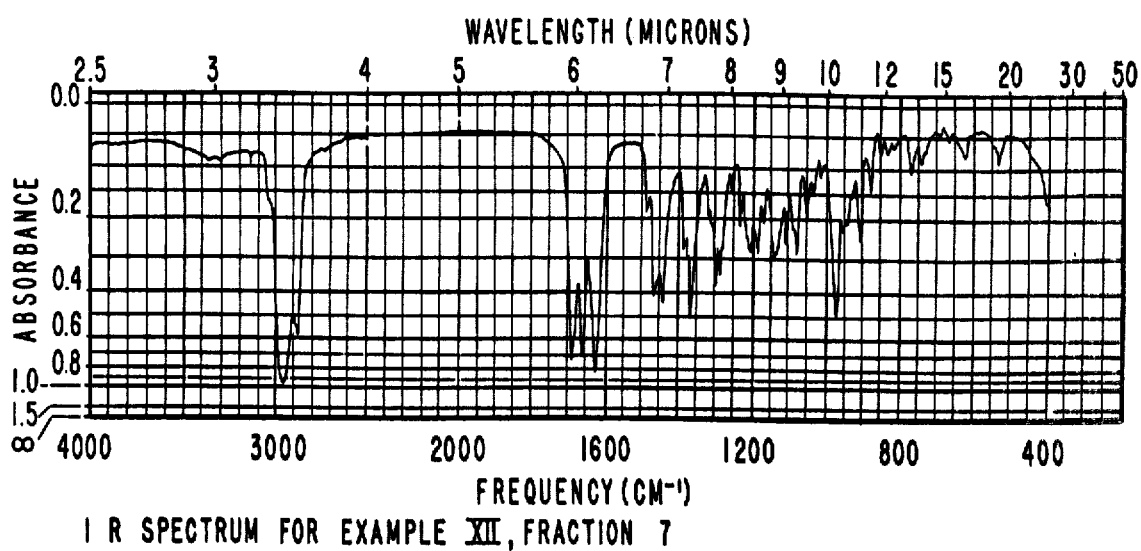

FIG. 10 illustrates the Infrared spectrum for fraction 7 of Example XII containing primarily a compound having the structure:

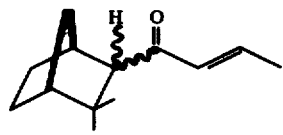

FIG. 11 illustrates the NMR spectrum for fraction 5 of Example XVII which is a compound having the structure:

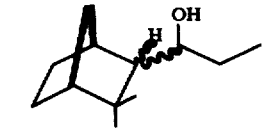

FIG. 12 illustrates the Infrared spectrum for fraction 5 of Example XVII which is the compound having the structure:

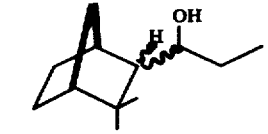

Figure 13:
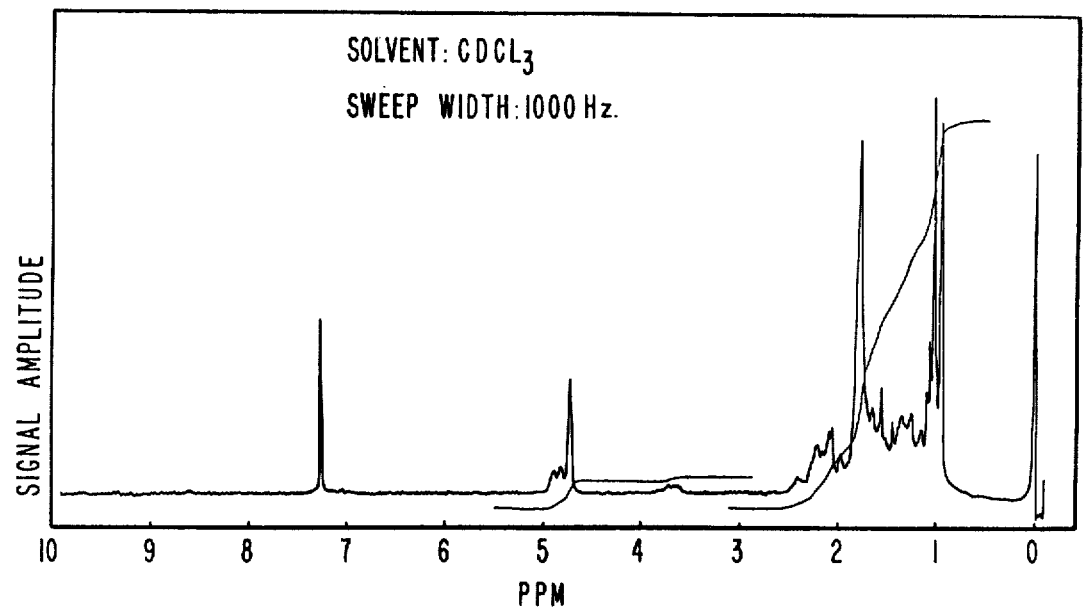
Figure 14:
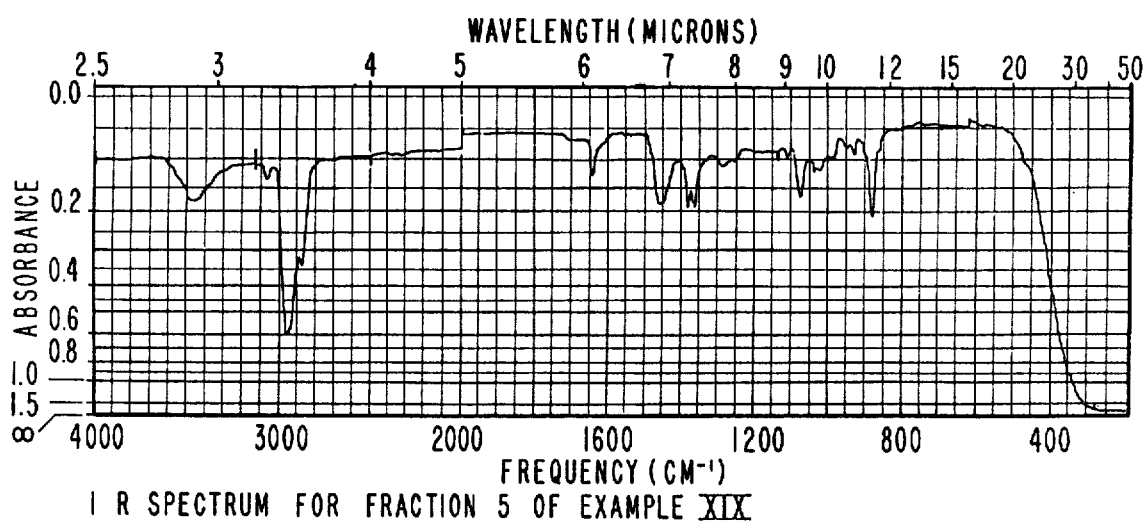

FIG. 13 illustrates the NMR spectrum for fraction 5 of Example XIX which is the compound having the structure:

FIG. 14 illustrates the Infrared spectrum for fraction 5 of Example XIX which is a compound having the structure:

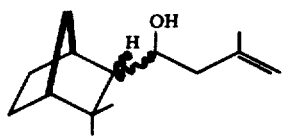

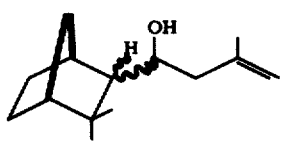

Figure 15:
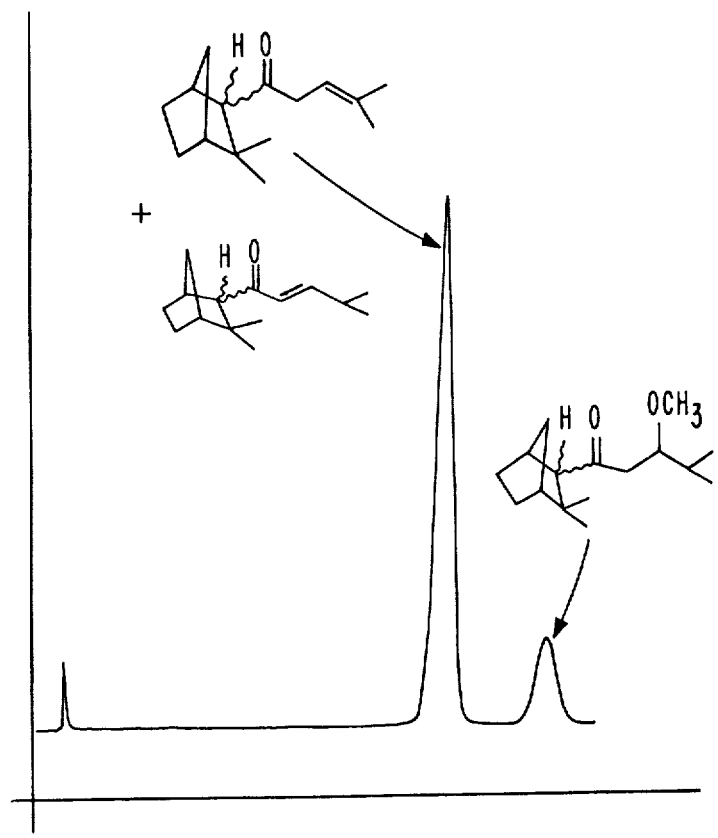

FIG. 15 illustrates the GLC profile of the mixture produced according to Example XX.

Figure 16:
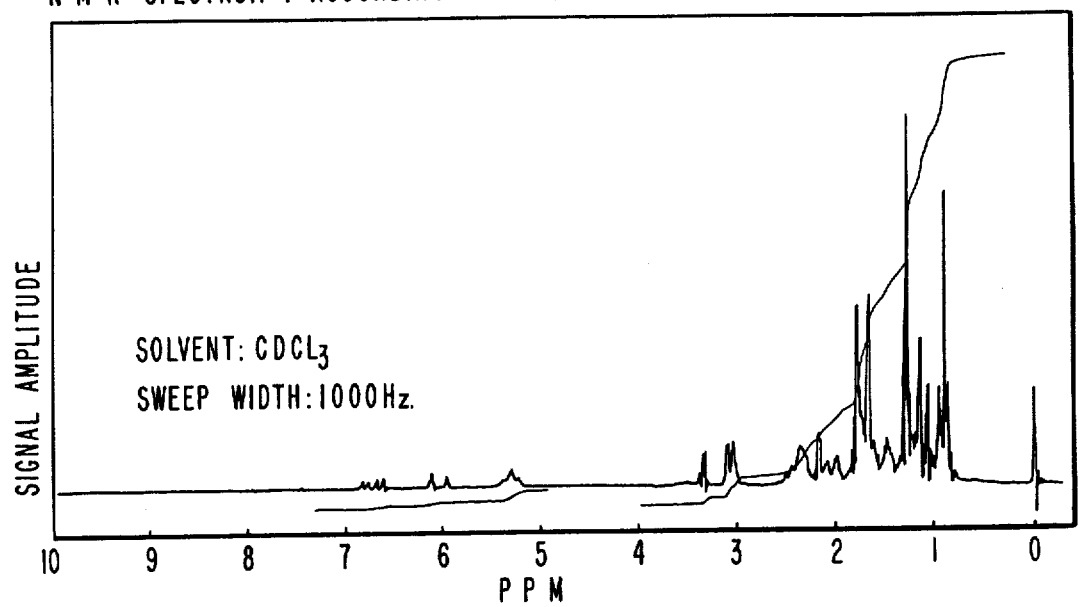

FIG. 16 is an illustration of the NMR spectrum of the mixture of three compounds in fraction 12 of Example XX, the three compounds having the structures:

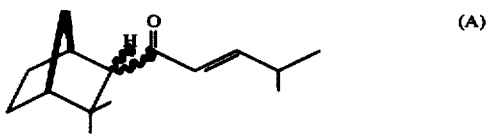 (A)

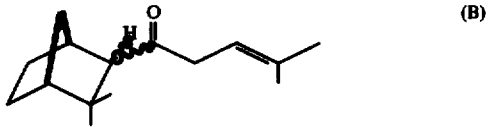 (B)

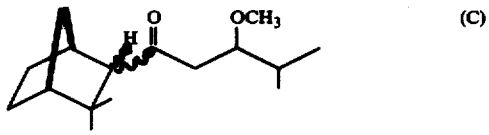 (C)

Figure 17:
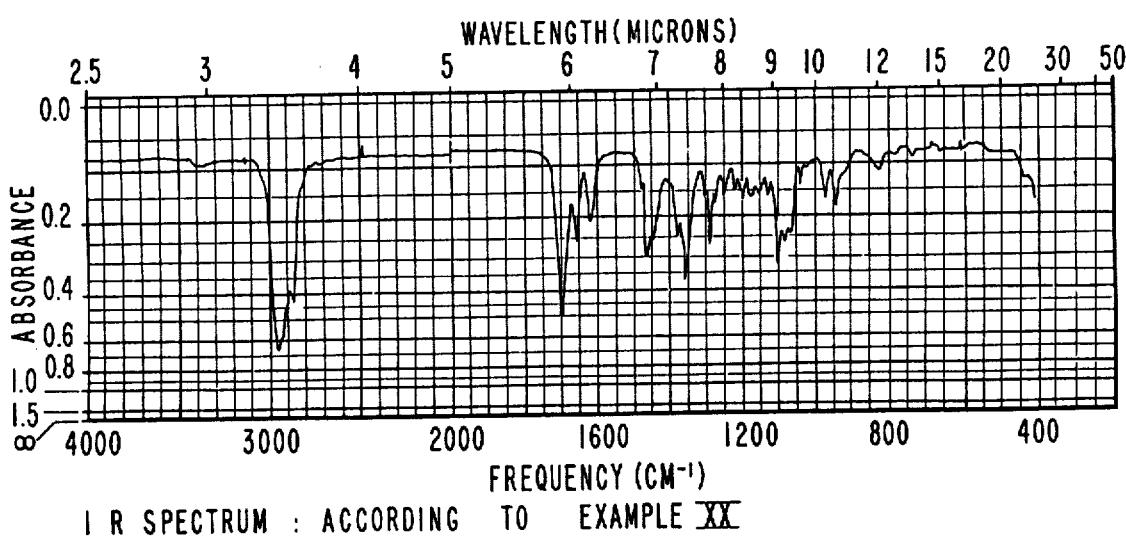

FIG. 17 illustrates the Infrared spectrum of fraction 12 of Example XX which is a mixture of the three compounds having the structures:

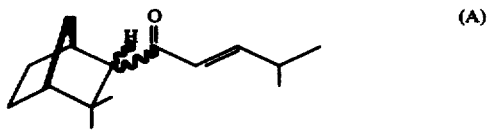 (A)

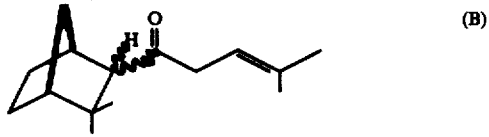 (B)

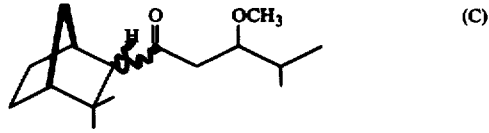 (C)

Figure 18:
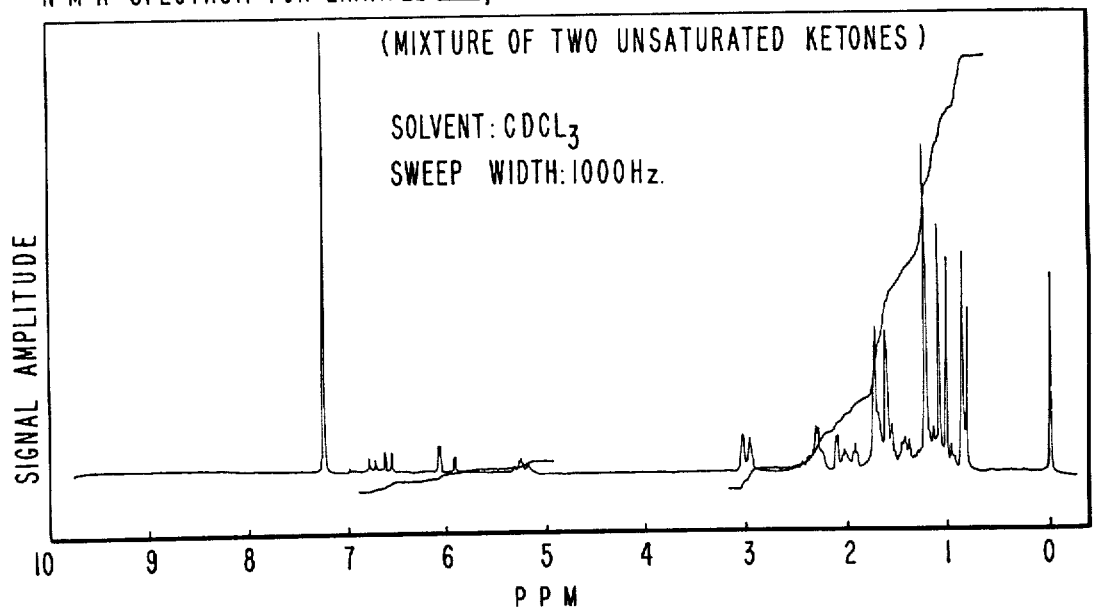

FIG. 18 illustrates the NMR spectrum of peak 1 from fraction 18 of Example XX, which is a mixture of the two ketones having the structures:

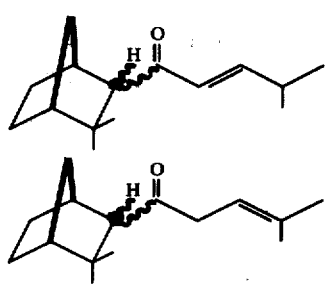

(A)

(B)

Figure 19:
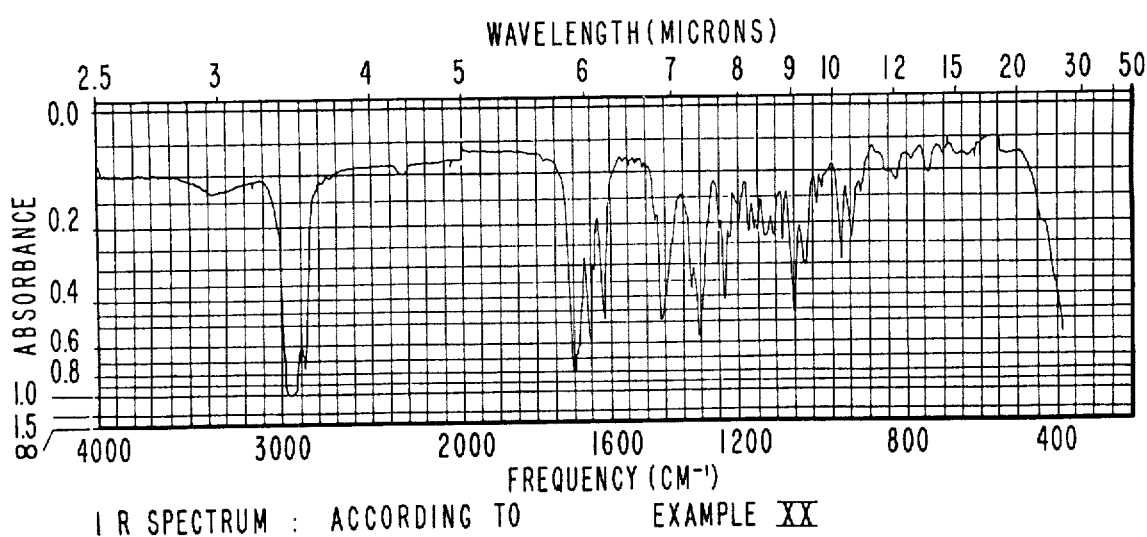

FIG. 19 illustrates the Infrared spectrum of peak 1, fraction 18 of Example XX, which is a mixture of the two ketones having the structures:

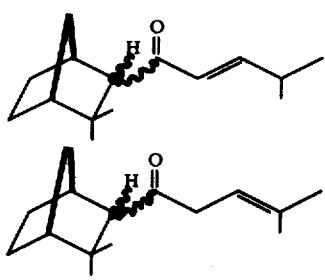

(A)

(B)

Figure 20:
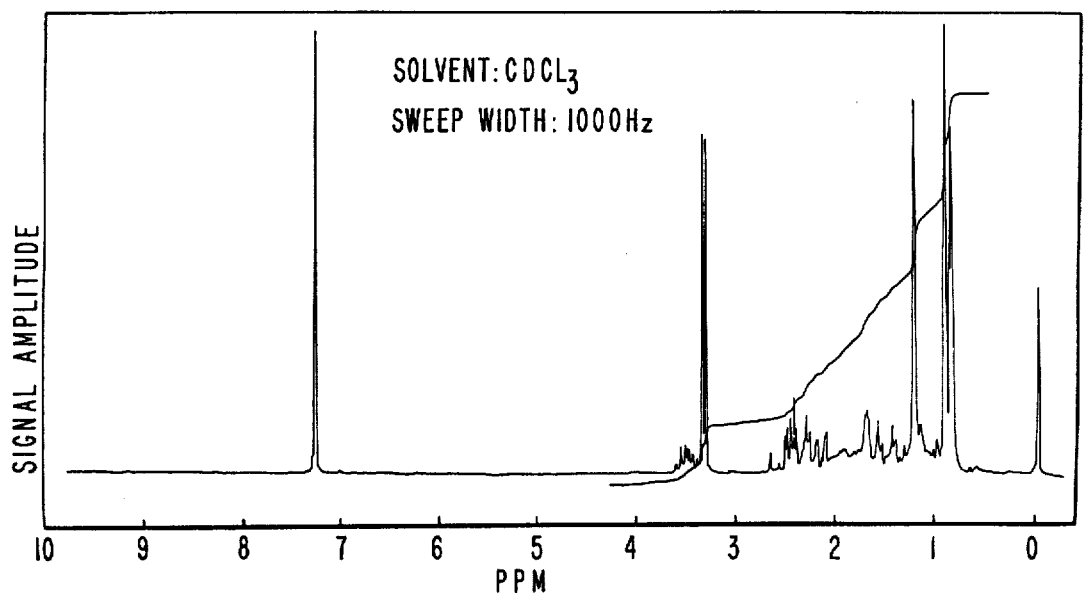

FIG. 20 illustrates the NMR analysis of the keto ether produced according to Example XX, having the structure:

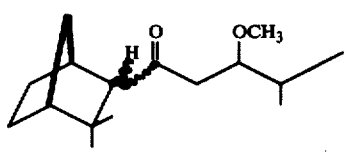

(C)

Figure 21:
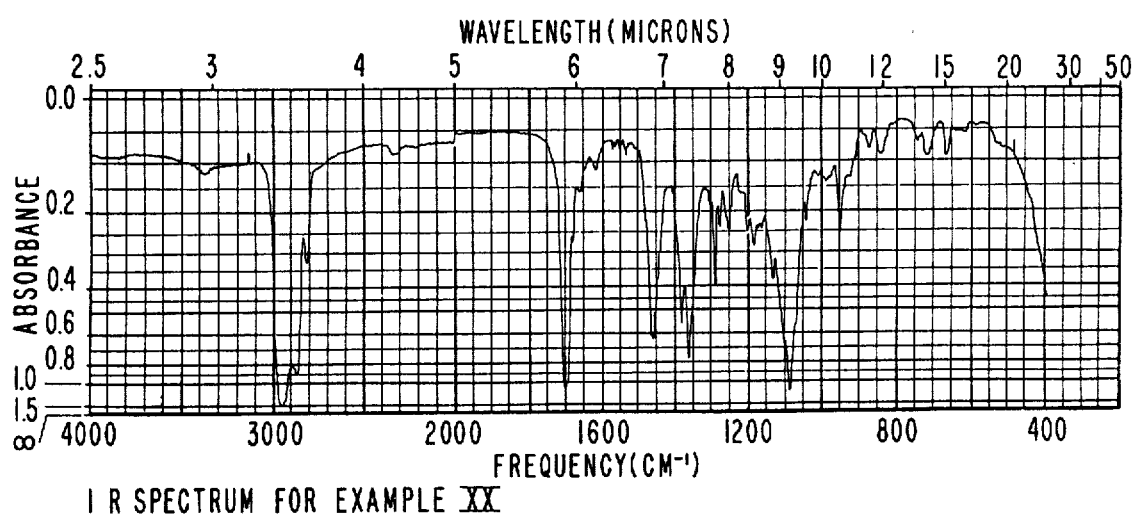

FIG. 21 illustrates the Infrared spectrum for the keto ether having the structure:

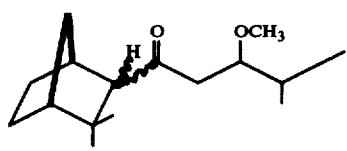

(C)

produced according to Example XX.

Figure 22:
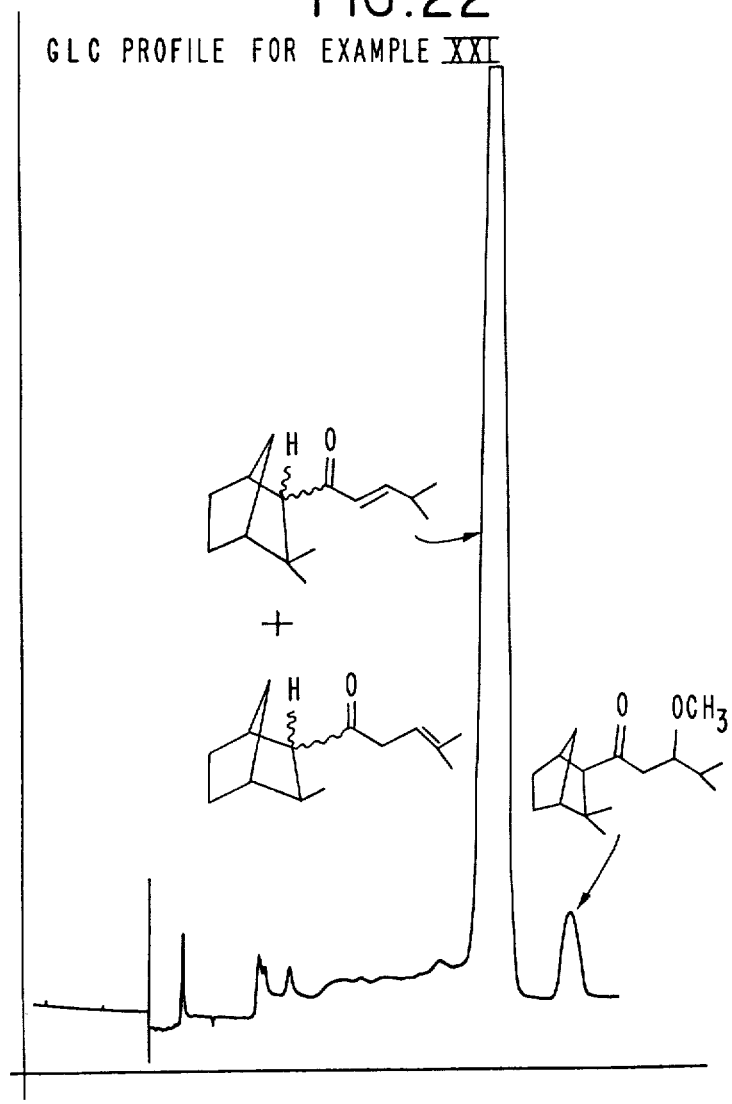

FIG. 22 illustrates the GLC profile for the mixture of ketones and keto ethers produced according to Example XXI, having the structures:

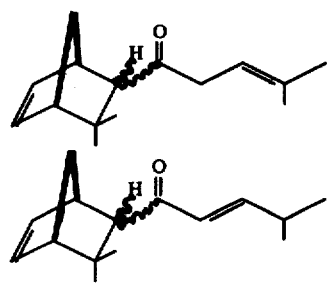

-continued

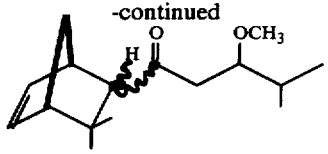

Figure 23:
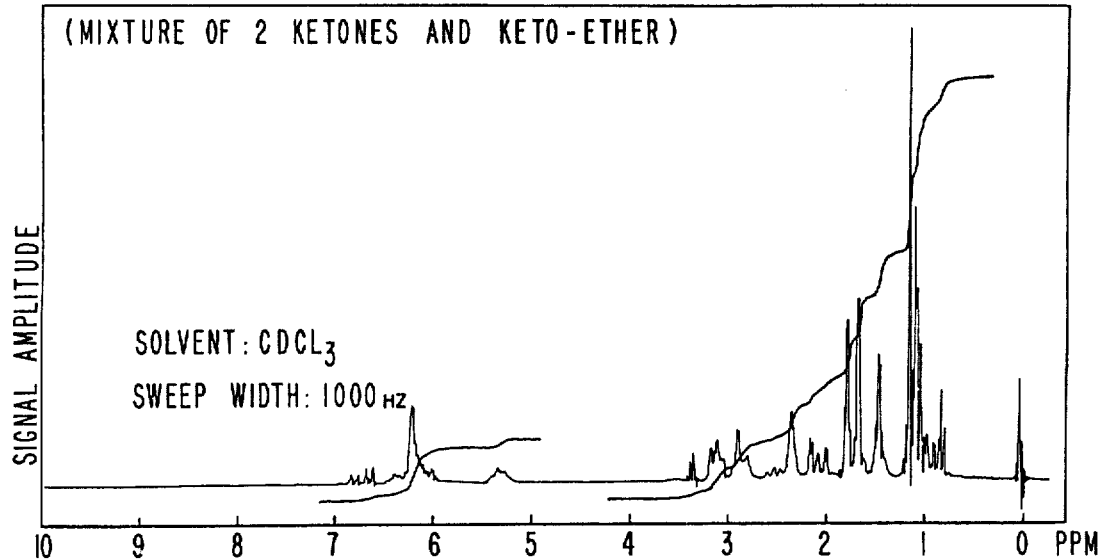

FIG. 23 is an illustration of the NMR spectrum for the mixture of ketones and keto ethers produced according to Example XXI, having the structures:

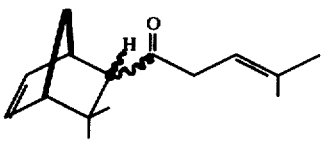

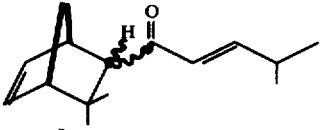

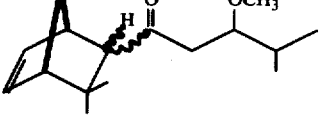

Figure 24:
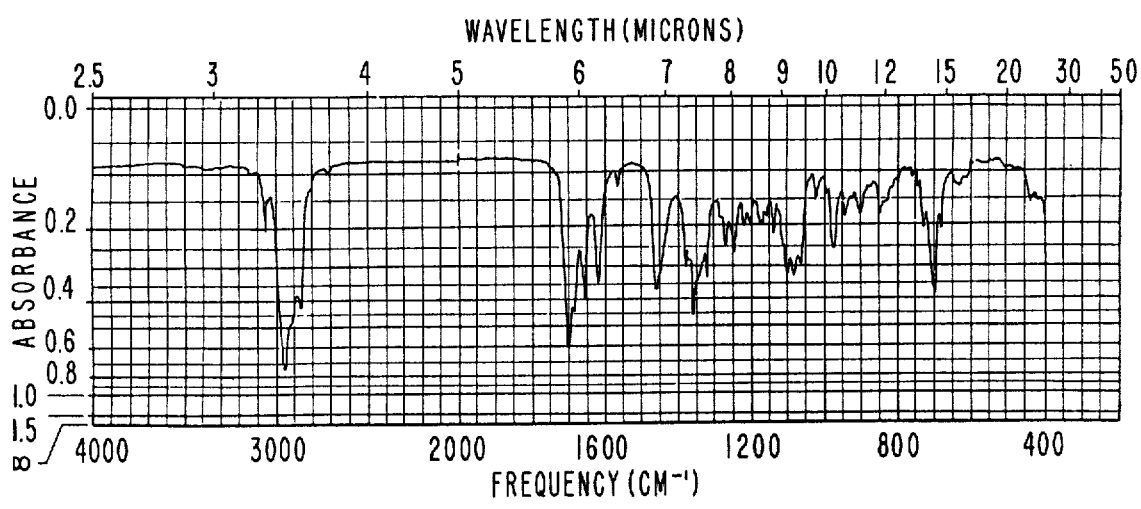

FIG. 24 is the infrared spectrum for the mixture of ketones and keto ethers produced according to Example XXI.

Figure 25:
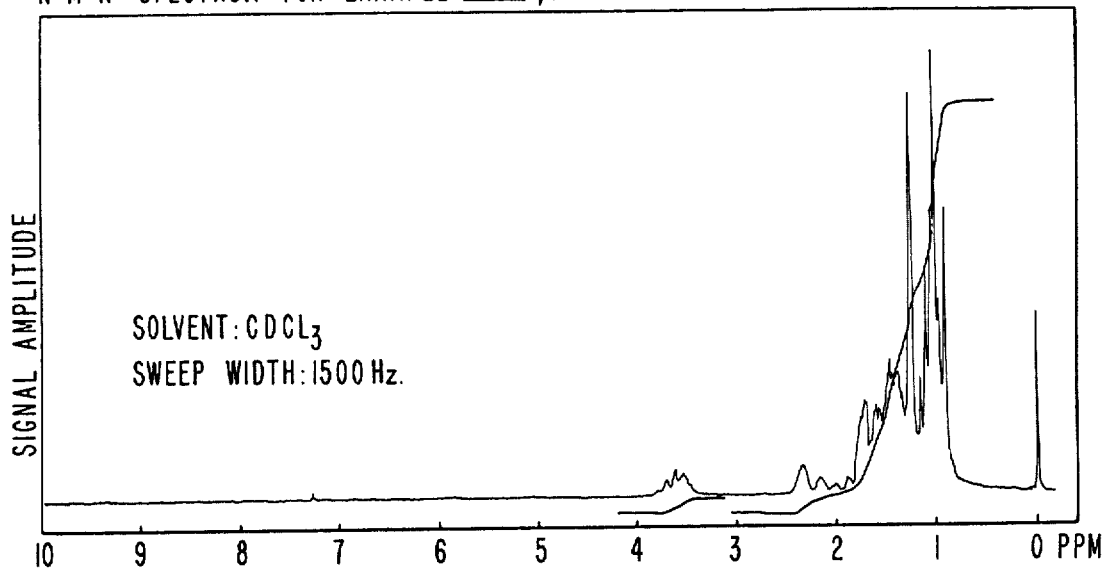

FIG. 25 illustrates the NMR spectrum of the compound having the structure:

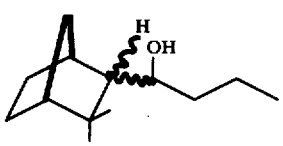

produced according to Part A of Example XXII (fraction 4).

Figure 26:
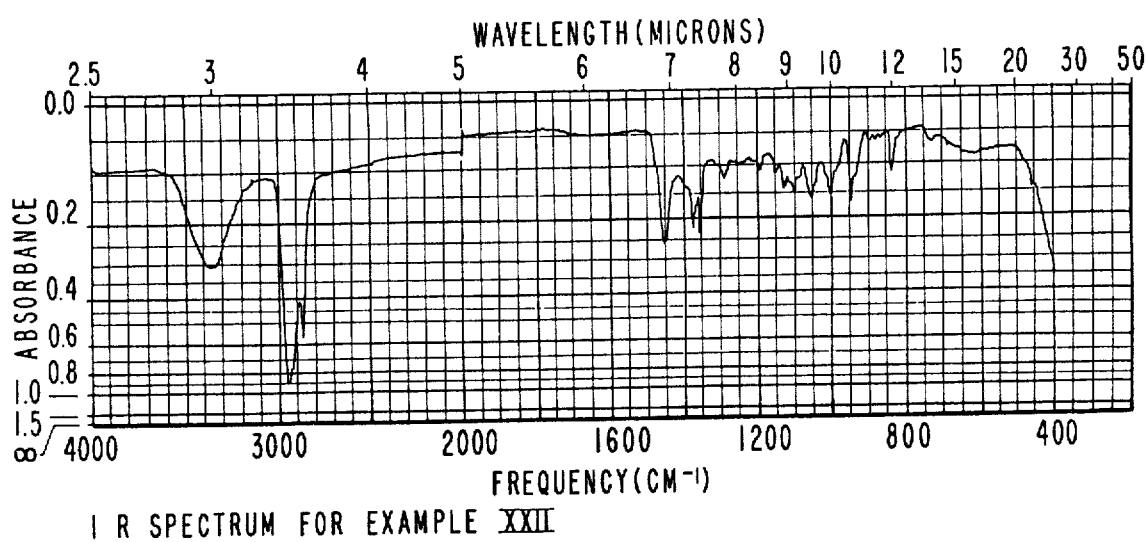

FIG. 26 illustrates the Infrared spectrum of the compound having the structure:

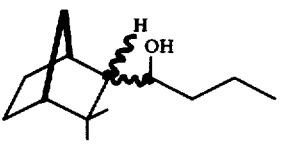

produced according to Part A of Example XXII (fraction 4).

Figure 27:
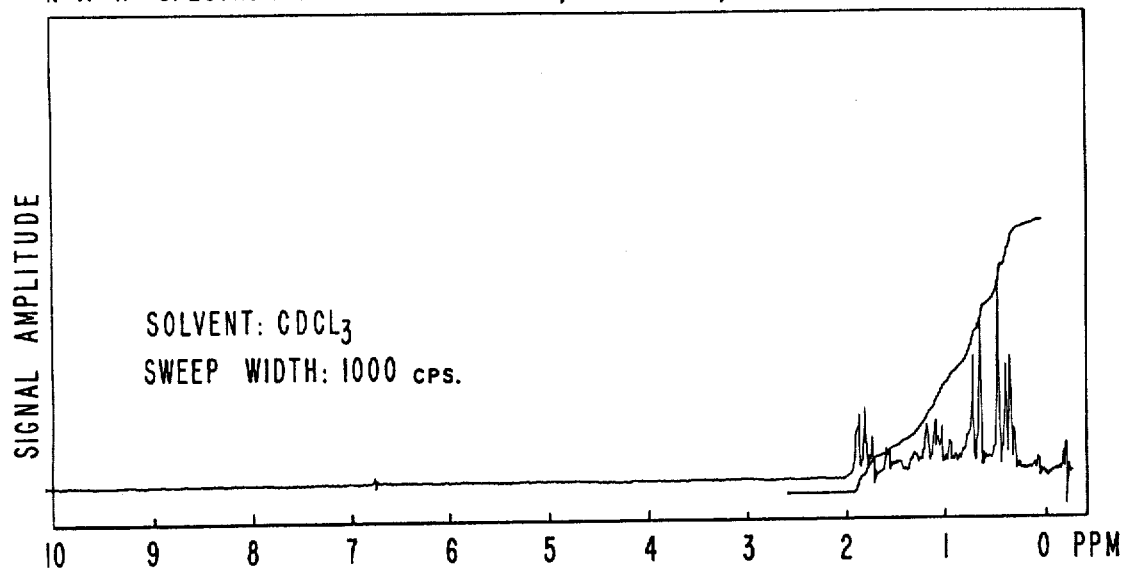

FIG. 27 illustrates the NMR spectrum for the compound having the structure:

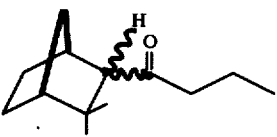

produced according to Part B of Example XXII (fraction 2).

Figure 28:
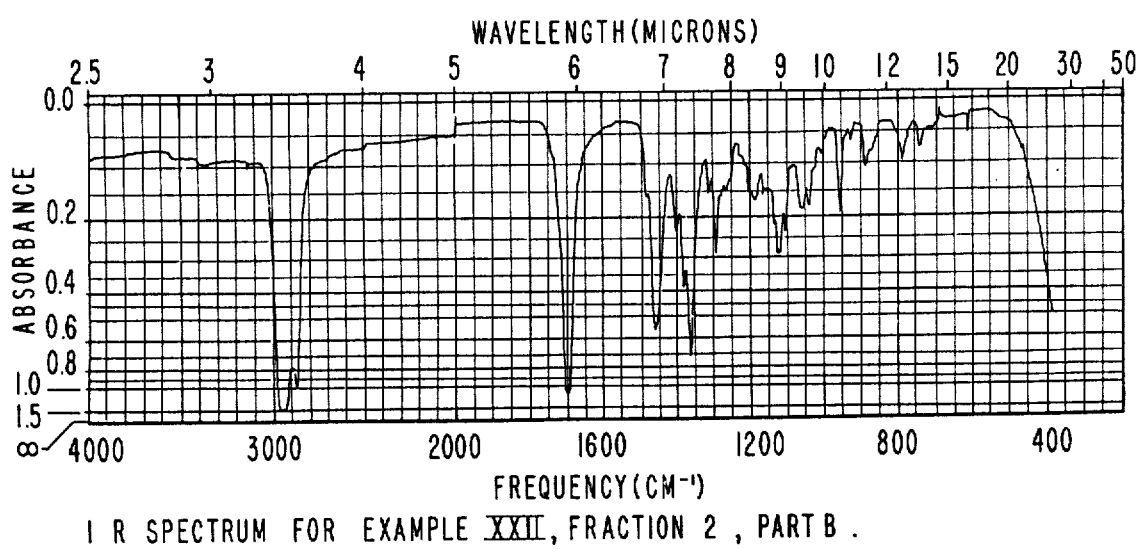

FIG. 28 illustrates the Infrared spectrum for the compound having the structure:

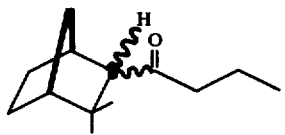

produced according to Part B of Example XXII (fraction 2).

Figure 29:
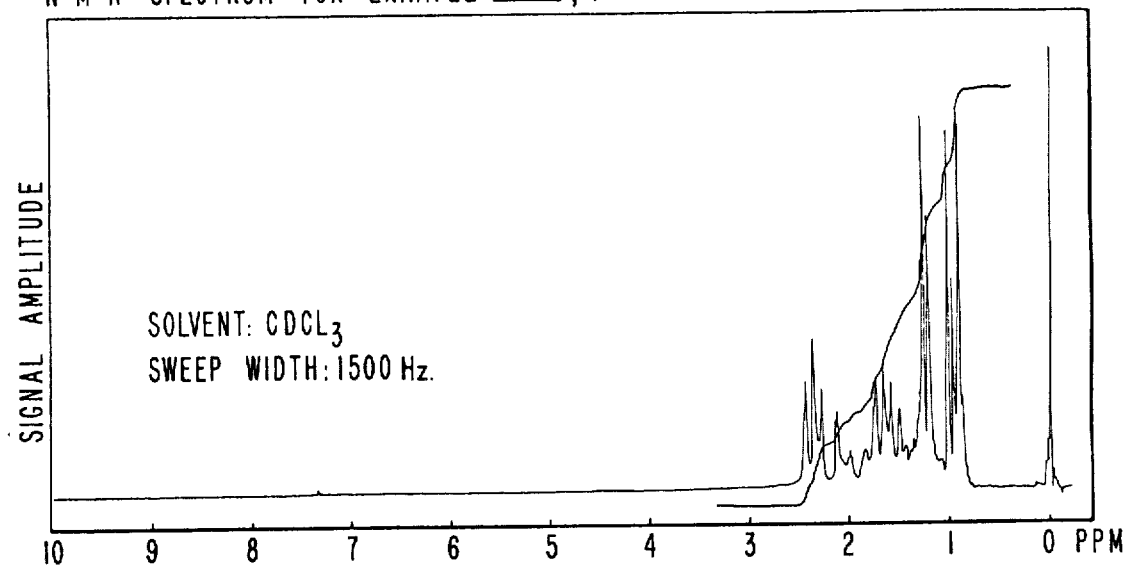

FIG. 29 illustrates the NMR spectrum for fraction 4 of Example XXIII, which is a compound having the structure:

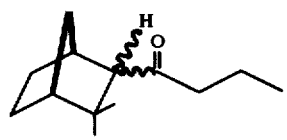

Figure 30:
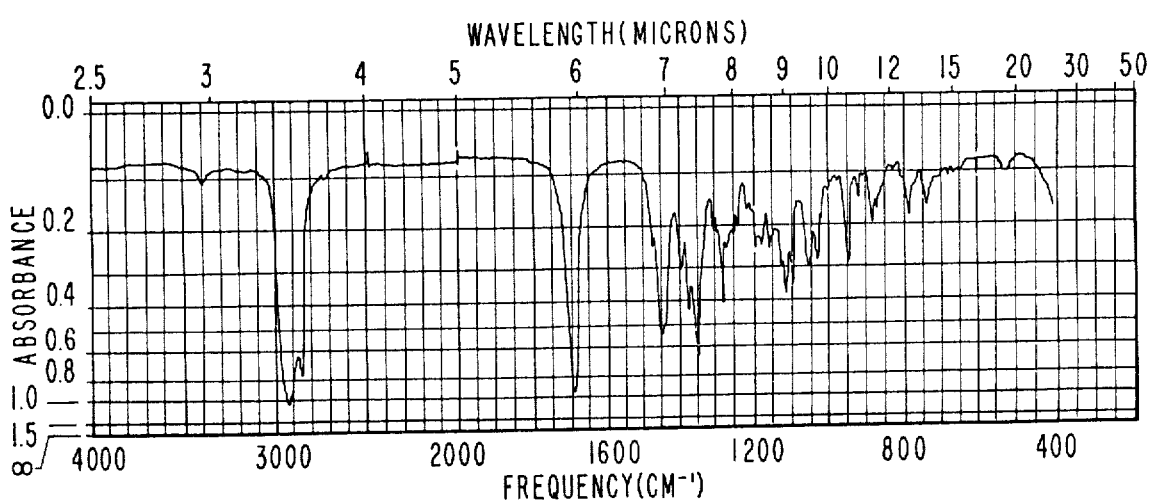

FIG. 30 is the infrared spectrum for fraction 4 of Example XXIII, which is a compound having the structure:

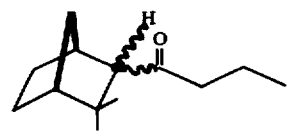

Figure 31:
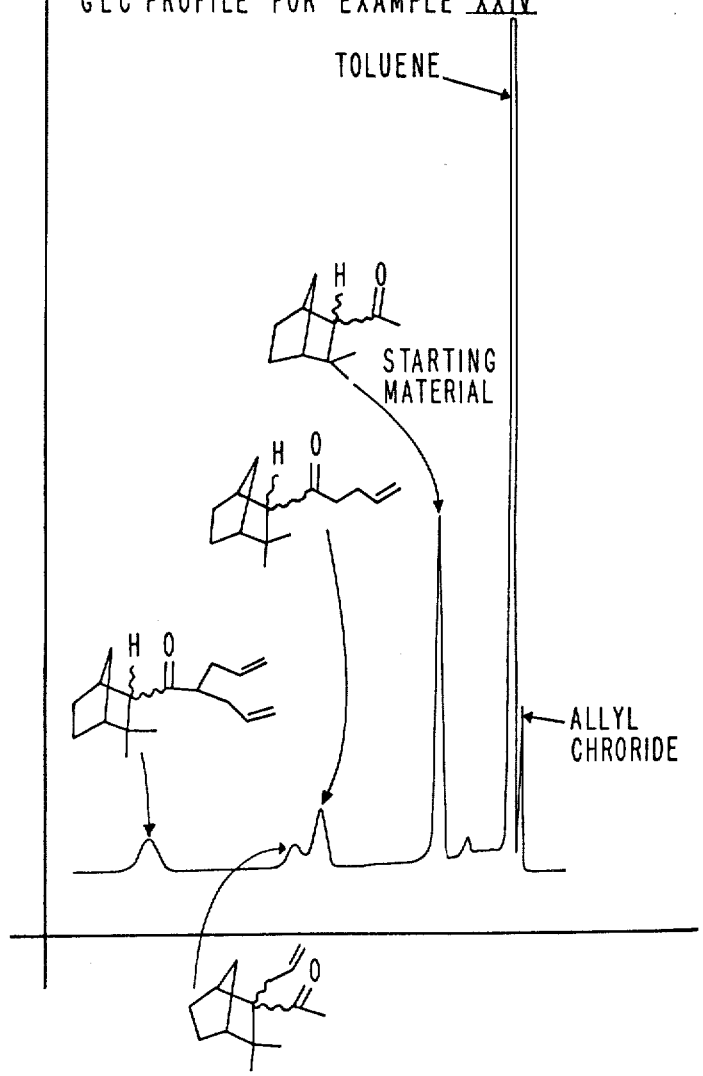

FIG. 31 is the GLC profile for the mixture produced according to the reaction of Example XXIV, which mixture contains compounds having the structures:

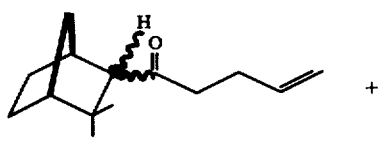

Figure 32:
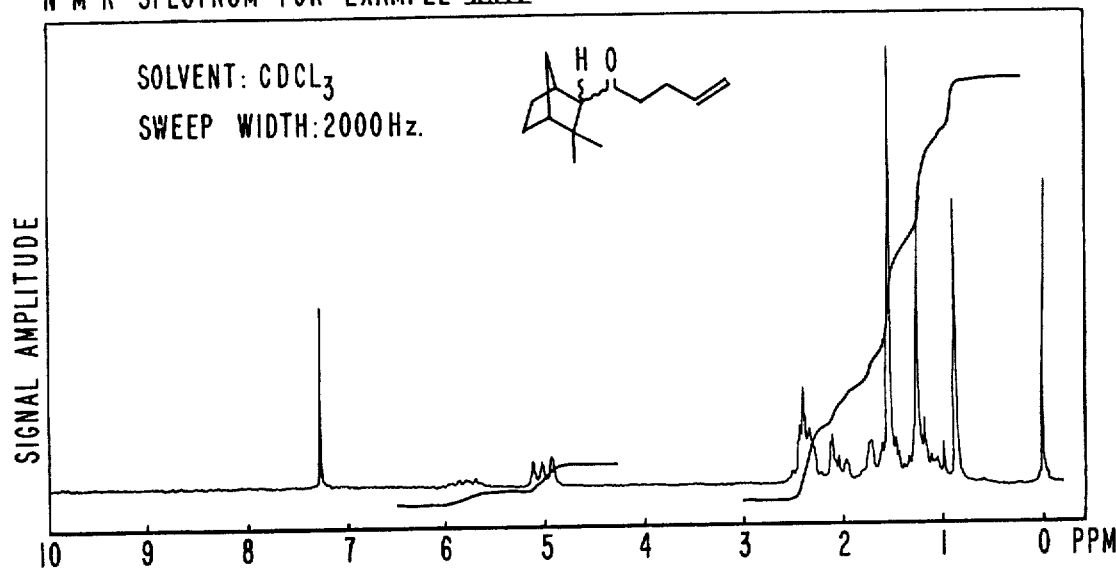
Figure 33:
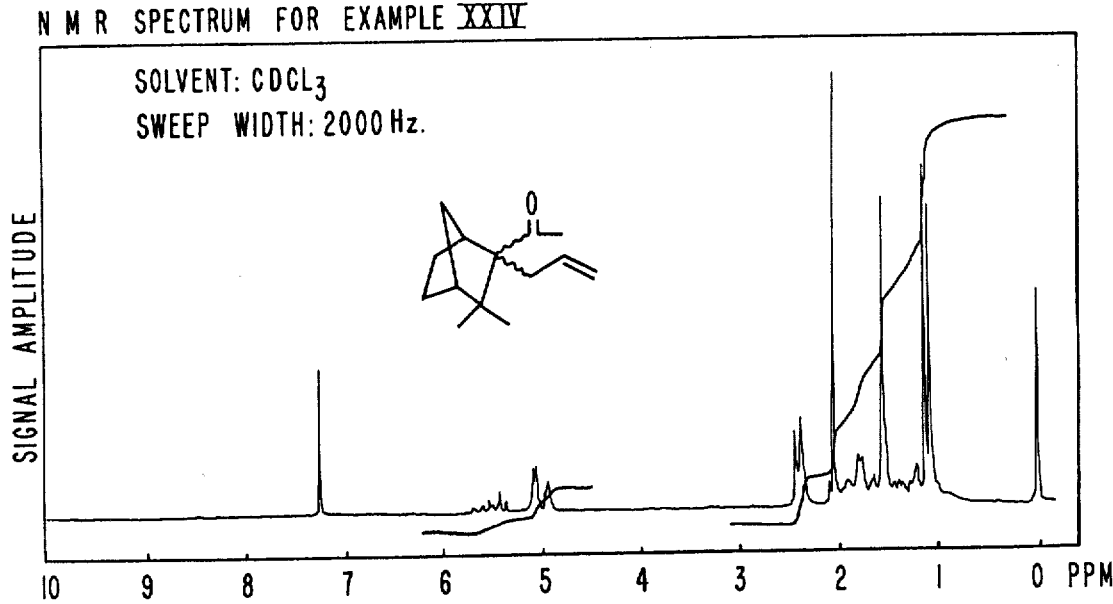

FIG. 32 illustrates the NMR spectrum for the compound having the structure:

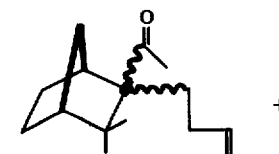

produced according to Example XXIV. FIG. 33 illustrates the NMR spectrum for the compound having the structure:

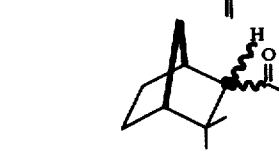

produced according to Example XXIV.

Figure 34:
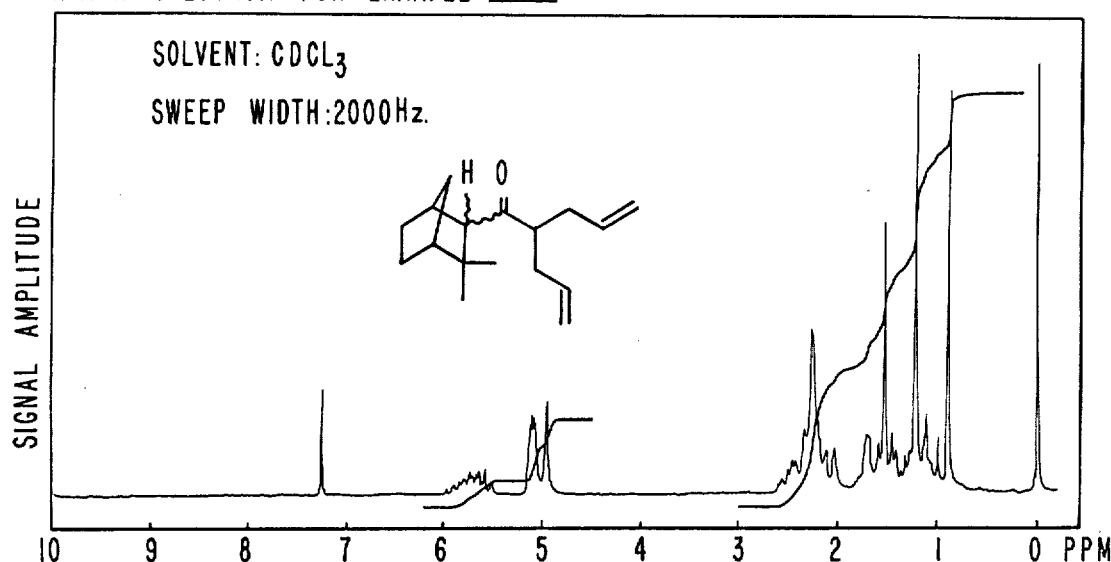

FIG. 34 illustrates the NMR spectrum for the compound having the structure:

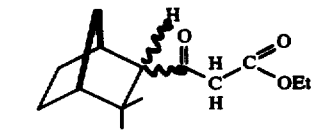

produced according to Example XXIV.

Figure 35:
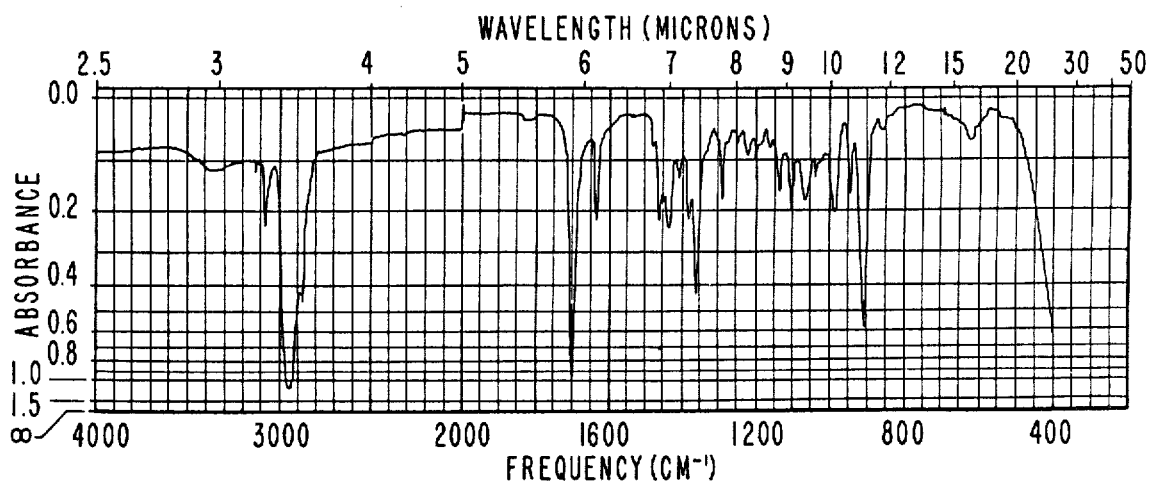

FIG. 35 is the Infrared spectrum for the compound having the structure:

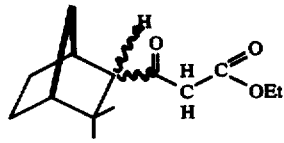

produced according to Example XXIV.

Figure 36:
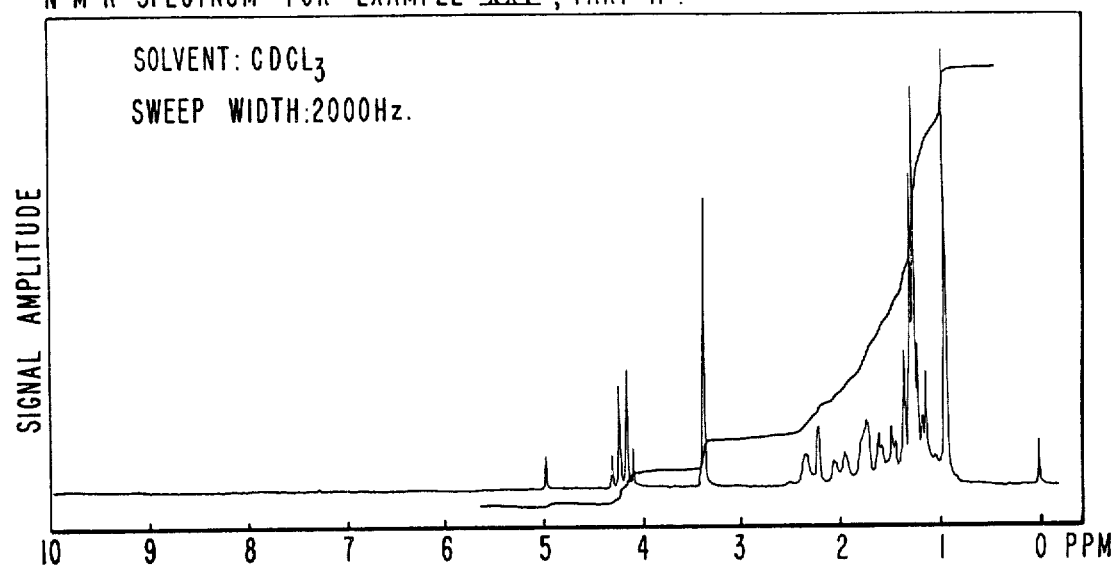

FIG. 36 illustrates the NMR spectrum for the compound produced in Part A of Example XXV, having the structure:

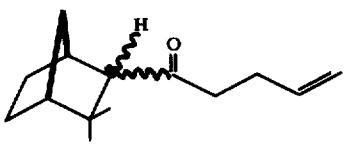

Figure 37:
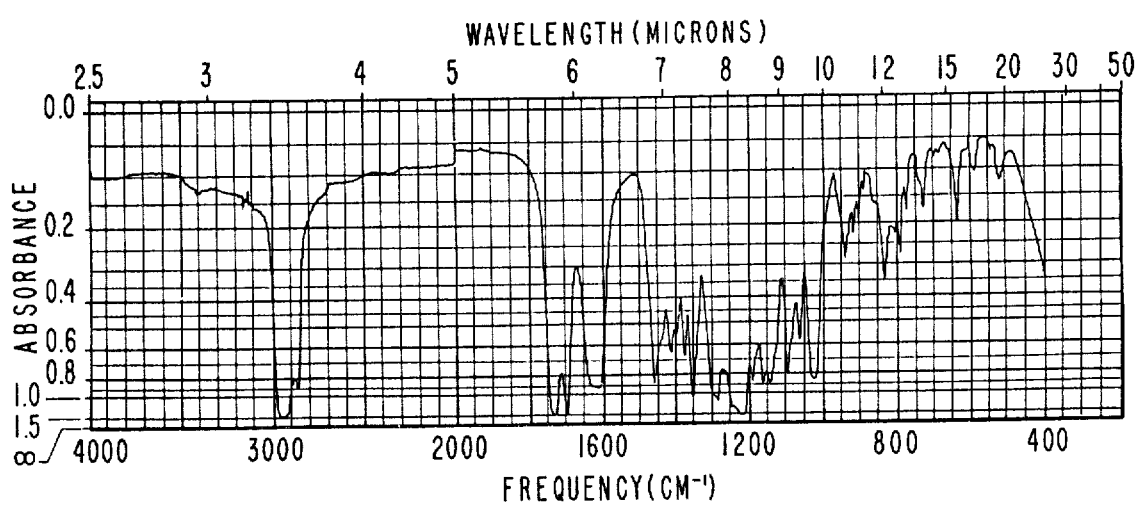

FIG. 37 illustrates the Infrared spectrum for the compound produced in Part A of Example XXV having the structure:

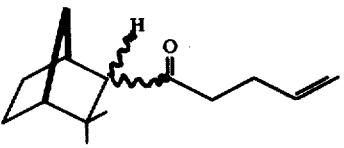

Figure 38:
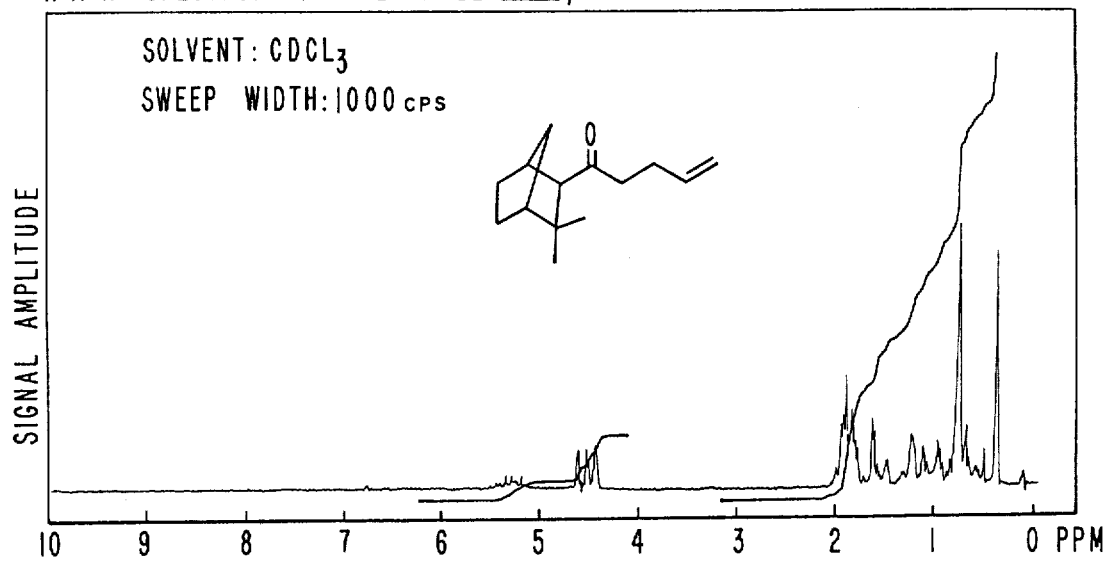
Figure 39:
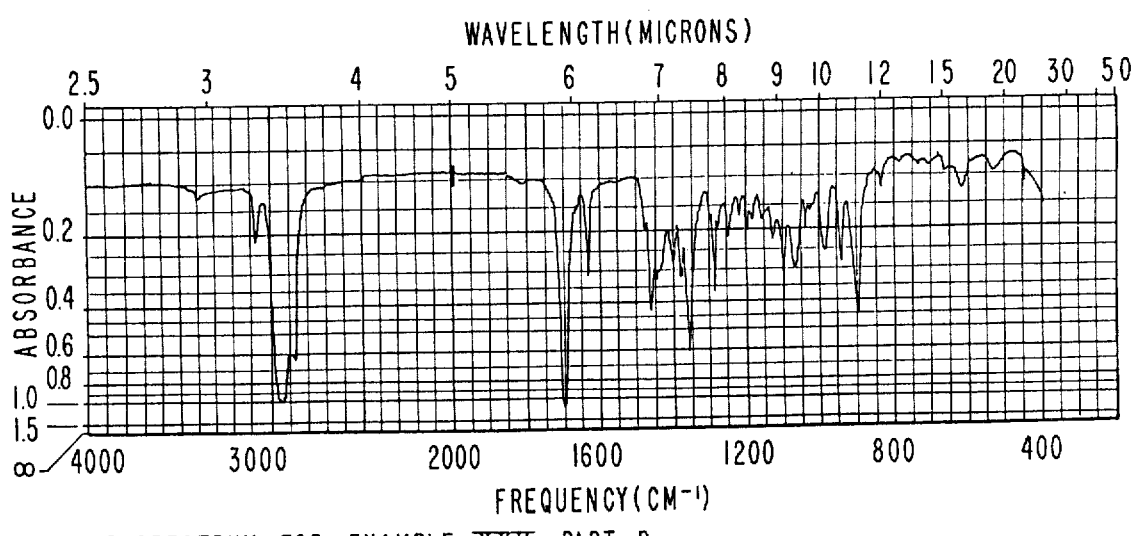

FIG. 38 is the NMR spectrum for the compound produced in Part B of Example XXV having the structure:

FIG. 39 is the Infrared spectrum for the compound produced in Part B of Example XXV having the structure:

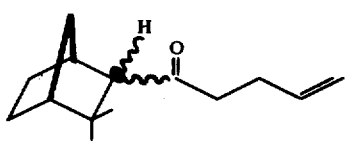

Figure 40:
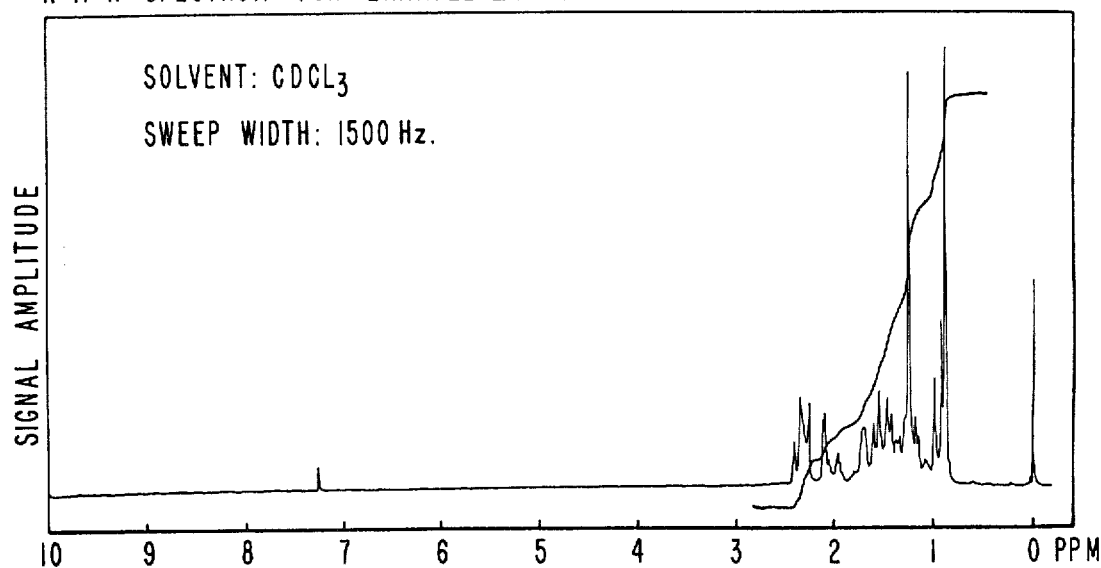

FIG. 40 is the NMR spectrum for the compound having the structure:

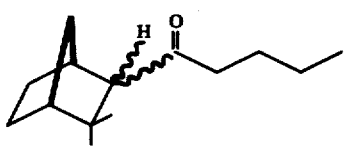

produced according to Example XXVI.

Figure 41:
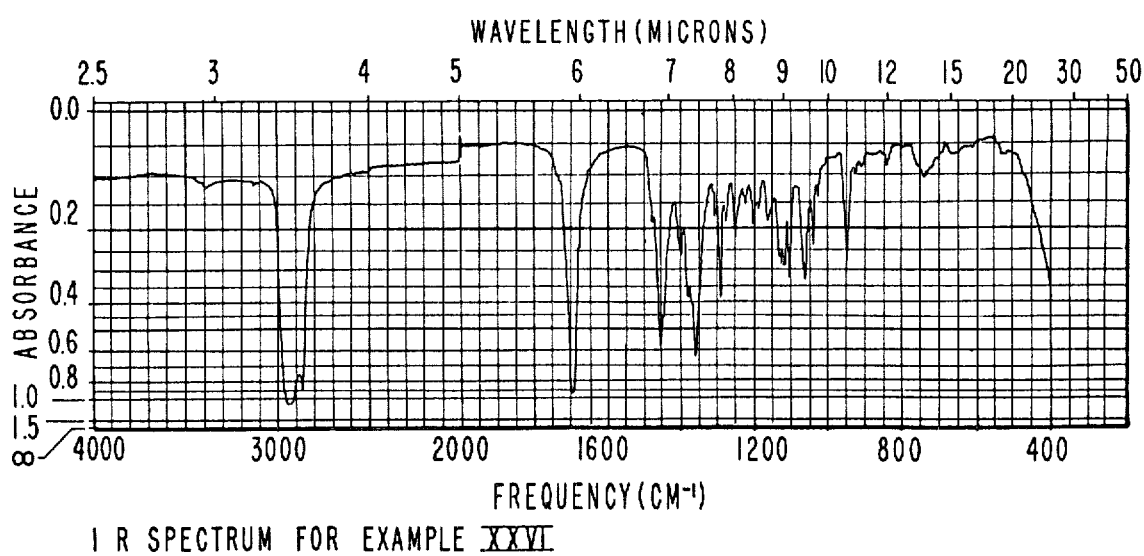

FIG. 41 is the Infrared spectrum for the compound having the structure:

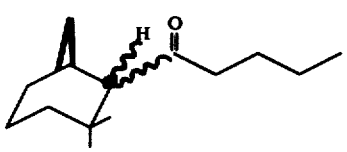

produced according to Example XXVI.

Figure 42:
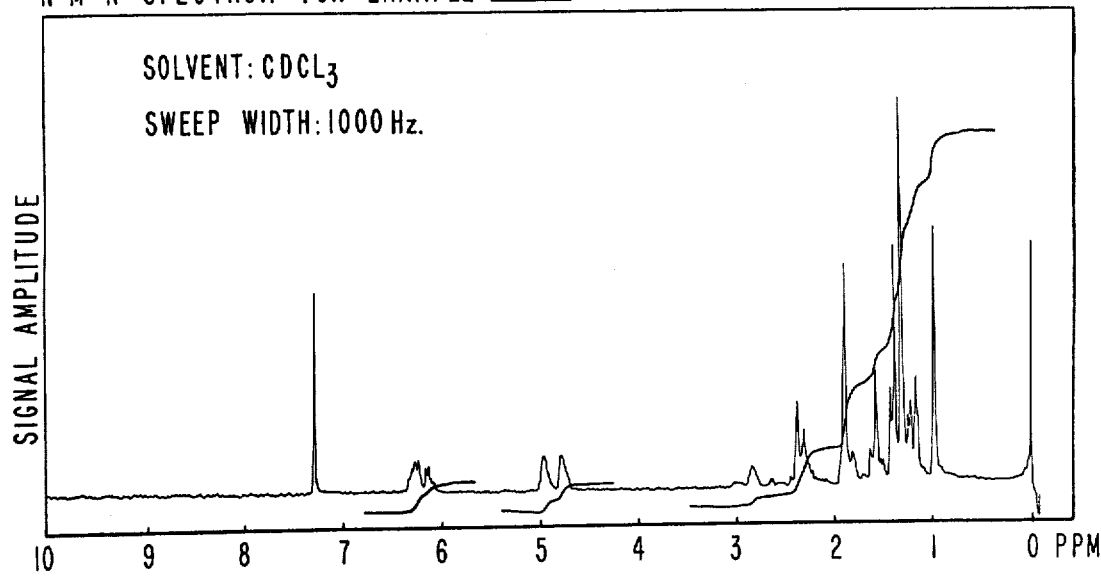

FIG. 42 illustrates the NMR spectrum for the compound having the structure:

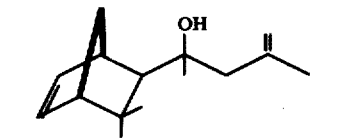

produced according to the process of Example XXVII.

Figure 43:
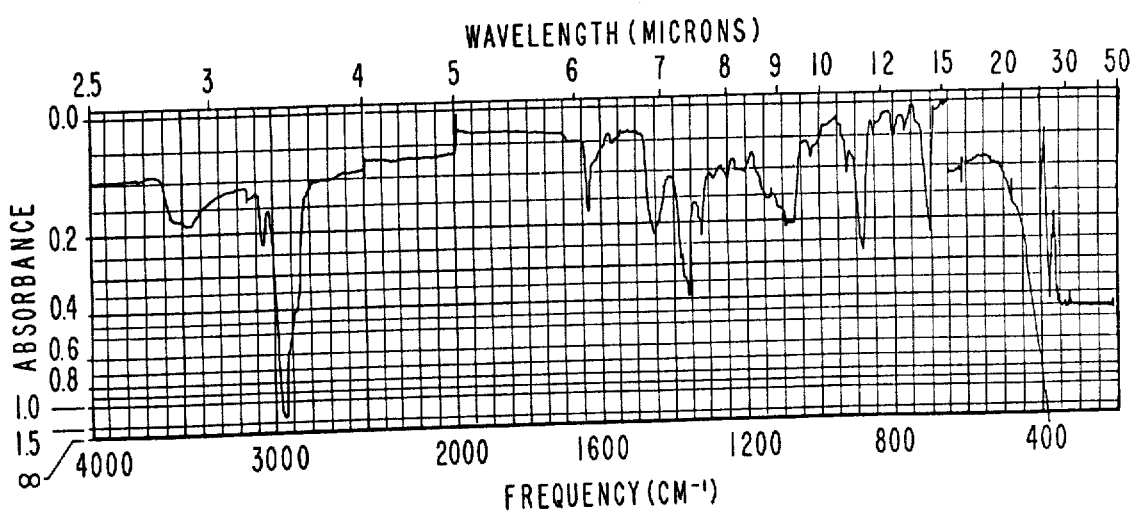

FIG. 43 illustrates the Infrared spectrum for the compound having the structure:

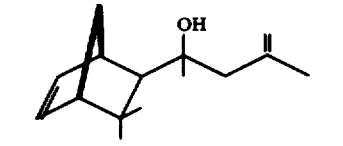

produced according to the process of Example XXVII.

Figure 44:
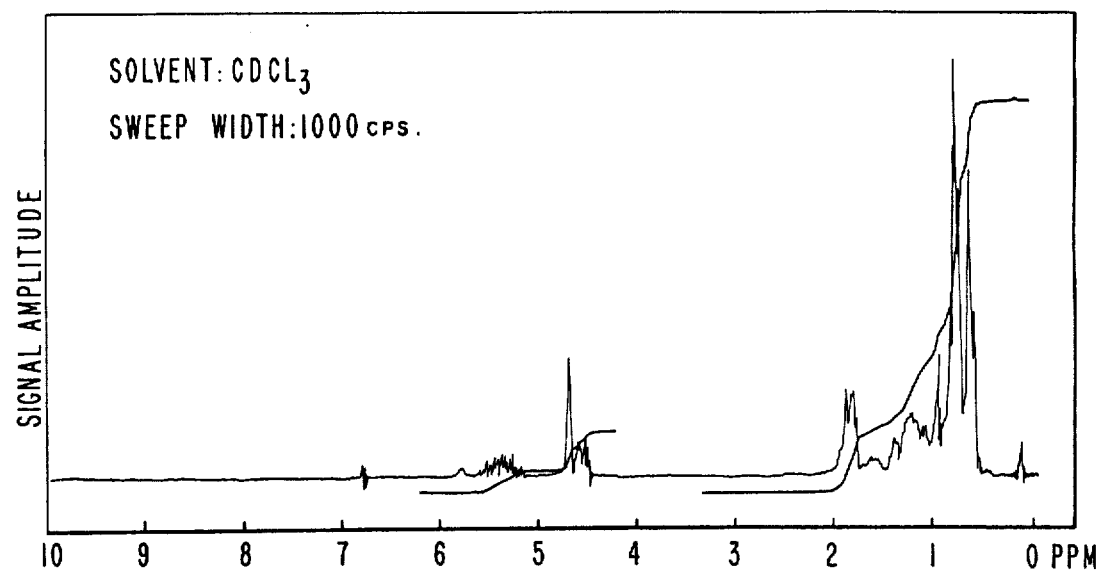

FIG. 44 illustrates the NMR spectrum for the compound having the structure:

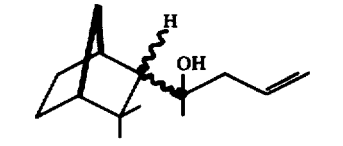

produced according to the process of Example XXVIII.

Figure 45:
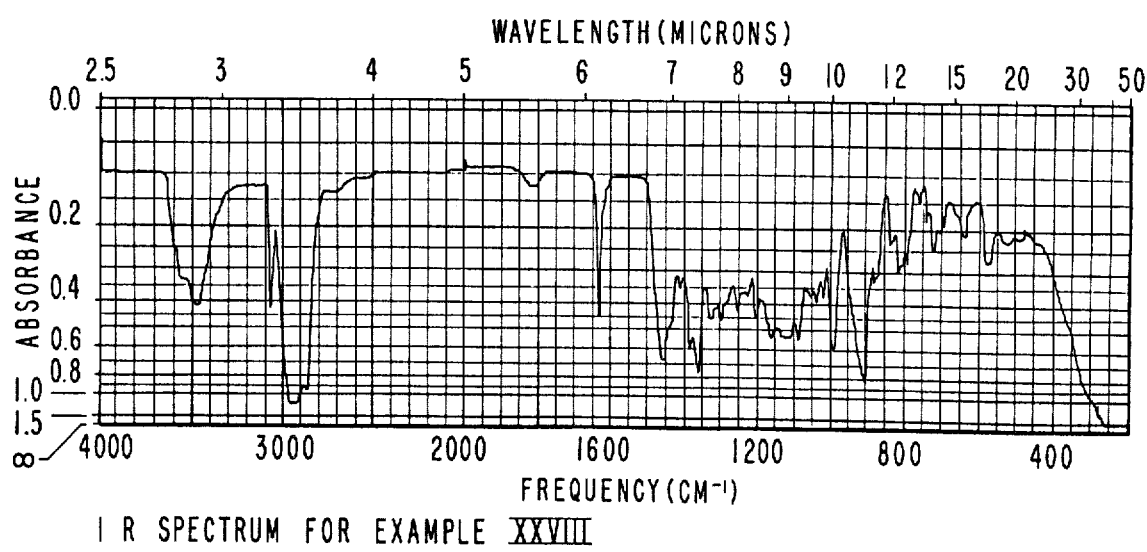

FIG. 45 illustrates the Infrared spectrum for the compound having the structure:

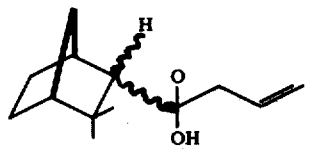

produced according to the process of Example XXVIII.

Figure 46:
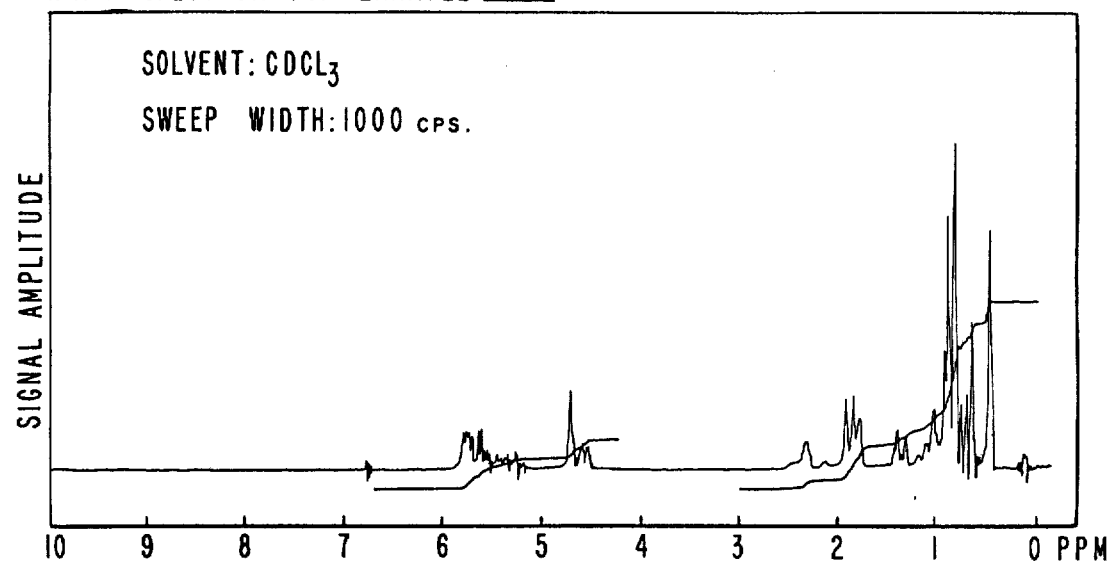

FIG. 46 illustrates the NMR spectrum for the compound having the structure:

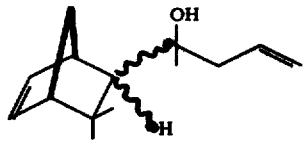

produced according to the process of Example XXIX.

Figure 47:
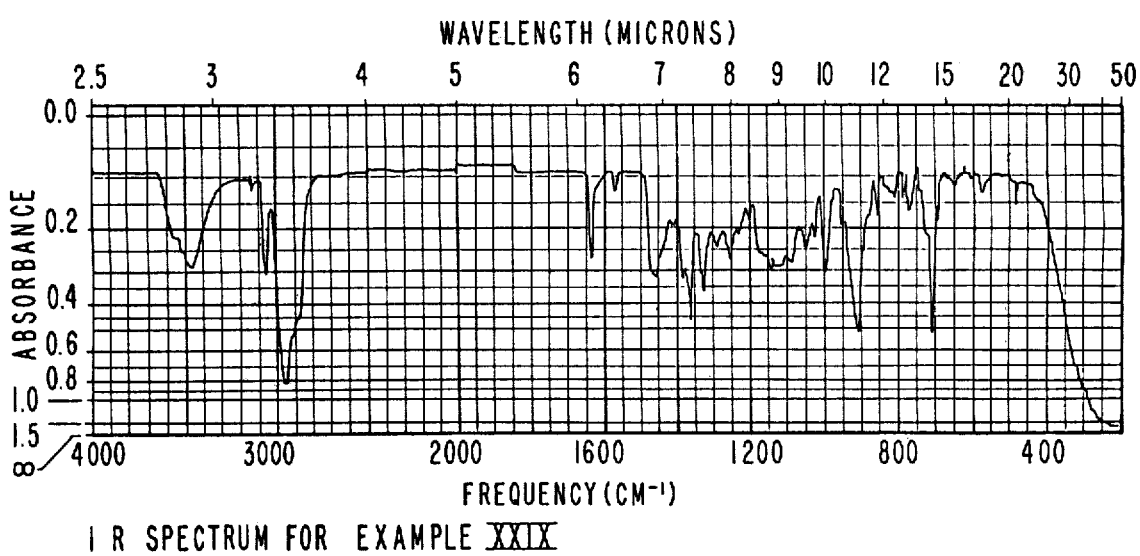

FIG. 47 is the Infrared spectrum for the compound having the structure:

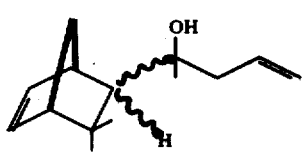

produced according to the process of Example XXIX.

Figure 48:
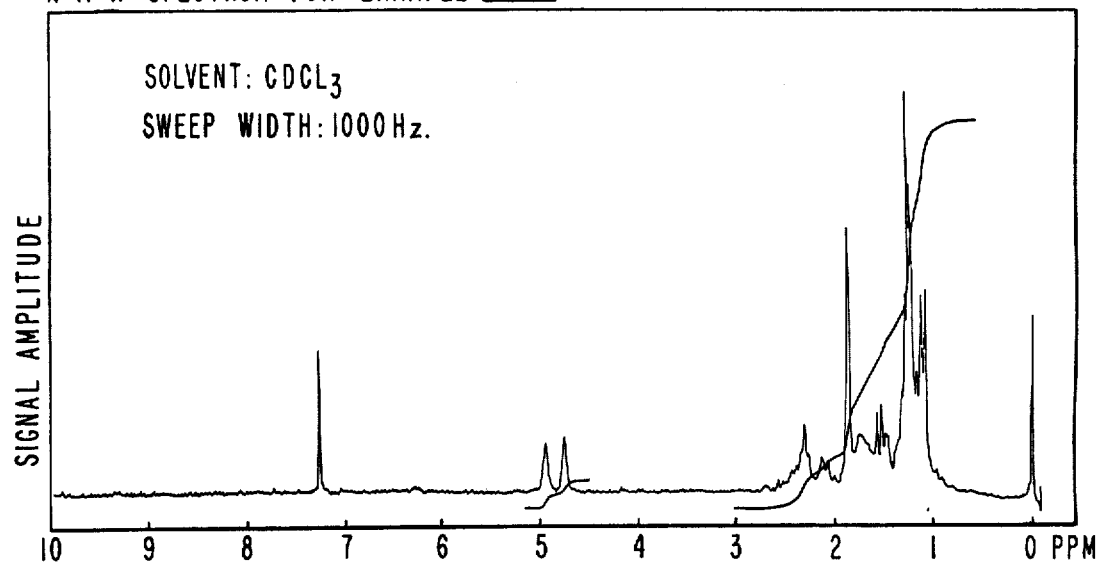

FIG. 48 is the NMR spectrum for the compound having the structure:

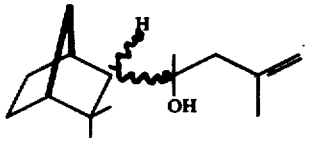

produced according to the process of Example XXX.

Figure 49:
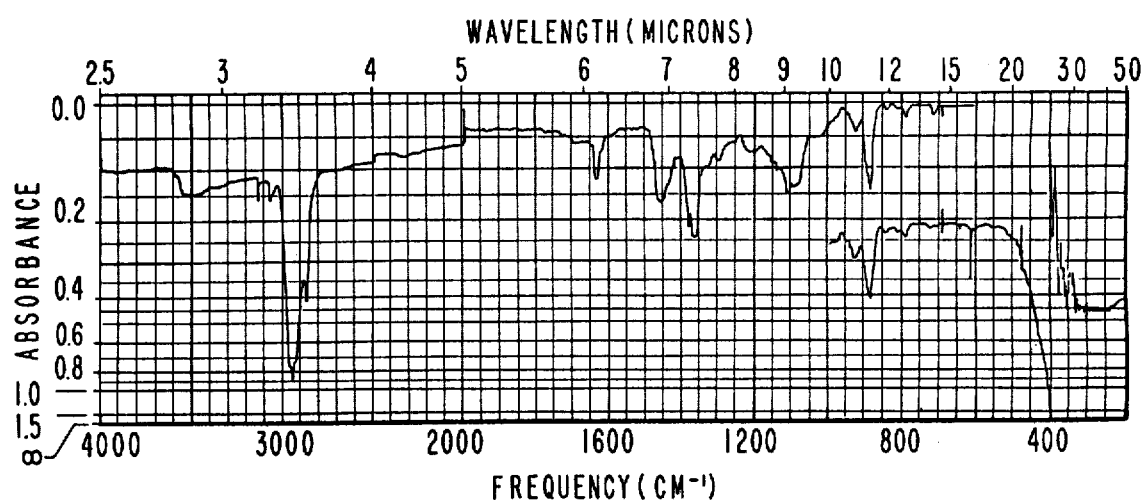

FIG. 49 is the Infrared spectrum for the compound having the structure:

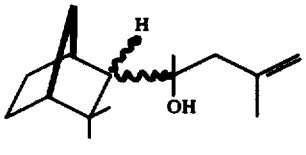

produced according to the process of Example XXX.

Figure 50:
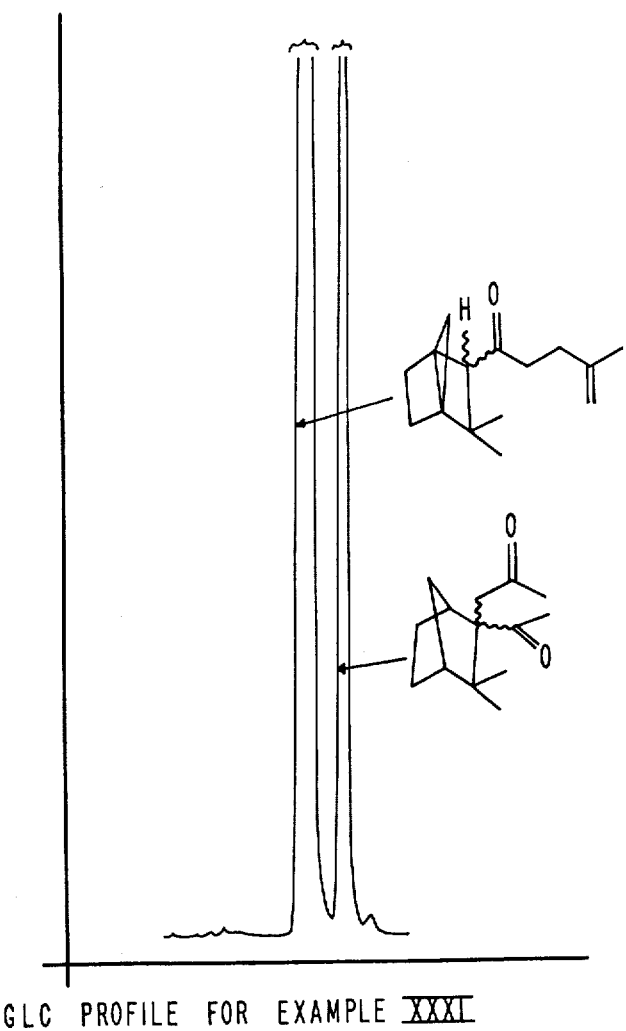

FIG. 50 is the GLC profile for the mixture (i) of the reaction product of Example XXXI, b.p. 100°–111° C/0.9 mm Hg.

FIG. 51 is the NMR spectrum for the compound having the structure:

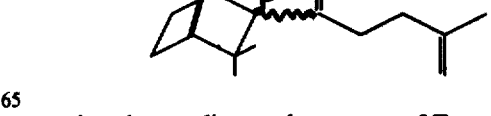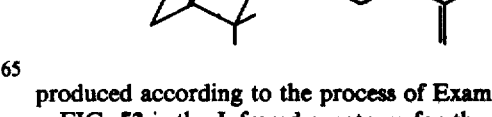

produced according to the process of Example XXXI.

FIG. 52 is the Infrared spectrum for the compound having the structure:

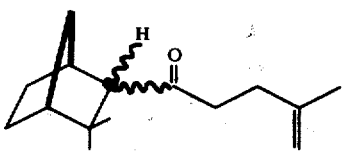

produced according to the process of Example XXXI.

Figure 53:
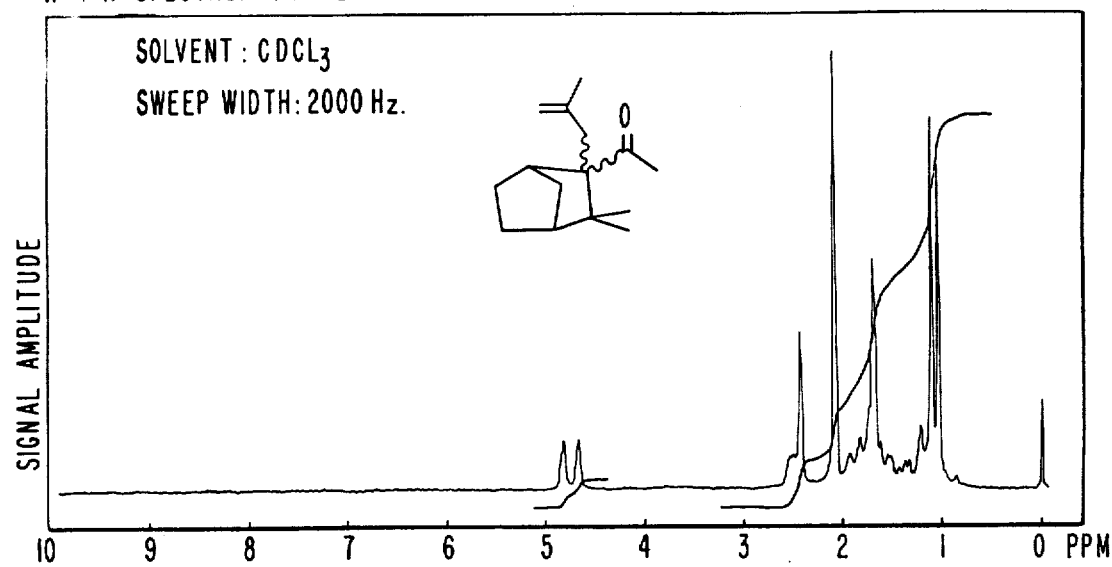

FIG. 53 is the NMR spectrum for the compound having the structure:

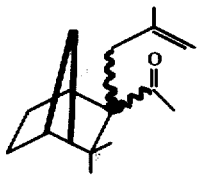

produced according to the process of Example XXXI.

Figure 54:
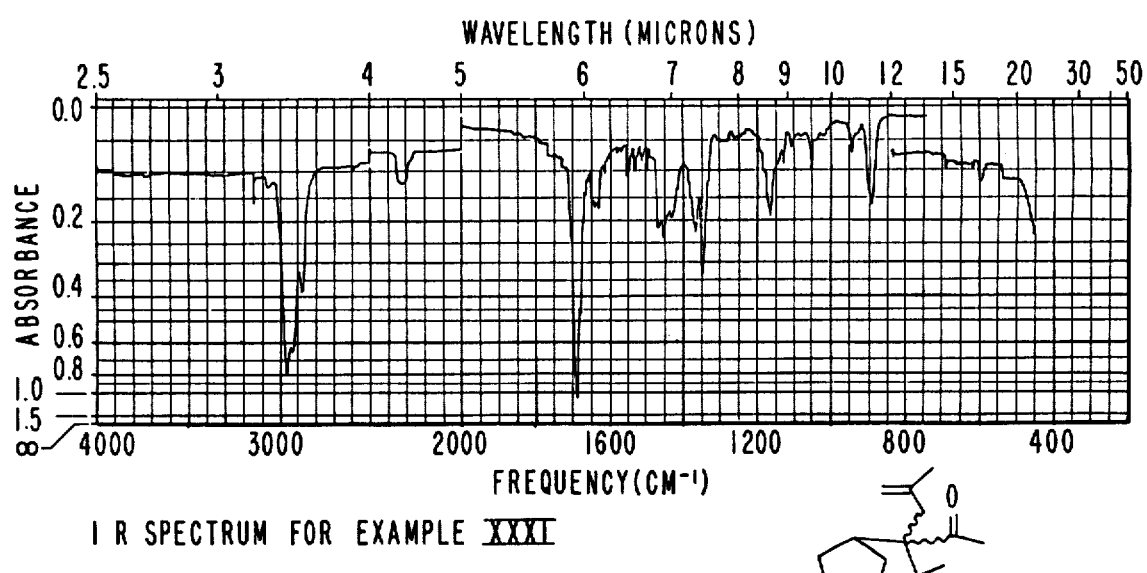

FIG. 54 is the Infrared spectrum for the compound having the structure:

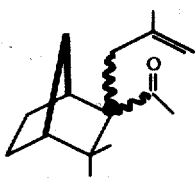

produced according to the process of Example XXXI.

FIG. 55 is the NMR spectrum for the compound having the structure:

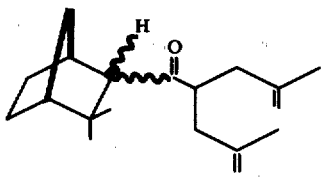

produced according to the process of Example XXXI.

FIG. 56 is the Infrared spectrum for the compound having the structure:

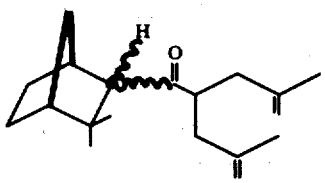

produced according to the process of Example XXXI.

FIG. 57, FIG. 58, FIG. 59 and FIG. 60 represent GC-MS profiles for compounds produced according to the process of Example LXI.

THE INVENTION

It has now been discovered that novel solid and liquid foodstuff, chewing gum, medicinal product and toothpaste compositions and flavoring compositions therefor having fruity, piney/green, winey, fruity-estery, cedarwood, floral, woody, balsam tree resin-like, sweet, fruity berry, incense, minty, balsam, blueberry, piney, green fruity and/or pine needle/green aromas with piney, eugenol/clove, spicey, fruity, winey, sweet, banana-like, estery, balsam tree resin-like, woody, incense, warm tea-like, floral, cedarwood, rosey, berry, tea, astringent, bitter, camphoraceous green/earthy, green, minty, earthy, red beet-like, balsam natural-like, balsam resin-like, rum-like and/or blueberry tastes; as well as novel tobacco and tobacco flavoring compositions having sweet, woody, fruity, cooling aroma prior to smoking and sweet, natural tobacco-like smoke flavor characteristics in the mainstream on smoking; as well as novel perfume compositions, colognes and perfumed articles having intense and pleasant, twiggy, melony, sweet, woody, fruity, spicey (nutmeg, pepper), herbaceous, fir-balsam, thujone-like, cedar leaf, camphoraceous, musty, minty, fresh cut pine/spruce, artemesia, natural-like, cresylic, borneol aromas with strong armoise-like undertones, may be provided by the utilization of one or more substituted norbornane derivatives having the generic structure:

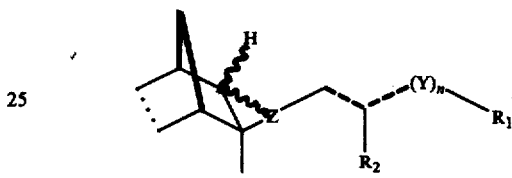

wherein each of the dashed lines represents a carbon-carbon single bond or a carbon-carbon double bond with the proviso that at least one of the dashed lines is a carbon-carbon single bond; wherein $n$ is 0 or 1 with the proviso that $n$ is 1 when both dashed lines are single bonds and $n$ is 0 when one of the dashed lines is a double bond; wherein $R_1$ and $R_2$ are each the same or different hydrogen or lower alkyl; wherein Y is:

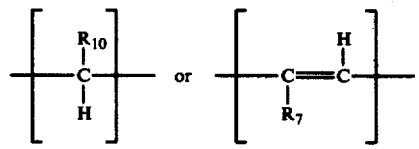

wherein Z is one of the moieties:

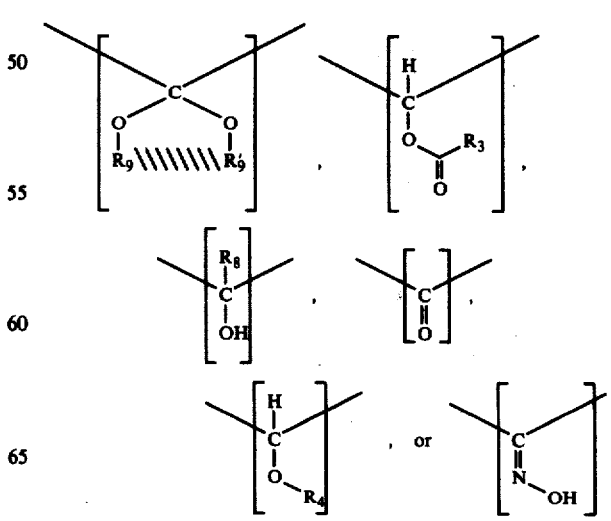

wherein R₃ and R₄ are each alkyl; wherein $R_7$, $R_8$ and $R_{10}$ are each the same or different hydrogen or lower alkyl; wherein $R_9$ and $R_9'$ taken separately are the same or different lower alkyl, or taken together is lower alkylene; wherein the dotted line represents a carbon-carbon single bond or a carbon-carbon double bond; and wherein each of the wavy lines represents, in the alternative, exo or endo isomers, in foodstuffs, chewing gums, toothpastes, medicinal products, perfume compositions, perfumed articles, colognes and tobaccos as well as tobacco substitutes.

Unless otherwise specified, representations herein of carbon-carbon double bonds are intended to indicate a "cis" isomer, a "trans" isomer, or a mixture of "cis" and "trans" isomers with respect to that carbon-carbon double bond.

The novel substituted norbornane derivatives of our invention useful as indicated supra, may be produced, preferably, by one of several processes:

(1) A process comprising the step of reacting one or a mixture of compounds having the structures:

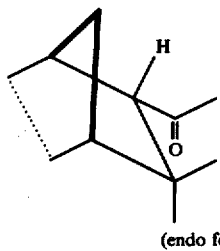 or 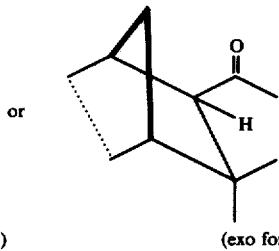

(endo form)   (exo form)

wherein the dotted line represents a carbon-carbon single bond or a carbon-carbon double bond with an aldehyde having the structure:

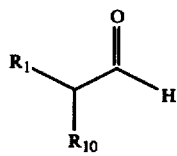

wherein $R_1$ and $R_{10}$ are the same or different alkyl or hydrogen as defined above, thereby forming a mixture of compounds having the two structures:

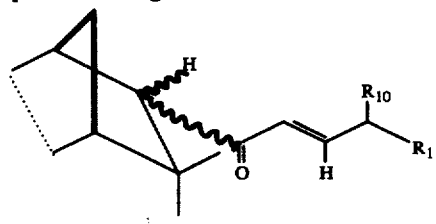

and

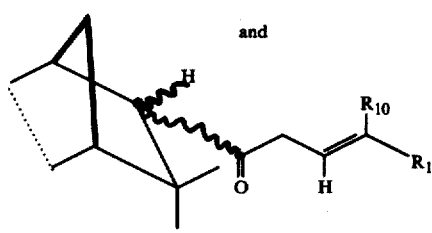

utilizing the resulting compounds for their organoleptic properties or further reacting the resulting compounds, either with a Grignard reagent, $R_8MgX$, or an organolithium reagent, $R_8Li$, (wherein $R_8$ is lower alkyl, e.g., methyl, ethyl, 1-propyl-2-propyl, 1-butyl, 2-butyl, 2-methyl-1-butyl or 2-methyl-2-butyl) followed by hydrolysis to form the tertiary alcohol having one of the structures:

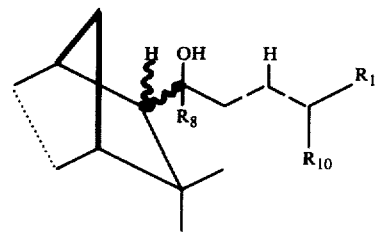

or by reduction of the carbonyl group and/or one (or more) of the carbon-carbon double bond(s) to form the secondary alcohol or ketone having one of the structures:

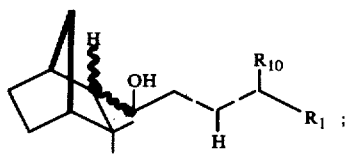

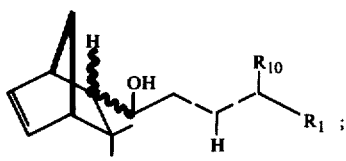

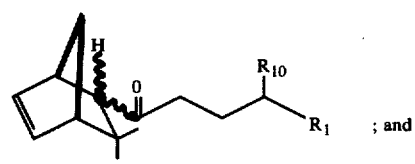

; and

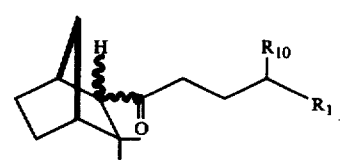

or by re-arranging the carbon-carbon double bond in the side chain thereby forming compounds of the structure:

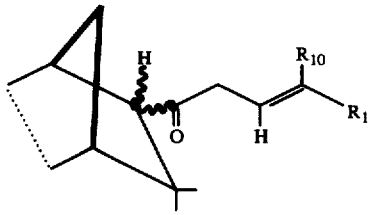

wherein $R_1$ and $R_{10}$ are the same or different hydrogen or lower alkyl, wherein the dotted line represents a carbon-carbon single bond or a carbon-carbon double bond, and wherein each of the dashed lines represent a carbon-carbon single bond or a carbon-carbon double bond with the proviso that at least one of the dashed lines is a carbon-carbon single bond.

(2) Oxidizing camphene to form camphene oxide having the structure:

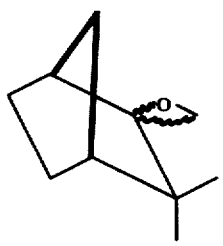

and then rearranging said camphene oxide to the aldehyde (3,3-dimethylnorbornane-2-carboxaldehyde) having the structure:

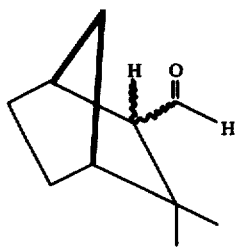

and then reacting the aldehyde with a Grignard reagent having the structure:

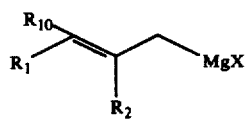

or an organolithium reagent having the structure:

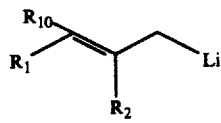

wherein X is one of the halogen atoms, chlorine, bromine or iodine, thereby forming an organo-metallic compound having the structure:

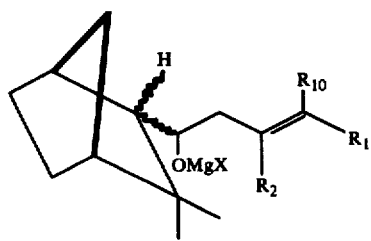

or

-continued

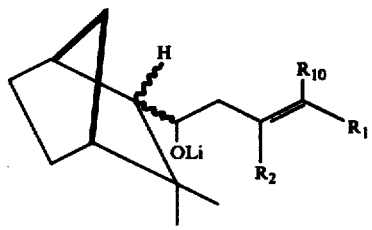

and then hydrolyzing the said organometallic compound to form the corresponding alcohol having the structure:

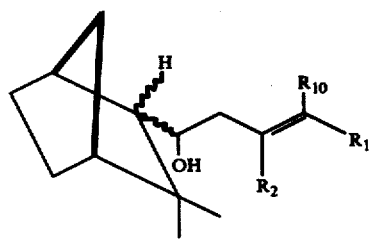

and then using said alcohol for its organoleptic properties or oxidizing or reducing said alcohol to form either the unsaturated ketone, or the saturated alcohol, as is set forth in the first of these processes (process (1)), which ketone and alcohols have the structures, respectively,

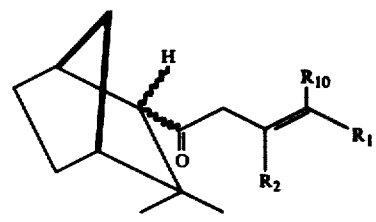

and

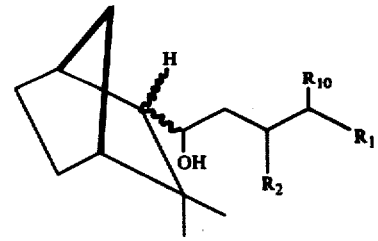

and then using the resulting products for their organoleptic properties or, in the case of compounds having unsaturation in the side chain, rearranging the double bond to form a compound having the structure:

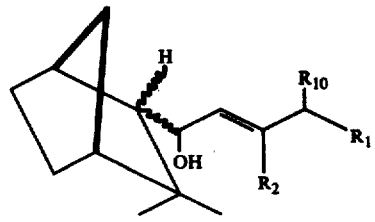

or

-continued

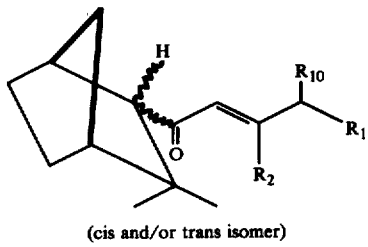

(cis and/or trans isomer)

(3) Reacting an aldehyde having the structure:

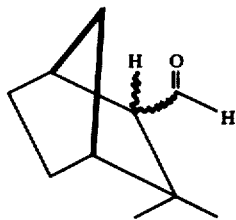

with a Grignard reagent having the structure:

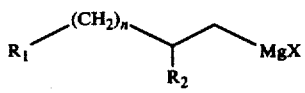

or an organolithium reagent having the structure:

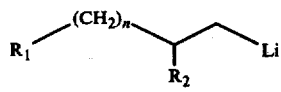

wherein n is 0 or 1 thereby forming an organo-metallic compound having the structure:

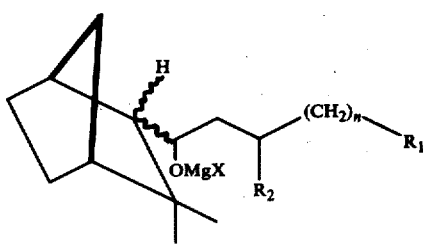

or

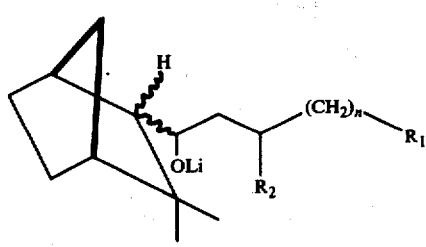

then hydrolyzing the resulting organometallic compound thereby forming the saturated alcohol having the structure:

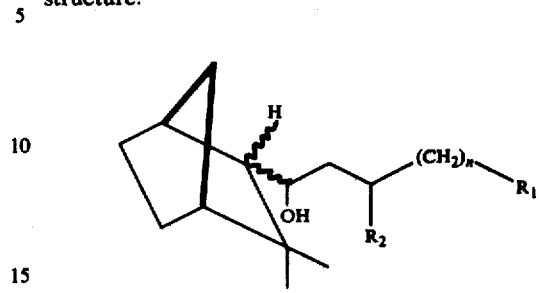

This alcohol can then be used as such for its organoleptic properties or it can be oxidized to form the ketone having the structure:

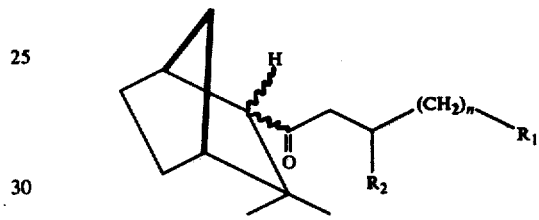

or it can be esterified with an esterification agent to form an ester having the structure:

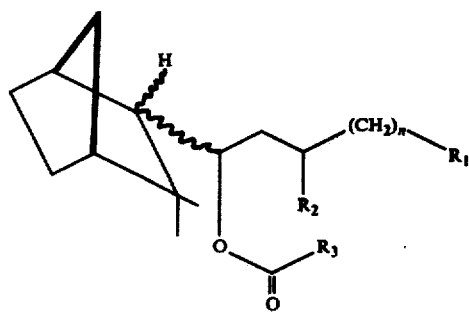

wherein $R_1$, $R_2$ and $R_3$ are the same or different hydrogen or alkyl and n is 0 or 1.

(4) Adding a compound, 2-acetyl-3,3-dimethyl-5-norbornene having the structure:

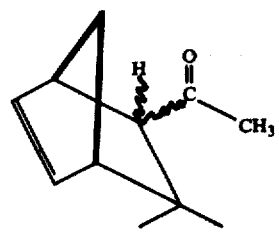

to acetaldehyde according to the reaction sequence:

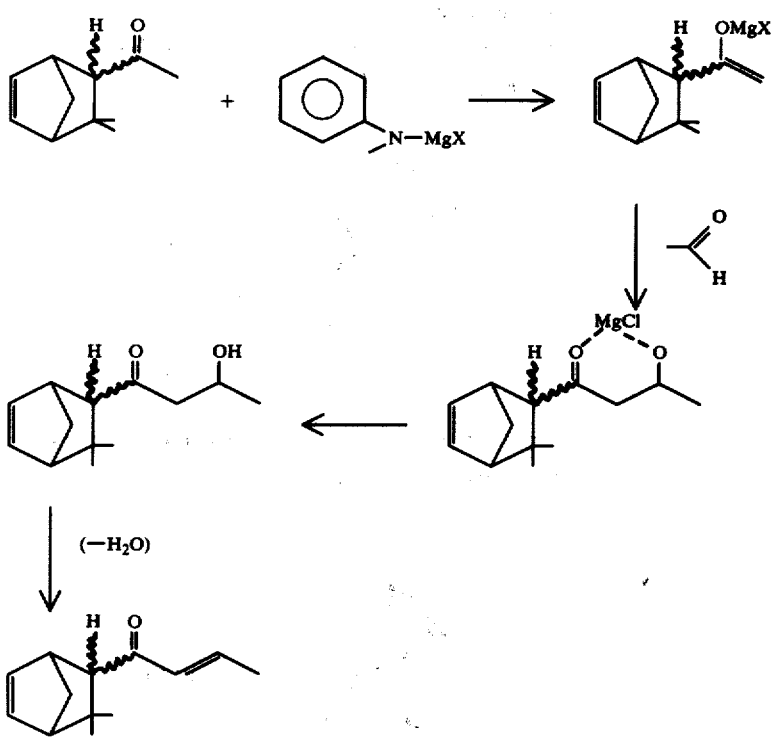

(wherein X is halogen, e.g., chloro, bromo or iodo) whereby a compound having the structure:

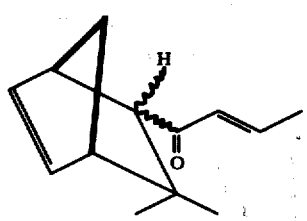

is formed.

(5) Adding 2-acetyl-3,3-dimethylnorbornane having the structure:

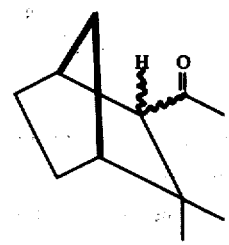

to an allylic halide having the structure:

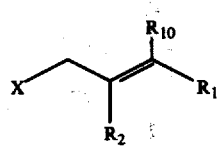

wherein either or both of $R_1$, $R_2$ and $R_{10}$ is hydrogen or lower alkyl and X is one of the halogen atoms, chlorine, bromine or iodine, in the presence of a base such as an alkali metal hydroxide and a "phase transfer agent", or in the presence of a base such as an alkali metal hydride in the presence of a "phase transfer agent" in order to form the compounds having the structures:

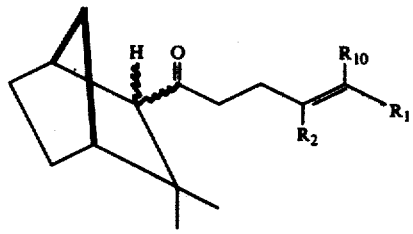

wherein any of $R_1$, $R_2$, $R_{10}$, $R_1'$, $R_2'$ and $R_{10}'$ are the same or different hydrogen or lower alkyl; using the resulting mixture "as is" for its organoleptic properties or separating the resulting mixture into its component compounds and using the resulting compounds for their organoleptic properties or further reacting the resulting mixture or each of the resulting compounds as by rearrangement of a carbon-carbon double bond and/or by reduction of the keto group to form a hydroxyl group or reduction of one or more carbon-carbon double bonds using hydrogen;

(6) Reacting 2-acetyl-3,3-dimethylnorbornane or 2-acetyl-3,3-dimethyl-5-norbornene with a dialkyl carbonate to form a ketocarboxylic acid ester, forming the enolate of the ketocarboxylic acid ester using a base, and then reacting the resulting enolate with an allyl halide to form a substituted ketocarboxylic acid ester and saponifying the resulting substituted ketocarboxylic acid ester to form a salt of a ketocarboxylic acid and then acidifying the salt of the ketocarboxylic acid and decarboxylating the ketocarboxylic acid according to the following reaction sequence:

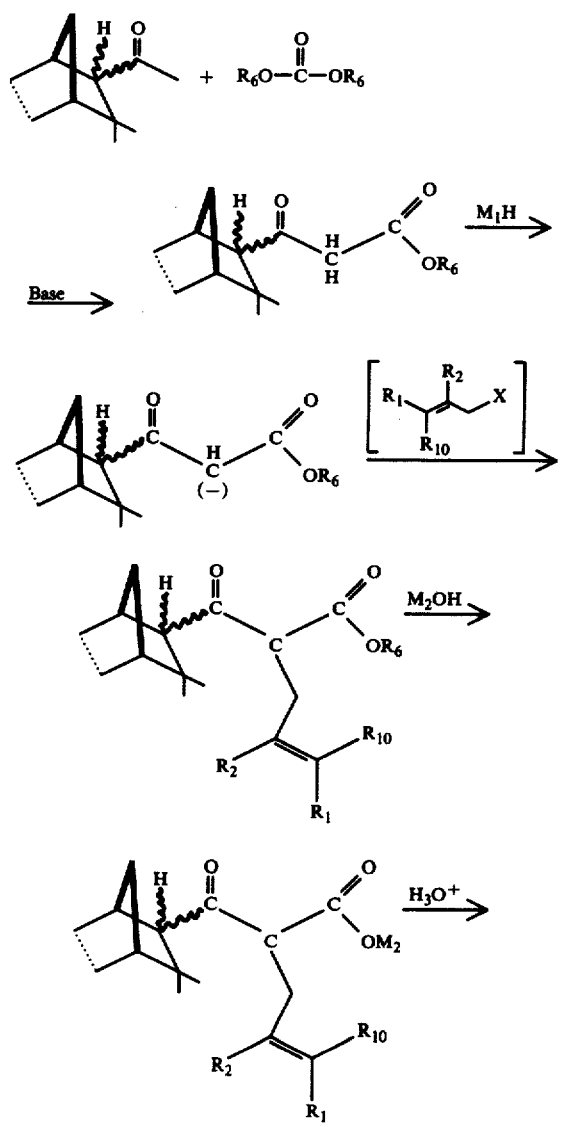

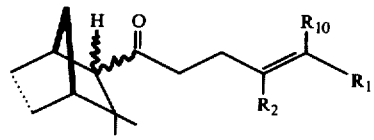

wherein $R_6$ is lower alkyl and $R_1$ and $R_2$ are the same or different hydrogen or lower alkyl, $M_1$ and $M_2$ are the same or different alkali metal; using the resulting ketone "as is" for its organoleptic properties or further reacting the resulting ketone as indicated in any of Processes 1–5, inclusive;

(7) Reacting 2-acetyl-3,3-dimethylnorbornane or 2-acyl-3,3-dimethyl-5-norbornene having the generic structure:

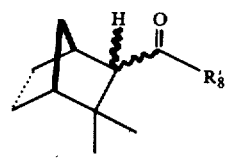

wherein $R_8'$ is lower alkyl, with an allylic Grignard reagent having the structure:

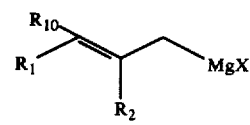

or an allylic lithium reagent having the structure:

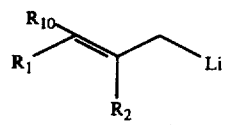

wherein X is one of the halogen atoms, chlorine, bromine or iodine, thereby forming an organo-metallic compound having the structure:

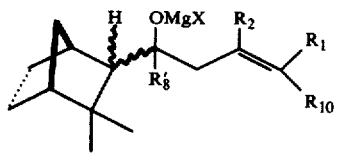

or

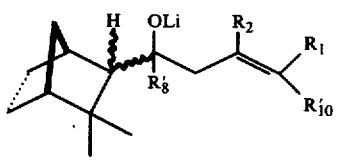

and then hydrolyzing the organometallic compound using aqueous mineral acid to form the corresponding tertiary alcohol having the generic structure:

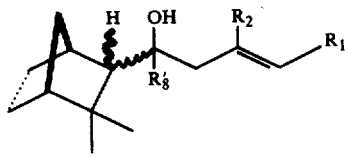

Each of the foregoing processes is described below in more detail.

Process 1

The reaction of the aldehyde having the structure:

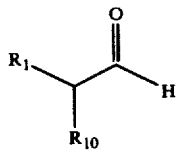

with 2-acetyl-3,3-dimethylnorbornane or 2-acetyl-3,3-dimethyl-5-norbornene, preferably takes place in the presence of either a base such as an alkali metal hydroxide (e.g., NaOH) or a mixed catalyst containing boron oxide and boric acid whereby an alkenoyl norbornane or norbornene derivative is formed having the structure:

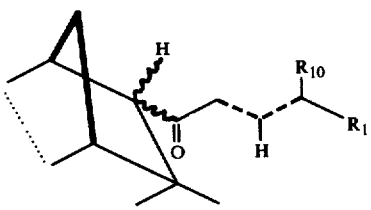

wherein one of the dashed lines is a carbon-carbon double bond and the other is a single bond and the dotted line represents a carbon-carbon single bond or double bond; wherein $R_1$ and $R_{10}$ are the same or different hydrogen or lower alkyl. Thus, for example, reaction of acetaldehyde with 2-acetyl-3,3-dimethylnorbornane produces 2-(trans-2-butenoyl)-3,3-dimethylnorbornane. It is preferred to carry out this reaction at a temperature in the range of from 120° C up to 200° C for a period of from 3 up to 10 hours. It is preferred that the mole ratio of 2-acetyl-3,3-dimethylnorbornane (or norbornene) aldehyde be 1:1 or slightly greater than 1:1. When using an alkali metal hydroxide catalyst, it is preferred that the mole ratio of base:acetyl norbornane or norbornene be from 1:1 up to 20:1. When using the mixed catalyst, boron oxide:boric acid, it is preferred that the mole ratio of aldehyde:boron oxide be approximately 2:1 or greater than 2:1 and it is preferred that the mole ratio of boron oxide:boric acid be between 5:1 and 10:1 with a preferred ratio range of between 6:1 and 8:1. In view of the temperature range of reaction, 120°–180° C, this reaction is carried out in an autoclave at autogeneous pressure. The resulting product can be used "as is" for its organoleptic properties or it can further be reacted with an $R_8MgX$ (e.g. $CH_3MgBr$) Grignard reagent or $R_8Li$ wherein $R_8$ is lower alkyl in a solvent (e.g., tetrahydrofuran or diethyl ether) followed by acid hydrolysis (e.g., dilute HCl) or it can further be reduced using hydrogen as a reducing agent and a hydrogenation catalyst such as 5% palladium-on-carbon or Raney nickel. In place of the boric acid:boron oxide catalyst this reaction can be carried out using only boron oxide, and in that case, it is preferred to use a temperature of between 170°–185° C at a pressure in the autoclave of between 40–100 psig.

Process 2

The camphene epoxide is prepared from reaction of camphene with a peralkanoic acid oxidizing agent, for example, peracetic acid or perpropionic acid. It is also preferred that the reaction take place from 0° up to 80° C (preferably, 40°–60° C) in the presence of a solvent inert to the reactants or the reaction product. Such an inert solvent is methylene chloride. Other useful inert solvents are benzene, toluene, xylene and cyclohexane. The mole ratio of camphene:peracetic acid is preferably slightly less than 1:1 since it is desired that all the camphene be reacted. At the end of the reaction any excess peracetic acid is neutralized and the camphene oxide may be isolated or the reaction mass may be used "as is" for the subsequent reaction. From an economic standpoint, it is preferred that the reaction mass be used "as is" rather than purify the camphene oxide. The resulting product is then rearranged to the aldehyde by heating with $MgCl_2$ or $MgBr_2$, and the resulting aldehyde is then admixed with a pre-prepared Grignard reagent having the formula:

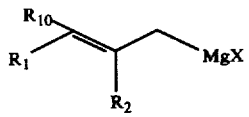

or organolithium reagent having the structure:

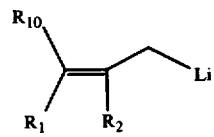

wherein X is one of the halogen atoms chlorine, iodine or bromine and $R_1$ and $R_2$ are the same or different hydrogen or lower alkyl. It is preferred that the Grignard reagent and the aldehyde each be respectively dissolved in appropriate solvents prior to admixing the aldehyde with the Grignard reagent. Suitable solvents for the reaction are tetrahydrofuran, diethyl ether, and mixtures of tetrahydrofuran or diethyl ether with benzene, toluene, xylene, or cyclohexane. It is preferred that reaction of the Grignard reagent or organolithium compound with the aldehyde take place at a temperature in the range of from 50° C up to 100° C at atmospheric pressure, preferably in the range of 65°–70° C. The resulting organometallic compound is then hydrolyzed with aqueous acid, preferably an aqueous protonic acid such as hydrochloric acid or phosphoric acid, whereby the pH of the resulting solution is approximately 1. The resulting alcohol, the hydrolyzed product, is then extracted from the reaction mass with a suitable inert extraction solvent such as benzene, toluene or xylene and is then isolated by means of evaporation and fractional distillation. The resulting alcohol may then be used "as is" for its organoleptic properties in perfumery, as a flavorant for foodstuffs, in chewing gums, medicinal products or tobaccos or as a flavor for tobacco; or it may further by reacted as by oxidation or reduction.

The oxidation of the alcohol is carried out using a suitable oxidation agent such as "Jones Reagent", sodium dichromate-sulfuric acid mixture, pyridinium chlorochromate, or a chromium trioxide-acetic acid-water mixture to form the corresponding ketone. The oxidation reaction may be carried out at temperatures between −10° C and +50° C. When using a Jones Reagent, it is preferred to use a temperature of about −5° C. It is noteworthy that oxidation systems such as dimethyl sulfoxide-acetic anhydride or copper chromite have not given successful oxidations. The resulting ketone may be hydrogenated using, for example, a palladium catalyst or a palladium-on-carbon catalyst, whereby a saturated ketone is formed for example, according to the reaction:

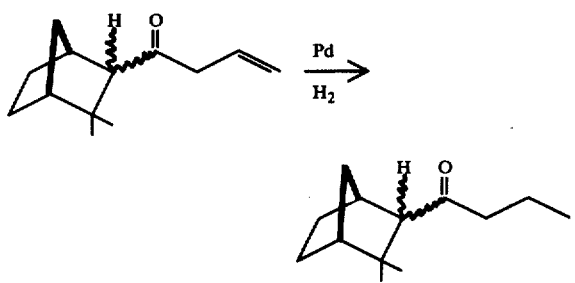

or the ketone can be used "as is" for its organoleptic properties. The hydrogenation is preferably carried out at temperatures in the range of from about 20° C up to 100° C.

Process 3

In the reaction of 3,3-dimethylnorbornane-2-carboxaldehyde with the Grignard reagent having the structure:

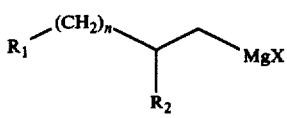

or the hydrocarbyl lithium compound having the structure:

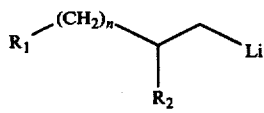

wherein $n$ is 0 or 1, either or both of $R_1$ or $R_2$ is hydrogen or lower alkyl and X is one of the halogen atoms, chlorine, bromine or iodine, the reaction conditions are essentially the same as those of the corresponding reaction in Process 2 and the recovery step are essentially the same. The resulting alcohol having the structure:

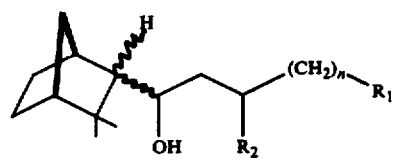

can be used as such for its organoleptic properties or it can be oxidized to form a ketone under the conditions set forth in Process 2 or it can be esterified with an esterification agent to form an ester having the structure:

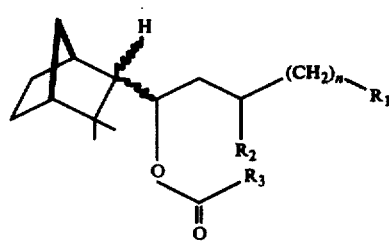

wherein $R_3$ is hydrogen or lower alkyl. Esterification agents are alkanoic acid anhydrides such as acetic anhydride, propionic anhydride, butyric anhydride; mixed anhydrides such as acetic-propionic anhydride; acyl halides such as acetyl chloride, propionyl chloride, acetyl bromide, propionyl bromide, n-butanoyl chloride, i-butanoyl chloride, n-pentanoyl chloride, n-octanoyl chloride, and n-lauroyl chloride.

Process 4

The reaction sequence:

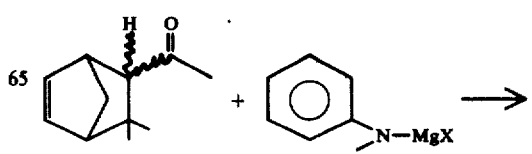

-continued

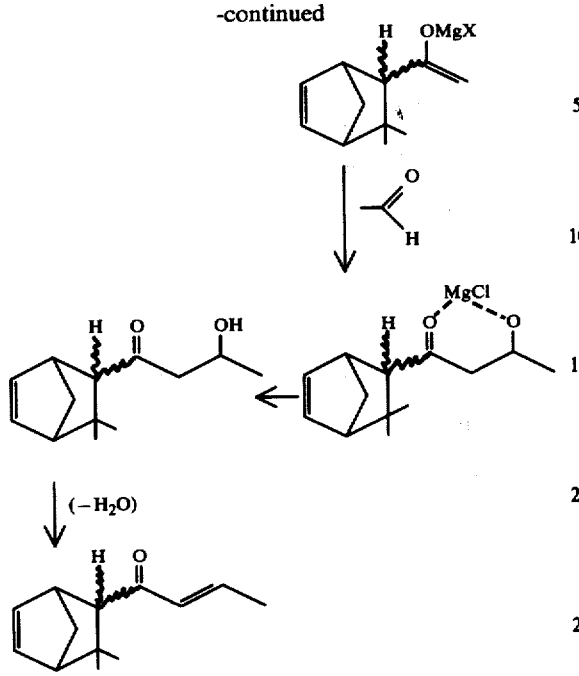

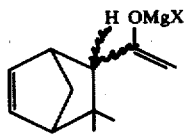

involves a reaction of methyl aniline with methyl magnesium halide (chloride, bromide or iodide) preferably each in an appropriate solvent such as benzene/tetrahydrofuran, tetrahydrofuran or diethyl ether. It is also preferred that the mole ratio of methyl aniline:methyl magnesium halide be 1:1. It is further preferred that the reaction temperature producing the compound having the structure:

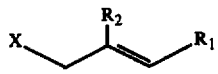

is from −5° C up to about 40° C with the most preferred temperature being 20°-30° C. The reaction of the above compound with acetaldehyde preferably takes place in the present of an appropriate solvent such as benzenetetrahydrofuran, tetrahydrofuran, or diethyl ether at a temperature in the range of from −5° C up to 20° C, with a preferred temperature of 0° C. The hydrolysis to form the keto alcohol is carried out using a mineral acid such as dilute aqueous hydrochloric acid, sulfuric acid or phosphoric acid or other protonic acids such as paratoluenesulfonic acid. The hydrolysis preferably takes place at 0° C. The dehydration reaction using the keto alcohol is carried out with a mild dehydrating agent such as a mixture of acetic anhydride and sodium acetate at a temperature in the range of 80°-150° C over a period of time of from about 1 up to 5 hours. The dehydration can also be carried out using a strong acid in a refluxing inert solvent, e.g., using a benzene-paratoluenesulfonic acid mixture. At the end of this reaction the excess dehydration agent, e.g. acetic anhydride, is destroyed and the reaction product isolated. Using this reaction sequence, only "trans" isomer is formed. If the starting material is "endo" 2-acetyl-3,3-dimethyl-5-norbornene, then the final product will also be an "endo" isomer. By the same token, if the starting material is "exo" 2-acetyl-3,3-dimethyl-5-norbornene, then the final product will be an "exo" isomer. Standard isolation techniques are used, e.g. fractional distillation and, if desired, preparative GLC for isolation of the end product.

Process 5

The reaction of 2-acetyl-3,3-dimethylnorbornane with the allyl chloride derivative takes place after first forming the enolate of the 2-acetyl-3,3-dimethylnorbornane, thusly:

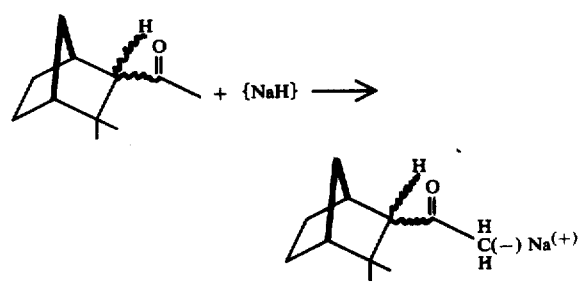

The reagent used to form such enolate is preferably a hydride such as sodium hydride and potassium hydride. The enolate is then reacted with the allyl halide having the structure:

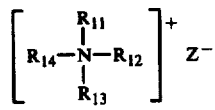

wherein $R_1$ and $R_2$ are the same or different hydrogen or lower alkyl and X is one of the halogen atoms, chlorine, bromine or iodine. In addition, a similar result may be obtained when using an alkali metal hydroxide in the presence of a phase transfer agent whereby the reactants for the process and the base, respectively, are in two immiscible phases and the phase transfer agent may be one or more of several quaternary salts. Specific examples of phase transfer agents useful in our invention are as follows:

Tricapryl methyl ammonium chloride;
Cetyl trimethyl ammonium bromide; and
Benzyl trimethyl ammonium hydroxide.

In general, the phase transfer agents most preferred have the generic formula:

$$\begin{bmatrix} R_{11} \\ | \\ R_{14}-N-R_{12} \\ | \\ R_{13} \end{bmatrix}^+ Z^-$$

wherein at least one of $R_{11}$, $R_{12}$, $R_{13}$ and $R_{14}$ is $C_6$-$C_{14}$ aryl, $C_6$-$C_{10}$ aralkyl, $C_6$-$C_{20}$ alkyl, $C_6$-$C_{14}$ alkaryl and $C_6$-$C_{20}$ alkenyl and the other of $R_{12}$, $R_{13}$, $R_{14}$ is alkyl such as methyl, ethyl, n-propyl, i-propyl, 1-butyl, 2-butyl, 1-methyl-2-propyl, 1-pentyl and 1-octyl and $Z^-$ is an anion such as chloride, bromide and hydroxide. Furthermore, this process is carried out in an inexpensive solvent which is inert to the reaction system such as toluene, benzene, o-xylene, m-xylene, p-xylene, ethyl benzene, n-hexane, cyclohexane, methylene chloride and o-dichlorobenzene. This Process (5) of our invention is carried out at a temperature in the range of from about 10° C up to about 150° C with a temperature range of 50°-120° C being preferred. The reaction time is inversely proportional to the reaction temperature, with lower reaction temperatures giving rise to greater reaction times; and, accordingly, the reaction time ranges from about 30 minutes up to about 10 hours.

In this reaction of our invention the mole ratio of 2-acetyl-3,3-dimethylnorbornane:allyl halide reactant is in the range of from 0.5:1.5 up to 1.5:0.5 with a preferred ratio of norbornane:allyl halide being from 1:1 up to 1:1.2.

The quantity of "phase transfer agent" in the reaction mass, based upon the amount of 2-acetyl-3,3-dimethyl-norbornane in the reaction mass, may vary from 0.5 grams of "phase transfer agent" per mole of norbornane derivative to 25 grams of "phase transfer agent" per mole of norbornane derivative with a preferred concentration of "phase transfer agent" being in the range of from 2.5 up to about 7.5 grams of "phase transfer agent" per mole of norbornane derivative.

Process (5) of our invention is preferably carried out at atmospheric pressure since that is the most convenient condition. However, lower or higher pressures can be used without detrimentally affecting the ultimate yield of desired reaction product.

Process 6

The initial compound formed is that created by reaction of the dialkyl carbonate with 2-acetyl-3,3-dimethyl-norbornane in the presence of an alkali metal hydride, as illustrated by the following reaction:

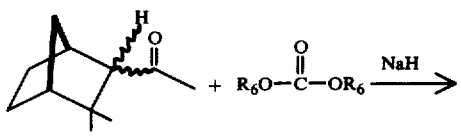

wherein $R_6$ is alkyl having from 1 up to 8 carbon atoms, but most conveniently ethyl. The reaction is preferably carried out under reflux conditions using a solvent inert to the reactants such as benzene, toluene or xylene. The mole ratio of norbornane derivative: dialkyl carbonate is preferably 1:2; but can vary from 1:1 up to 1:5. The ratio of base:dialkyl carbonate is preferably 1:1.

The reaction of the resulting beta-ketocarboxylic acid ester with the allyl halide having the structure:

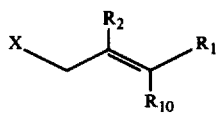

wherein X is a halogen, chlorine, bromine or iodine and $R_1$, $R_2$ and $R_{10}$ are the same or different hydrogen or lower alkyl), is carried out in the presence of approximately one equivalent of base such as an alkali metal hydride or alkali metal alkoxide or hydroxide in the presence of a suitable solvent. A "phase transfer agent" may be used.

The ketocarboxylic acid ester derivative has the structure:

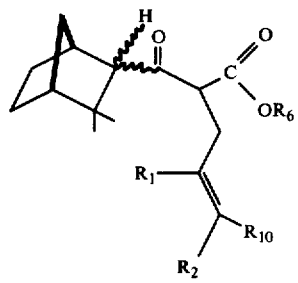

This ketocarboxylate, (a novel genus of compounds), is then saponified using standard techniques such as with an aqueous base such as 5-25% aqueous sodium hydroxide or potassium hydroxide, and the resulting alkali metal salt having the structure:

(wherein M is alkali metal), is then neutralized and simultaneously decarboxylated using aqueous mineral acid such as sulfuric acid or aqueous hydrochloric acid. The resulting reaction product having the structure:

(a mixture of cis and trans isomers; wherein $R_1$ and $R_2$ is alkyl) may then be used for its organoleptic properties "as is" or it may be hydrogenated with hydrogen using a catalyst such as palladium, palladium-on-carbon or Raney nickel, whereupon the carbon-carbon double bond in the side chain is reduced to a carbon-carbon single bond thereby forming a compound having the structure:

Both the unsaturated ketone and the saturated ketone may be reacted, if desired, with an alcohol or glycol in the presence of sulfuric acid or hydrochloric acid thereby forming a ketal according to the reaction:

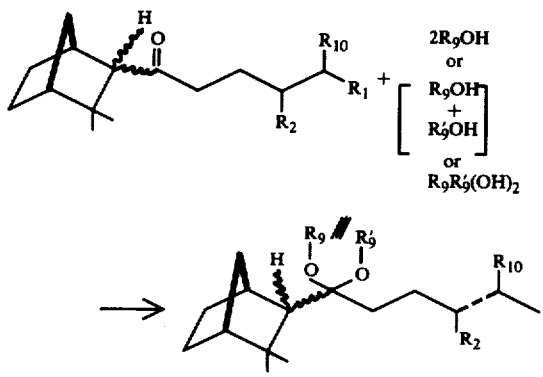

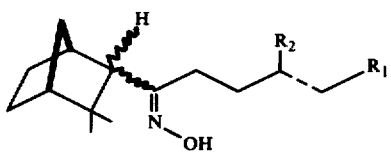

wherein R₉ and R₉' each represent lower alkyl taken separately or, when taken together, represents lower alkylene, e.g. ethylene; and wherein the dashed line represents a carbon-carbon single bond or a carbon-carbon double bond. Alternatively, either ketone may be converted into its corresponding oxime by using hydroxylamine or hydroxylamine acid salts such as hydroxylamine or hydrochloride whereby an oxime having the structure:

is formed. Such ketals and oximes also have useful organoleptic properties.

Process 7

In the reaction of the 2-acyl-3,3-dimethylnorbornane or the 2-acyl-3,3-dimethyl-5-norbornene with the Grignard reagent having the structure:

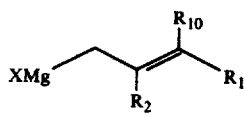

wherein $R_1$, $R_2$ and $R_{10}$ are separately hydrogen or lower alkyl and X is one of the halogen atoms, chlorine, bromine or iodine, the reaction conditions are essentially the same as those of the corresponding reaction in Process (2) and the recovery steps are essentially the same. $R_8'$ of the generic structure:

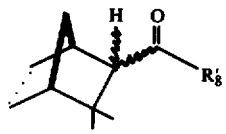

is defined wherein $R_8'$ is lower alkyl such as methyl, ethyl, n-propyl, i-propyl, n-butyl, i-butyl, n-pentyl and n-octyl. The resulting alcohol having the structure:

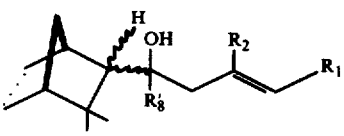

can be esterified in accordance with the corresponding reaction detailed in the Process (3) description, supra.

Specific examples of the compounds produced according to the foregoing processes are set forth in Table I below:

TABLE I

| STRUCTURE OF COMPOUND | NAME OF COMPOUND | PERFUMERY EVALUATION | FLAVOR EVALUATION | TOBACCO EVALUATION |
|---|---|---|---|---|
| cis and trans | 2(2'-butenoyl)-3,3-dimethyl-norbornane | Sweet, woody, fruity, spicey (nutmeg, pepper), herbaceous aroma with pine needle nuances. | Fruity, pine needle/green, winey aroma with piney, eugenol/clove, spicey, fruity, winey flavor. | |
| | 2-(3'-butenoyl)-3,3-dimethylnorbornane | Fruity, herbaceous, piney aroma with armoise character and fir-balsam characteristics. | Fruity-estery, cedarwood, floral, woody, balsam tree resin-like aroma with sweet, fruity, banana-like, estery, balsam tree resin-like, piney flavor character. | |
| | alpha-allyl-3,3-dimethyl-2-norbornanemethanol | Sweet, woody, thujone-like aroma with armoise, cedar leaf, piney and camphoraceous nuances. | A sweet, fruity berry aroma with woody, incense, warm tea-like, floral nuances and an incense and cedarwood flavor with rosey, berry and tea nuances. | |
| | alpha-methallyl-3,3-dimethyl-2-norbornanemethanol | Fruity, musty, sweet, woody, minty aroma with fresh cut pine/spruce nuances. | Incense and woody aroma and an incense and woody flavor with astringent and bitter notes. | |
| | alpha-ethyl-3,3-dimethyl-2-norbornanemethanol | Musty, sweet fruity, woody aroma with artimesia characteristics. | A sweet, woody, minty aroma with camphoraceous green/earthy nuances and a woody, green and minty flavor with spicey, earthy, red beet-like and camphoraceous nuances as well as a cooling effect. | A woody, sweet, fruity, cooling aroma and taste before and on smoking. |
| cis and trans | endo-2(2'-butenoyl)-3,3-dimethyl-5-norbornane | Woody, piney, natural-like aroma with fruity, spicey, cresylic, borneol nuances, as well as a definitive berry top note. | Balsam, blueberry, piney, green fruity, woody aroma with balsam resin-like, piney, woody and blueberry flavor characteristics. | |

TABLE I-continued

| STRUCTURE OF COMPOUND | NAME OF COMPOUND | PERFUMERY EVALUATION | FLAVOR EVALUATION | TOBACCO EVALUATION |
|---|---|---|---|---|
| 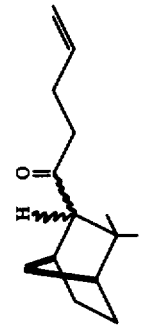 | Mixture of 2-acetyl-2-allyl-3,3-dimethylnorbornane and 3,3-dimethyl-2-(4'-pentenoyl)-norbornane | Camphoraceous, woody, fruity (orange) aroma with green, piney undertones. | | |
| 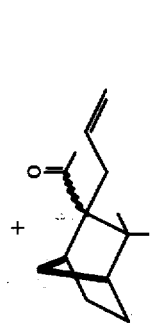 | 2-(cis-2'-buten-1'-oyl)-3,3-dimethyl)-norbornane | Intense, piney, fruity, with floral, berry and cologne nuances. | | |
| 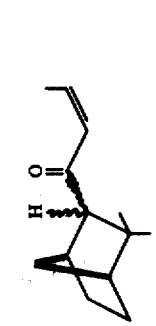 | 3,3-dimethyl-2-(4'-pentenoyl)-norbornane | A sweet, fruity, fir-balsam, floral aroma with woody and pine-apple notes. | Sweet, fruity, pine-apple, green, woody, apple juice-like, piney aroma character with berry, piney, oriental-like and woody flavor and character. | |
| 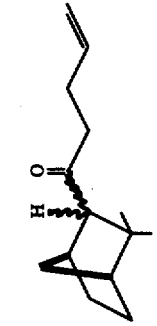 | 3,3-dimethyl-2-pentanoylnorbornane | Sweet, fruity, fir-balsam, aroma with floral (ylang, jasmin) and berry notes. | A sweet, fruity/berry, raspberry, woody and plum aroma with sweet, fruity/berry, raspberry, valerian oil-like, woody and plum flavor characteristics. | |
| 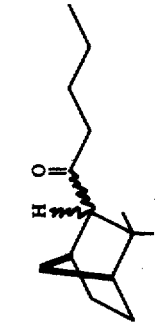 | 3,3-dimethyl-alpha-propyl-2-norbornane-methanol | Camphoraceous, woody, green aroma with minty nuances. | A sweet, delicate piney, fruity, berry-like, valerian oil-like, woody aroma with sweet, delicate piney, evergreen-like, fruity, berry and astringent flavor characteristics. | |

TABLE I-continued

| STRUCTURE OF COMPOUND | NAME OF COMPOUND | PERFUMERY EVALUATION | FLAVOR EVALUATION | TOBACCO EVALUATION |
|---|---|---|---|---|
| 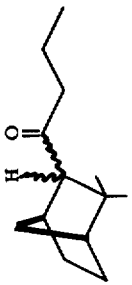 | 2-butyryl-3,3-dimethylnorbornane | A sweet, piney needle-like fruity, camphoraceous aroma. | A sweet, delicate, piney, fruity, fir balsam needle oil-like, blueberry, woody and strawberry-like aroma with sweet, delicate piney, blueberry, juniper-like, strawberry and astringent nuances. | |
| 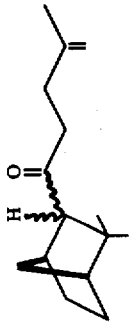 | Mixture of 3,3-dimethyl-2(4'-methyl-4'-pentenoyl)-norbornane and 3,3-dimethyl-2-acetyl-2(2'-methyl-2'-propenyl)-norbornane | A fruity, woody, low-keyed but long lasting aroma. | A camphoraceous, woody and minty aroma with a strong cooling nuance and a strong, woody and minty flavor. | |
| 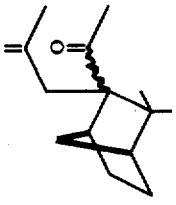 | 2-acetyl-2-methallyl-3,3-dimethyl-norbornane | 003 A low-keyed, sweet, camphoraceous, woody (cedarwood) aroma with green, herbaceous and piney nuances. | | |
| 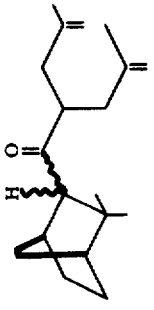 | 3,3-dimethyl-2-(2-methylallyl-4'-methyl-4'-pentenoyl)-norbornane | A low-keyed, sweet, green, woody, herbaceous aroma with a waxy nuance. | | A woody aroma, prior to and on smoking with sweet, spicey, floral nuances. |

Mixture of:

TABLE I-continued

| STRUCTURE OF COMPOUND | NAME OF COMPOUND | PERFUMERY EVALUATION | FLAVOR EVALUATION | TOBACCO EVALUATION |
|---|---|---|---|---|
| 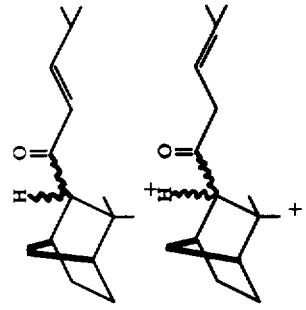 | Mixture of 3,3-dimethyl-2-(4'-methyl-2'-pentenoyl)-norbornane; 3,3-dimethyl-2-(4'-methyl-3'-pentenoyl)-norbornane; and 3,3-dimethyl-2-(4'-methyl-3-methoxypentenoyl)-norbornane | a long lasting, excellent, fruity and berry aroma. | A fruity, raspberry and sweet aroma with a green nuance and a fruity, raspberry, green flavor with a bitter nuance. | A sweet, fruity-raspberry-like aroma prior to smoking and a sweet, fruity, raspberry aroma with green nuances on smoking, when used in both the tobacco and in the filter. |
| 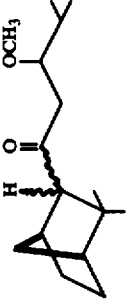 | Mixture of 3,3-dimethyl-2-(4'-methyl-2'-pentenoyl)-5-norbornene; 3,3-dimethyl-2-(4'-methyl-3'-pentenoyl)-5-norbornene; and 3,3-dimethyl-2-(4'-methyl-3-methoxypentenoyl)-5-norbornene | A fruity, berry-like aroma. | A sweet, red berry jam-like, fruity aroma with citrus, ionone-like, berry-like, pine needle-like and pungent nuances and a fruity, red berry-like, berry jam-like flavor with green, fresh raspberry and piney nuances. | A sweet, floral and green aroma prior to smoking, and a sweet, fruity, floral aroma on smoking in the mainstream and in the sidestream. |

TABLE I-continued

| STRUCTURE OF COMPOUND | NAME OF COMPOUND | PERFUMERY EVALUATION | FLAVOR EVALUATION | TOBACCO EVALUATION |
|---|---|---|---|---|
| | alpha-ethyl-3,3-dimethyl-2-norbornanemethanol | A minty, sweet fruity, woody aroma with some artemesia character and, in addition, herbaceous and pine needle nuances. | A sweet, woody, minty aroma with green and earthy nuances and a woody, green, minty flavor with spicey, earthy, cooling and red beet nuances. | A sweet, woody, piney aroma and a strong, cooling effect when used in the filter, both prior to, and, on smoking. Also reduces harshness and gives rise to a "fresh" effect. |
| | alpha-allyl-alpha-3,3-trimethyl-2-norbornanemethanol | Low-keyed, sweet, woody (cut pine) note. | Sweet, earthy, piney, cedarwood aroma with sweet, cedarwood, fruity, blueberry-like flavor with patchouli and walnut nuances. | |
| | alpha-allyl-alpha-3,3-trimethyl-5-norbornene-2-methanol | A sweet, minty, fruity, slight melony, woody aroma. | A piney, fruity, woody, patchouli-like, carrot, walnut aroma with a sweet, fruity, woody, camphoraceous, carrot, dried apple, patchouli-like, walnut and astringent flavor. | |

When the norbornane derivatives of our invention are used as food flavor adjuvants, the nature of the co-ingredients included with each of the said norbornane derivatives in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, diary products, candies, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates one or more of the norbornane derivatives of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unaceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisol (mixture of 2- and 3-tertiary-butyl-4-hydroxyanisole), butylated hydroxytoluene (2,6-di-tertiary-butyl-4-methylphenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectines, and emulsifiers, e.g., mono- and diglycerides of fatty acids, skim milk powder, hexoses, pentoses, disaccharides. e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispensing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasis calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include aldehydes, esters, natural oils, alcohols, sulfides, ketones, lactones, carboxylic acids and hydrocarbons such as heliotropin, terpinenol-4, benzaldehyde, anisaldehyde, phenyl acetaldehyde, benzyl formate, benzyl acetate, cis-3-hexenyl benzoate, methyl hexanoate, hexanal, eucalyptol, eugenol, acetaldehyde, ethyl acetate, ethyl butyrate, turpentine gum oil, limonene, gum camphor, isobornyl acetate, borneol, cinnamic aldehyde, cuminic aldehyde, furfural, methyl cinnamate, cassia oil, vanillin, maltol, parahydroxybenzyl acetone, dimethyl sulfide, alpha-ionone, acetic acid, isobutyl acetate, acetone, butyric acid, formic acid, valeric acid, amyl acetate, amyl butyrate, anethol, benzyl salicylate, diacetyl, dimethyl anthranilate, ethyl methylphenylglycidate, ethyl succinate, ethyl valerate, geraniol, cis-3-hexen-1-ol, 2-hexenyl acetate, 2-hexenyl butyrate, hexyl butyrate, 4-(p-hydroxyphenyl)-2-butanone, beta-ionone, isobutyl cinnamate, jasmine, lemon essential oil, methyl butyrate, methyl caproate, methyl disulfide, methyl p-naphthyl ketone, orris butter, rose absolute, terpenyl acetate, gammaundecalactone, vanilla and alcohol.

The specific flavoring adjuvant selected for use may be either solid or liquid depending upon the desired physical form of the ultimate product, i.e., foodstuff, whether simulated or natural, and should, in any event, (i) be organoleptically compatible with the norbornane derivatives of our invention by not covering or spoiling the organoleptic properties (aroma and/or taste) thereof; (ii) be non-reactive with the norbornane derivatives of our invention and (iii) be capable of providing an environment in which the norbornane derivatives can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of norbornane derivatives employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum, per se, medicinal product per se, toothpaste per se, or flavoring composition.

The use of insufficient quantities of norbornane derivatives will, of course, substantially vitiate any possibility of obtaining the desired results while excess quantities prove needlessly costly and, in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of norbornane derivatives ranging from a small but effective amount, e.g., 0.5 parts per million up to about 100 parts per million based on total composition are suitable. Concentrations in excess of the maximum quantity stated are not normally recommended, since they fail to prove commensurate enhancement of organoleptic properties. In those instances, wherein the norbornane derivatives are added to the foodstuff as an integral component of a flavoring composition, it is, of course, essential that the total quantity of flavoring composition employed be sufficient to yield an effective norbornane derivative concentration in the foodstuff product.

Food flavoring compositions prepared in accordance with the present invention preferably contain the norbornane derivatives in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the norbornane derivatives with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and norbornane derivatives in a dry blender until the requisite degree of uniformity is achieved.

It is presently preferred to combine with the norbornane derivatives of our invention, the following adjuvants:

Heliotropin;
Terpinenol-4;
Benzaldehyde;
Anisaldehyde;
Phenyl acetaldehyde;
Benzyl formate;
Benzyl acetate;
Cis-3-hexenyl benzoate;
Methyl hexanoate;
Hexanal;
Eucalyptol;
Eugenol;
Acetaldehyde;
Ethyl acetate;
Ethyl butyrate;
Turpentine gum oil;
Limonene;
Gum camphor;
Isobornyl acetate;
Borneol;
Cinnamic aldehyde;
Cuminic aldehyde;
Furfural;
Methyl cinnamate,
Cassia oil;
Vanillin;
Maltol;
Parahydroxybenzylacetone;
Dimethyl sulfide;
Alpha-ionone;
Acetic acid;
Isobutyl acetate;
Acetone;
Butyric acid;
Formic acid;
Valeric acid;
Amyl acetate;
Amyl butyrate;
Anethol;
Benzyl salicylate;
Diacetyl;
Dimethyl anthranilate;
Ethyl methylphenylglycidate;
Ethyl succinate;
Ethyl valerate;
Geraniol;
Cis-3-hexen-1-ol;
2-Hexenyl acetate;
2-Hexenyl butyrate;
Hexyl butyrate;
4-(p-Hydroxyphenyl)-2-butanone;
Beta-ionone;
Isobutyl cinnamate;
Jasmine;
Lemon essential oil;
Methyl butyrate;
Methyl capronate;
Methyl disulfide;
Methyl p-naphthyl ketone;
Orris butter;
Rose absolute;
Terpenyl acetate;
Gamma-undecalactone, Vanilla; and
Alcohol.

An additional aspect of our invention provides an organoleptically improved smoking tobacco product and additives therefor, as well as methods of making the same which overcome problems heretofore encountered in which specific desired sweet, woody, piney and fruity flavor characteristics of natural tobacco (prior to smoking and, on smoking, in the mainstream and in the sidestream) as well as cooling effects, are created or enhanced or modified or augmented and may be readily controlled and maintained at the desired uniform level regardless of variations in the tobacco components of the blend.

This invention further provides improved tobacco additives and methods whereby various desirable natural aromatic tobacco flavoring characteristics with sweet, woody, piney, cooling and fruity notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient one or more norbornane derivatives of our invention.

In addition to the norbornane derivatives of our invention other flavoring and aroma additives may be added to the smoking tobacco material or substitute therefor either separately or in mixture with the norbornane derivatives as follows:

I. Synthetic Materials

Beta-ethyl-cinnamaldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropylacetophenone;
2-Hydroxy-2,5,5,8a-tetramethyl-1-(2-hydroxyethyl)-decahydronaphthalene;
Dodecahydro-3a,6,6,9a-tetramethyl-naphtho-(2,1-b)-furan
4-Hydroxyhexnoic acid, gamma lactone; and
Polyisoprenoid hydrocarbons defined in Example V of U.S. Pat. No. 3,589,372 issued on June 29, 1971.

II. Natural Oils

Celery seed oil;
Coffee extract;
Bergamot Oil;
Cocoa extract;
Nutmeg Oil; and
Origanum Oil.

An aroma and flavoring concentrate containing one or more norbornane derivatives of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet notes and/or cooling notes and/or fruity notes and/or woody notes, we have found that satisfactory results are obtained if the proportion by weight of the sum total of norbornane derivative(s) to smoking tobacco material is between 50 ppm and 1,500 ppm (.015%-.15%). We have further found that satisfactory results are obtained if the proportion by weight of the sum total of norbornane derivative used to flavoring material is between 1,500 and 15,000 ppm (0.15%-1.5%).

Any convenient method for incorporating the norbornane derivative(s) into the tobacco product may be employed. Thus, the norbornane derivative(s) taken alone or along with other flavoring additives may be dissolved in a suitable solvent such as ethanol, diethyl ether and/or volative organic solvents and the resulting solution may either be spread on the cured, cased and blended tobacco material or the tobacco material may be dipped into such solution. Under certain circumstances, a solution of the norbornane derivative(s) taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the norbornane derivative(s) in excess of the amounts or concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of 2-(2-butenoyl)-3,3-dimethylnorbornane having the structure:

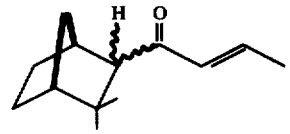

in an amount to provide a tobacco composition containing 800 ppm by weight of 2-(2-butenoyl)-3,3-dimethylnorbornane on a dry basis. Thereafter, the alcohol is removed by evaporation and the tobacco is manufactured into cigarettes by the usual techniques. The cigarette when treated as indicated has a desired and pleasing aroma which is detectable in the main and sidestreams when the cigarette is smoked. This aroma is described as being sweeter, more aromatic, more tobacco-like and having sweet, fruity notes.

While our invention is particularly useful in the manufacture of smoking tobacco, such s cigarette tobacco, cigar tobacco and pipe tobacco, other tobacco products, formed from sheeted tobacco dust or fines may also be used. Likewise, the norbornane derivative(s) of our invention can be incorporated with materials such as filter tip materials (e.g. cellulose acetate filters wherein sweet, woody, piney and/or cooling effects are desired), seam paste, packaging materials and the like which are used along with tobacco to form a product adapted for smoking. Furthermore, the norbornane derivative(s) can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The norbornane derivative(s) and one or more auxiliary perfume ingredients, including, for example, hydrocarbons, alcohols, ketones, aldehydes, nitriles, esters, lactones or cyclic esters, synthetic essential oils and natural essential oils, may be admixed so that the combined odors of the individual components produce a pleasant and desired fragrance, particularly and preferably in woody and/or piney fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, one or more of the norbornane derivative(s) of our invention can be used to alter, modify or enhance the aroma characteristics of a perfume composition, for example, by utilizing or moderating the olfactory reaction contributed by another ingredient in the composition.

The amount of norbornane derivative(s) of our invention which will be effective in perfume compositions as well as in perfumed articles and colognes depends on many factors, including the other ingredients, their amounts and the effects which are desired. It has been found that perfume compositions containing as little as 0.01% of norbornane derivative(s) or even less (e.g., 0.005%) can be used to impart a sweet, piney, woody, floral, fruity odor with berry, evergreen-like and tobacco-like nuances to soaps, cosmetics, detergents (including anionic, non-ionic and cationic detergents) or other products. The amount employed can range up to 70% of the fragrance components and will depend on considerations of cost, nature of the end product, the effect desired on the finished product and the particular fragrance sought.

The norbornane derivative(s) of our invention are useful (taken alone or together with other ingredients in perfume compositions) in detergents and soaps, space odorants and deodorants, perfumes, colognes, toilet water, bath preparations, such s lacquers, brilliantines, pomades and shampoos; cosmetic preparations, such as creams, deodorants, hand lotions and sun screens; powders, such as talcs, dusting powders, face powders and the like. As little as 1% of norbornane derivative(s) will suffice to impart an intense piney note to woody perfume formulations. Generally, no more than 3% of norbornane derivative(s) based on the ultimate end product, is required in the perfume composition.

In addition, the perfume composition or fragrance composition of our invention can contain a vehicle, or carrier for the norbornane derivative(s). The vehicle can be a liquid such as a non-toxic alcohol, a non-toxic glycol, or the like. The carrier can also be an absorbent solid, such as a gum (e.g., gum arabic), or components for encapsulating the composition (such as gelatin).

It will thus be apparent that the norbornane derivative(s) of our invention can be utilized to alter, modify or enhance sensory properties, particularly organoleptic properties, such as flavor(s) and/or fragrance(s) of a wide variety of consumable materials.

Examples I-XXXI, following serve to illustrate processes for specifically producing the norbornane derivatives useful in our invention.

The following examples serve to illustrate specific embodiments of our invention.

It will be understood that these Examples are illustrative and the invention is to be considered restricted thereto only as indicated in the appended claims.

All parts and percentages given herein are by weight unless otherwise specified.

EXAMPLE I

PREPARATION OF 3,3-DIMETHYL-2-NORBORNANECARBOXALDEHYDE

Reaction:

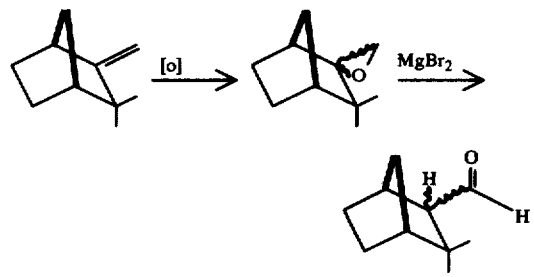

Procedure

Into a 3 liter flask fitted with a stirrer, addition funnel, reflux condenser and thermometer are placed the following materials:
Camphene (80%): 500 g
Methylene chloride: 500 cc
Sodium carbonate: 300 g

| Camphene (80%) | 500 g |
| Methylene chloride | 500 cc |
| Sodium carbonate | 300 g |

The slurry is stirred while 600 cc of peracetic acid (40%) is added over a six hour period. The temperature rises until the mixture is at reflux (44° C) in the beginning, 48° C at the end of the addition). The course of the reaction is monitored by GLC. The mixture is allowed to stir for 2 hours after the completion of the addition. The salts are then removed by filtration. The methylene chloride is stripped off and 500 cc of benzene is added. The mixture is azeotroped using a water separation trap to remove traces of water. After all water is removed, the mixture (670 g) is ready for use in the next step. A GLC (samples are prepared by dissolving the salts in water, separating the organic layer and washing it several times with water. The GLC conditions are: 10 feet × ⅛ inch SE-30 column, programmed at 80°-200° at 8° C per minute) indicated 26% benzene, 9.6% tricyclene and 61.2% camphene oxide, corresponding to a yield of 408 g of camphene oxide, or 92% of theory.

50 Grams of magnesium bromide is added and the mixture is refluxed for four hours. At the end of this time a GLC analysis (10 feet × ⅛ inch Carbowax 20M column, programmed from 80°-220° C at 8° C/minute) shows complete conversion of the camphene oxide to 3,3-dimethyl-2-norbornanecarboxaldehyde.

EXAMPLE II
PREPARATION OF ALPHA-ALLYL-3,3-DIMETHYL-2-NORBORNANEMETHANOL

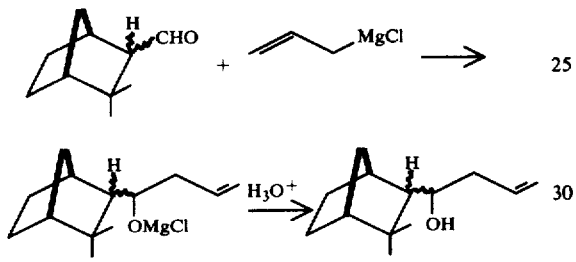

Procedure

Into a 3 liter reaction flask fitted with a stirrer, reflux condenser, thermometer, dropping funnel and a $N_2$ bleed, is added 55 g of magnesium turnings (2.26 moles) and 1 liter of anhydrous tetrahydrofuran. The apparatus is blanketed with dry $N_2$, and 2 moles of allyl chloride (152 g, 162 ml) is placed in the addition funnel; about 10 cc is added at once with stirring. When the reaction begins (exotherm to 30°), the flask and contents are cooled to 0° C (dry ice/isopropyl alcohol bath) and the remainder of the allyl chloride is added over a 3 hour period while the temperature is kept at 0°-5°. When addition is complete the contents of the flask are stirred for an additional hour while warming to 22° C at room temperature. The Grignard solution is decanted from the excess magnesium into another reaction flask and 330 g of a solution of 3,3-dimethyl-2-norbornanecarboxaldehyde in benzene prepared as in Example I (62% aldehyde by GLC area normalization) is added over one hour. The reaction is exothermic and the temperature rises until the solution refluxes (65°-70° C). At the end of the addition, the mixture is heated and refluxed for an additional ½ hour. The Grignard complex is hydrolyzed by the addition of about 400 cc of 15% HCl (to a pH of 1). The aqueous layer is separated and extracted with 200 cc of benzene. The combined organic layers are stripped on a rotary evaporator and the residue is distilled through a 1 foot stone packed column after adding thereto 30 g of Primol ®, at 70°-77° C at 0.2-0.25 mm Hg pressure, yielding 206 grams product. The resulting product is essentially one peak by GLC analysis (conditions: 10 foot × ⅛ inch SE-30 column, programmed at 80°-220° C at 8°/min.). This corresponds to a yield of 92% theory based on 3,3-dimethyl-2-norbornanecarboxaldehyde added. This peak consists of a compound having the structure:

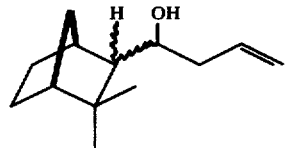

NMR Data:

| | | |
|---|---|---|
| 0.92 ppm | | |
| 0.98 | singlets, methyl protons | (3H each) |
| 1.0–2.4 | complex signals | |
| 4.85–5.20 | multiplet, CH=CH$_2$ | 2H |
| 5.68–6.08 | multiplet, CH=CH$_2$ | 1H |

Mass spectral data:

m/e = 70, 55, 41, 111, 67, 109

Infrared data:

cm$^{-1}$ 3475 (—OH), 3079 (—CH=CH$_2$)

Figure 1:
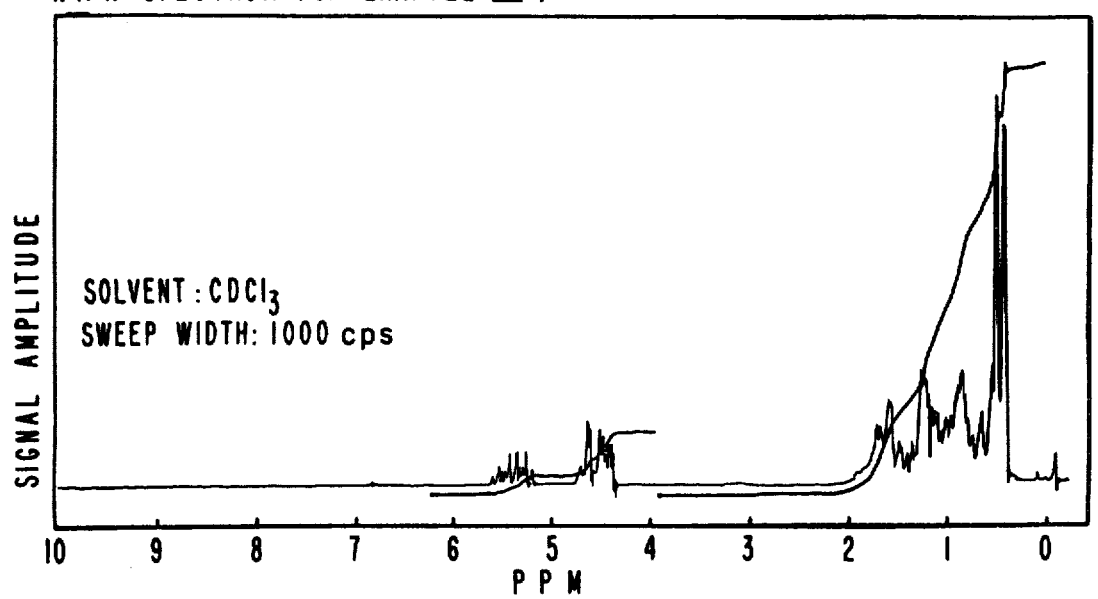
FIG. 1 illustrates the NMR spectrum of the compound having the structure.

The NMR spectrum is set forth in FIG. 1.
The Infrared spectrum is set forth in FIG. 2.

EXAMPLE III
PREPARATION OF 2-(3-BUTENOYL)-3,3-DIMETHYLNORBORNANE USING A SODIIUM DICHROMATE-SULFURIC ACID-BENZENE OXIDIZING SYSTEM

Reaction:

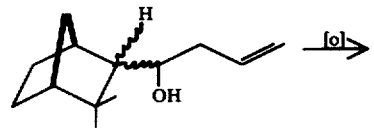

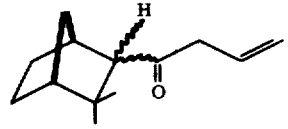

Procedure

Sulfuric acid (60 cc, 110 g) is added slowly to 300 ml water with stirring. When the solution cools to room temperature, 300 cc (263 g) of benzene and 50 g of alpha-allyl-3,3-dimethyl-2-norbornanemethanol is added. The mixture is stirred at room temperature and 20 g of sodium dichromate is added. After one hour a second 20 g portion is added. After an additional one hour of stirring the layers are separated. The benzene layer is washed with saturated NaHCO$_3$ solution and then with water. The solvent is stripped and the residue is distilled rapidly to yield two distillation fractions. The first distillation fraction has a boiling point range of 65°-97° C at 1.2 mm and weighs 2.5 g. The second distillation fraction has a boiling point range of 97°-99° C at 1.0 mm Hg and weighs 39.4 grams, corresponding to a yield of 80% of theory.

The second distillation fraction is primarily a compound having the structure:

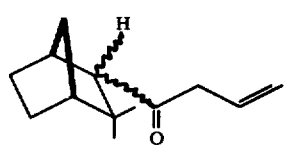

This compound is purified by means of column chromatography on a column of silicic acid (deactivated by the addition of 5% water). The compound is eluted with a mixture of 2% diethyl ether in isopentane. Thus, from 1.5 grams of this second distillation fraction was obtained, after solvent stripping, 1.0 grams of an oil which was distilled on a micro distillation apparatus, yielding pure 2-(3-butenoyl)-3,3-dimethylnorbornane (i), having the following spectral characteristics:

(i) Structure:

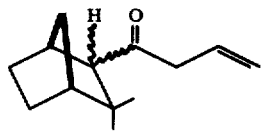

NMR data:

| δ,ppm | | Interpretation |
|---|---|---|
| 0.95 | | |
| 1.0 | | methyl singlets |
| 1.18 | | (endo and exo isomers) |
| 1.24 | | |
| 1.0–2.5 | | complex signals |
| 3.12 | O<br>‖<br>C—CH$_2$—CH=CH$_2$ | doublet of quartets |
| 6.1 | | |
| 6.9 | CH$_2$—CH=CH$_2$ | multiplets |

The NMR spectrum for this compound is set forth in FIG. 5. The Infrared spectrum is set forth in FIG. 6.

When either crude or purified 2-(3-butenoyl)-3,3-dimethylnorbornane is subjected to GLC analysis, a second material is observed. This material is trapped and identified as cis-2-(3-butenoyl)-3,3-dimethylnorbornane (ii), having the following spectral characteristics:

(ii) Structure:

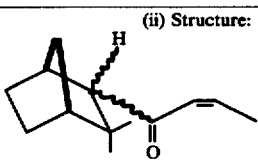

(cis isomer)

NMR data:

| δ, ppm | | Interpretation |
|---|---|---|
| 0.85 | | |
| 0.96 | | methyl singlets |
| 1.20 | | (endo and exo isomers) |
| 1.24 | | |
| 1.88 | \ /CH$_3$<br>C=C<br>/ \<br>H H | doublet of triplets |
| 1.0–2.5 | | complex signals |
| 6.12 | | multiplets |
| 6.76 | \ /<br>C=C<br>/ \<br>H H | |

Mass Spectral Data:

-continued (ii) Structure:

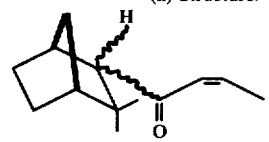

(cis isomer)

m/e=41, 69, 125, 67, 81, 108, 1234

Infrared Datum:

cm$^{-1}$ 1685 (conjugated carbonyl)

The NMR spectrum is set forth in FIG. 3. The Infrared spectrum is set forth in FIG. 4.

EXAMPLES IV–X

OXIDATION AND ATTEMPTED OXIDATION OF ALPHA-ALLYL-3,3-DIMETHYL-2-NORBORNANEMETHANOL

Using different oxidizing agents, the following Examples, as set forth in Table I, are performed with the results indicated whereby 2-(3-butenoyl)-3,3-dimethylnorbornane is produced in a number of reactions and is not produced where "no reaction" is indicated.

TABLE I

| Ex. No. | Quantity of Alcohol Reactant | Oxidizing Agent and Conditions | Result |
|---|---|---|---|
| IV | | Jones Reagent at room temperature. | Mixture of many products formed. |
| V | 50 g | Na$_2$Cr$_2$O$_7$ (40 g)/H$_2$SO$_4$ (60 cc)/benzene (300 cc); room temperature for 2 hours. | Successful oxidations; 50% conversion to ketone. |
| VI | 1 g | 10 ml dimethyl sulfoxide/5 g acetic anhydride at 60° C. | No reaction. |
| VII | 10 g | Copper chromite (1g)/ 200° C for 1 hour. | No reaction. |
| VIII | 5 g | Pyridinium chlorochromate (8.5 g) (prepared according to Corey, Tetrahedron Letters, 31, 2647, 1975); methylene dichloride (50 cc); room temperature; 1 hour. | 50% conversion to ketone. |
| IX | 5 g | Chromium trioxide (2.5 g)/acetic acid (5 ml)/water (50 ml); room temperature; 1 hour. | 50% conversion to ketone. |
| X | 15 g | Jones reagent (25 ml) (prepared according to Example IV)/acetone (15 ml), −5° C, 2 hours. | 90% conversion to ketone. |

EXAMPLE XI

PREPARATION OF ENDO-2-(TRANS-2-BUTENOYL)-3,3-DIMETHYL-5-NORBORNENE

Reaction:

Reaction:

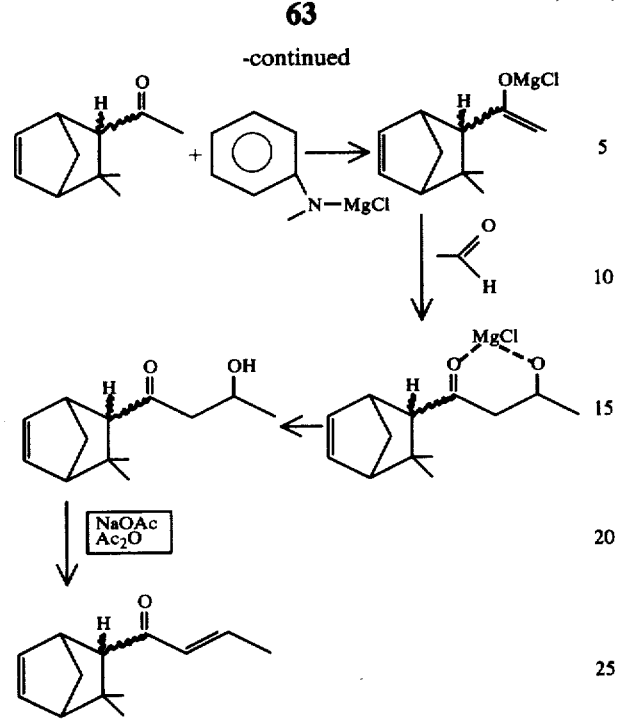

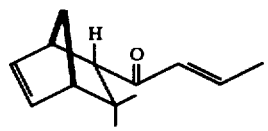

The NMR spectrum is set forth in FIG. 7. The Infrared spectrum is set forth in FIG. 8.

EXAMPLE XII

PREPARATION OF 2-(2-BUTENOYL)-3,3-DIMETHYLNORBORNANE (PRIMARILY THE "TRANS" ISOMER)

Reaction:

Reaction:

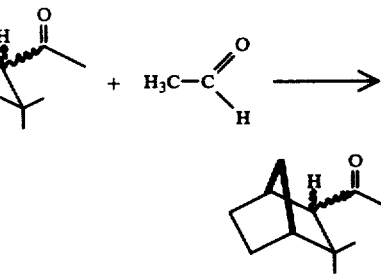

Into a three necked flask equipped with a condenser, thermometer, mechanical stirrer and cooling bath (dry-ice-isopropyl alcohol) is charged 666 grams (3.0 moles) of 3M methylmagnesium chloride in tetrahydrofuran. To this is added a solution of 321 grams (3.0 moles) of methyl aniline in 300 ml of benzene over a 30 minute period, keeping the reaction temperature at 20°-30° C. The reaction is exothermic and methane gas is evolved. When the gas evolution ceases a solution of 510 g (3.0 moles) of endo-2-acetyl-3,3-dimethyl-5-norbornene (prepared by AlCl$_3$ catalyzed reaction of cyclopentadiene and mesityl oxide, U.S. Pat. No. 3,852,358) in 300 ml of benzene is added over 40 minutes with the temperature kept at 20°-30° C. The mixture is stirred at room temperature for 1 hour and then cooled to 0° C. At this temperature 132 g (3.0 moles) of acetaldehyde in 300 ml of benzene is added over 30 minutes. After an additional 30 minutes at 0° C, 600 g of 37% HCl diluted with 1200 ml of water is added. After another 15 minutes at 0° C the layers are separated. The organic layer is washed twice with water and dried over MgSO$_4$. The solvent is evaporated keeping the liquid temperature below 45° C. The residue is then combined with 600 ml of acetic anhydride and 150 g of sodium acetate, stirred and heated to 100° C for 2 hours. The mixture is cooled to 80° C and water is added to destroy excess acetic anhydride. The mixture is cooled, washed with water, saturated NaHCO$_3$ solution and dried over MgSO$_4$. The product is distilled without fractionation to give 204 g of an oil, b.p. 70°-130° C (1.0-1.5 mm). This material contained about 50% starting ketone and a mixture of reaction products. The major reaction product is isolated by redistillation followed by preparative GLC on a 6 foot × ¼ inch column packed with 10% Carbowax 20M. On the basis of its NMR spectrum the product is predominantly the endo isomer (>90%):

Into a 2 liter autoclave the following materials are placed:

| Ingredients | Quantity |
| --- | --- |
| 2-acetyl-3,3-dimethyl-norbornane | 644 g (4 moles) |
| acetaldehyde | 132 g (3 moles) |
| boron oxide | 105 g (1.5 moles) |
| boric acid | 12 g (0.2 moles) |

The autoclave is sealed and the contents are heated at 150° C for a period of 3 hours at autogeneous pressure. At the end of the 3 hour period the contents of the autoclave are cooled to room temperature and filtered. The filter cake is washed with 250 ml cyclohexane and the filtrate is distilled rapidly through a 2 inch column, after adding thereto 20 g Primol ® and 0.1 g Ionox ® to give 649 g of oil collected at 77°-129° C and a pressure of 2.7-4.0 mm Hg. This material is then fractionally distilled on a 12 inch × 1 inch Goodloe column, after adding thereto Primol ® and Ionox ®, to give 490 g of oil collected at 73°-78° C and a pressure of 3.3-4 mm Hg. The resulting material, insofar as its fragrance properties are concerned, has a sweet, woody, fruity, spicey and herbaceous aroma with pine needle nuances. Insofar as flavor characteristics are concerned, this material has a fruity, pine needle/green, winey aroma with a piney, eugenol/clove, spicey, fruity and winey flavor.

NMR, Infrared and Mass Spectral analyses confirm that the resulting structure is:

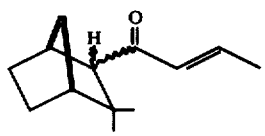

NMR data:

| δ, ppm | | Interpretation |
|---|---|---|
| 0.82 | | |
| 0.93 | | singlets, methyl protons |
| 1.16 | | (endo and exo isomers) |
| 1.20 | | |
| 1.28 | =CH—CH₃ | doublet of doublets |
| 1.0–2.5 | | complex signals |
| 6.1 | \\_  _/H | multiplets 1H each |
| 6.7 | C=C | |
| | /    \\ | |
| | H | |

Mass Spectral Data:
 m/e = 69, 41, 125, 39, 67, 108
Infrared Data:
 cm⁻¹ 1690 (conjugated carbonyl)

The NMR spectrum is set forth in FIG. 9. The Infrared spectrum is set forth in FIG. 10.

EXAMPLE XIII

PREPARATION OF 2-(2-BUTENOYL)-3,3-DIMETHYLNORBORNANE

Reaction:

Reaction:

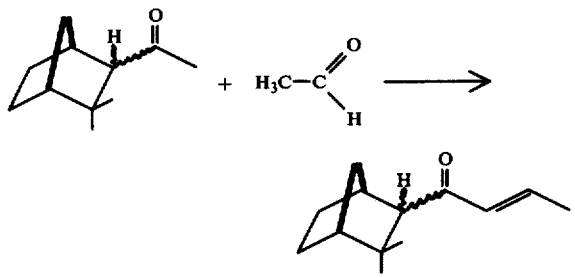

Into a 2 liter autoclave the following materials are placed:

| Ingredients | Quantity |
|---|---|
| 2-acetyl-3,3-dimethyl- | |
| norbornane | 830 g (5 moles) |
| acetaldehyde | 88 g (2 moles) |
| boron oxide | 50 g (0.71 moles) |

The autoclave is sealed and the contents thereof are heated to 170°–185° C and maintained at that temperature for two hours during which time the pressure within the autoclave is 50 psig. At the end of the two hour period the reaction mass is cooled to room temperature and decanted, and the resulting liquid, after adding thereto 20 g Primol ® and 0.1 g Ionox ®, is distilled rapidly through a 2 inch column, to yield 625 g of crude material collected at 77°–129° C and a pressure of 2.7–4.0 mm Hg. The resulting material, after adding thereto Primol ® and Ionox ®, is then fractionally distilled through a 12 inch × 1 inch Goodloe column at 73°–78° C and a pressure of 3.3–4 mm Hg. The major peak is trapped on a GLC column yielding a material having the structure:

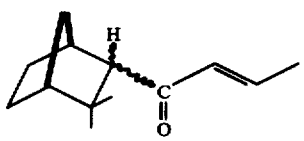

as confirmed by GLC, IR and NMR analyses.

The material has a fruity aroma with piney and musty nuances insofar as its fragrance properties are concerned and a fruity and berry aroma with waxy, berry, sour and bitter flavor characteristics insofar as its taste properties are concerned.

EXAMPLE XIV

BLUEBERRY FLAVOR FORMULATION

The following formulation is prepared:

| Ingredients | Parts by Weight |
|---|---|
| Heliotropin | 3.0 |
| Terpinenol-4 (10% in 95% aqueous foor grade ethanol) | 0.2 |
| Benzaldehyde | 1.5 |
| Anisaldehyde | 0.2 |
| Phenyl acetaldehyde | 0.4 |
| Benzyl formate | 0.5 |
| Benzyl acetate | 2.0 |
| Cis-3-hexenyl benzoate (10% in 95% aqueous food grade ethanol) | 0.5 |
| Methyl hexanoate | 2.0 |
| Hexanal | 1.0 |
| Eucalyptol (1% in 95% aqeuous food grade ethanol) | 0.5 |
| Eugenol | 0.2 |
| Acetaldehyde | 3.0 |
| Ethyl acetate | 21.0 |
| Ethyl butyrate | 26.0 |
| Propylene glycol | 38.0 |
| | 100.0 |

The above formulation is split into 2 portions. To the first portion is added, at the rate of 1%, 2-(2-butenoyl)-3,3-dimethylnorbornane. The second portion contains nothing added thereto. Both formulations, with and without the said 2-(2-butenoyl)-3,3-dimethylnorbornane (produced according to Example XII), are combined with water at the rate of 100 ppm. The flavor with the 2-(2-butenoyl)-3,3-dimethylnorbornane, prepared according to Example XII, has a more winey, fruity, piney character and is closely similar to the flavor of wild blueberries. It is therefor preferred to the basic blueberry formulation which does not contain said 2-(2-butenoyl)-3,3-dimethylnorbornane.

EXAMPLE XV

PINE NEEDLE OIL FORMULATION

The following formulation is prepared:

| Ingredients | Parts by Weight |
|---|---|
| Turpentine gum oil | 100 |
| Limonene | 70 |
| Gum camphor | 10 |
| Isobornyl acetate | 50 |
| Borneol | 30 |
| 2-(2-Butenoyl)-3,3-dimethylnorbornane (produced according to Example XII) | 40 |
| Mixture of 2-(3-butenoyl)-3,3-dimethyl-norbonrnane and 2-(2-butenoyl)-3,3-dimethylnorbornane (produced according to the process of Example III | 100 |

| Ingredients | Parts by Weight |
|---|---|
| Alpha-allyl-3,3-dimethyl-2-norbornane-methanol (produced according to the process of Example II) | 70 | the 2-(2-butenoyl)-3,3-dimethylnorbornane produced according to Example XII imparts a green, melony, herbal, ozoney and twiggy character of pine needle to the middle portion of the aroma profile and dry out.

The mixture of 2-(2-butenoyl)-3,3-dimethylnorbornane and 2-(3-butenoyl)-3,3-dimethylnorbornane produced according to Example III imparts the sweet, bright, melony, herbal lift so necessary to this pine needle oil formulation.

The alpha-allyl-3,3-dimethyl-2-norbornanemethanol produced according to Example II imparts the sweet, woody, melony, cut wood note to the dry out aroma of this pine needle oil formulation.

EXAMPLE XVI

FLAVOR USE OF ALPHA-ALLYL-3,3-DIMETHYL-2-NORBORNANEMETHANOL

The following basic cinnamon formulation is prepared:

| Ingredients | Parts by Weight |
|---|---|
| Cinnamic aldehyde | 70 |
| Eugenol | 15 |
| Cuminic aldehyde | 1 |
| Furfural | 0.5 |
| Methyl cinnamate | 5.0 |
| Cassia oil | 8.5 |

This formulation is split into two parts. To the first part is added, at the rate of 5%, alpha-allyl-3,3-dimethyl-2-norbornanemethanol prepared according to Example II. To the second part no additive is added. The alpha-allyl-3,3-dimethyl-2-norbornanemethanol adds a more cinnamon bark-like character in aroma and taste and a more woody/sweet aroma. It is therefor preferred to the formulation without such additive. The formulations are compared in water at the rate of 10 ppm.

EXAMPLE XVII

PREPARATION OF ALPHA-ETHYL-3,3-DIMETHYL-2-NORBORNANEMETHANOL

Reaction:

Reaction:

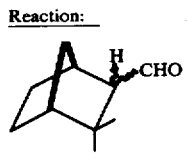

$C_2H_5MgCl \longrightarrow$

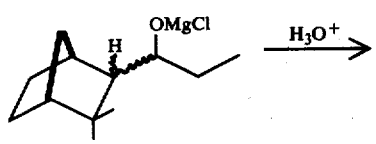

$\xrightarrow{H_3O^+}$

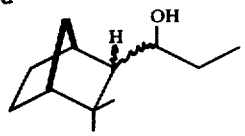

Into a 1 liter reaction flask equipped with a stirrer, thermometer, condenser, nitrogen inlet tube and dropping funnel is placed 129 cc of a 2.9 molar solution of ethyl magnesium chloride in tetrahydrofuran. Over a 20 minute period 19.0 g of 3,3-dimethyl-2-norbornanecarboxaldehyde is added with stirring. The reaction is exothermic. The reaction mass is then refluxed for a period of 3 hours. At the end of the 3 hour period the reaction mass is cooled to room temperature, and 100 cc of saturated ammonium chloride solution is added thereto. The organic layer is then extracted with 500 cc diethyl ether, and the extract is concentrated and distilled through a micro Vigreux column after adding thereto 3 g of Primol ®.

Mass spectral, NMR and infrared analysis of the distilled product, b.p. 85° C at 1.5 mm Hg, indicates that it has the structure:

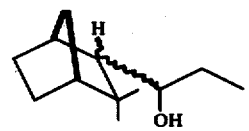

NMR data:

| δ, ppm | Interpretation |
|---|---|
| 0.96 singlets 1.02 | gem dimethyl |
| 1.04 triplet 1.0–2.4 multiplet | —CH$_2$—CH$_3$ |
| 3.5 multiplet | —CH$_2$—and —CH— HO H |

Mass Spectral Data:
m/e = 67, 41, 121, 81, 59, 182 (parent peak)

From a food flavor standpoint the resulting material has a sweet, woody, minty aroma with camphoraceous, green and earthy nuances and a woody, green, minty flavor with spicey, earthy, cooling, red beet-like and camphoraceous nuances at 5 ppm. From a perfumery standpoint the resulting material has a musty, sweet, fruity, woody aroma with an artemesia character.

This material has a significant utility in tobacco filter flavors where it lends a cooling effect with sweet, woody and piney notes both prior to and during smoking, when 10 micro liters of a 10% solution is added to the filter.

The NMR spectrum is set forth in FIG. 11.
The Infrared spectrum is set forth in FIG. 12.

EXAMPLE XVIII

USE OF ALPHA-ETHYL-3,3-DIMETHYL-2-NORBORNANEMETHANOL

The followng basic raspberry formulation is prepared:

| Ingredients | Parts by Weight |
|---|---|
| Vanillin | 2 |
| Maltol | 4 |
| Parahydroxy benzyl acetone | 5 |
| Dimethyl sulfide | 1 |
| Alpha-ionone (10% in propylene glycol) | 2 |
| Ethyl butyrate | 6 |
| Ethyl acetate | 16 |
| Isobutyl acetate | 14 |
| Acetic acid | 10 |
| Acetaldehyde | 10 |
| Propylene glycol | 930 |
| | 1000 |

The above formulation is split into two parts. To the first part, at the rate of 0.3% is added alpha-ethyl-3,3-dimethyl-2-norbornanemethanol produced according to Example XVII. No additive is added to the second part. The two formulations are compared in water at the rate of 50 ppm. The flavor containing the alpha-ethyl-3,3-dimethyl-2-norbornanemethanol has a more ripe raspberry taste and a woody, raspberry kernel character. Therefore, the raspberry formulation containing the norbornane derivative as an additive has a more natural like and more characteristic raspberry flavor and is therefor preferred.

EXAMPLE XIX

PREPARATION OF ALPHA-METHALLYL-3,3-DIMETHYL-2-NOR-BORNANEMETHANOL

Reaction:

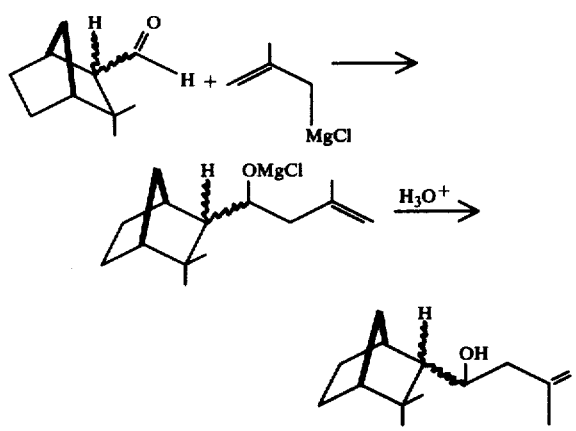

Into a 3 liter reaction flask equipped with a stirrer, condenser, nitrogen inlet tube, thermometer and dropping funnel are placed 24 g of magnesium with just enough tetrahydrofuran to cover it. Two milliliters (approximately 20 cc) of methallyl chloride, is then added to start the reaction. When the reaction is well under way, 500 cc of tetrahydrofuran is added, and 90.5 g of methally chloride is added dropwise over a period of 2 hours while maintaining a steady reflux. After the final addition, refluxing is continued for a period of one hour. Fifty grams of norbornane aldehyde, produced according to Example I, dissolved in 100 cc of toluene is then added over a period of 20 minutes, and the reaction mass is again refluxed for a period of 3 hours. The reaction mass is then cooled to room temperature, and 100 cc of saturated aqueous ammonium chloride solution is then added thereto. The reaction mass is then extracted with diethyl ether and the diethyl ether extract is concentrated. The concentrate is then distilled on an 8 inch × 1½ inch porcelain saddle packed columm after adding thereto 5 g of Primol ®.

The distilled product, b.p. 100° C at 2.0 mm Hg, is subjected to NMR, IR, Mass Spectral and UV analyses confirming that the structure is:

NMR data:

| δ, ppm | Interpretation |
|---|---|
| 0.94 singlets | gem dimethyl |
| 1.0 | |
| 1.77 singlet | ⧹=⧸CH₃ |
| 1.0–2.4 multiplet | —CH₂— and —CH— |
| 4.72 multiplet | ⧹=CH₂ |

Mass Spectral Data:

m/e = 69, 41, 55, 43, 69,208 (parent peak).

The resulting material has a musty, sweet, woody, minty aroma with an intense, fresh cut pine/spruce nuance.

The NMR spectrum is set forth in FIG. 13.
The Infrared spectrum is set forth in FIG. 14.

EXAMPLE XX

PREPARATION OF 2-(4'-METHYL-2'-PENTENOYL)-3,3-DIMETHYL-NORBORNANE

Reaction:

Reaction:

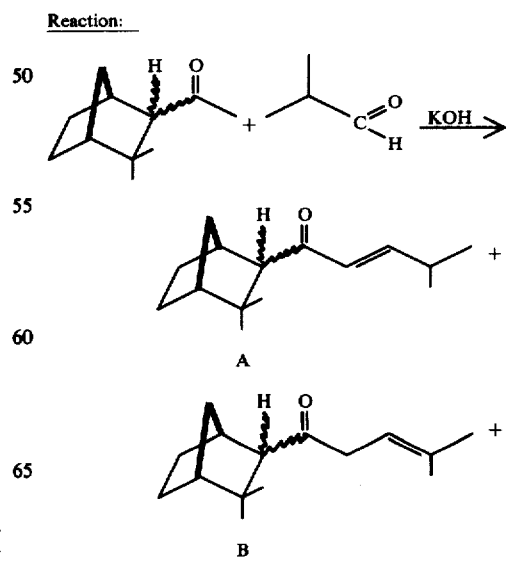

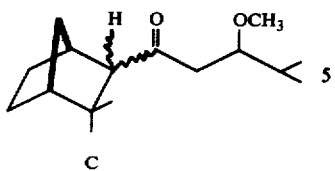

C

Into a 3 liter reaction flask equipped with a stirrer, thermometer, reflux condenser, addition funnel and nitrogen inlet tube the following materials are added:

| Ingredient | Amount |
| --- | --- |
| methanol | 500 g |
| potassium hydroxide | 56 g |
| toluene | 50 g |
| 2-acetyl-3,3-dimethyl-norbornane | 500 g |

The reaction mass is heated to reflux for a period of 1 hour at which time 240 g (3.3 moles) of isobutyraldehyde is added over a period of 20 minutes. When the addition is complete, the reaction mass is stirred for an additional 4 hours at a temperature of 72° C. At the end of the four hour period, 50 g of concentrated HCl is added to the reaction mass. The reaction mass is then admixed with 1 liter of water and 500 ml of toluene. The aqueous phase is then extracted with one 250 ml portion of toluene, and the toluene is combined with the organic layer which is washed as follows:

two 250 ml portions of water;
one 500 ml portion of 5% sodium bicarbonate solution; and
one 250 ml portions of saturated sodium chloride solution.

The crude material is then stripped of solvent using a Buchi evaporator, and the stripped crude (after adding thereto 25 g Primol ® and 1 g Ionox ®) is rapidly distilled using a 2 inch column. The distilled material is then fractionated on a 12 inch Goodloe packed column after adding thereto 30 g Primol ® and 1 g Ionox ®.

GLC, NMR, Infrared and Mass Sepectral analyses yield the information that the resulting material is a mixture of three compounds having the structures:

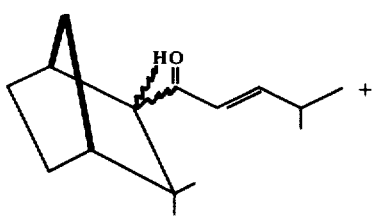

A

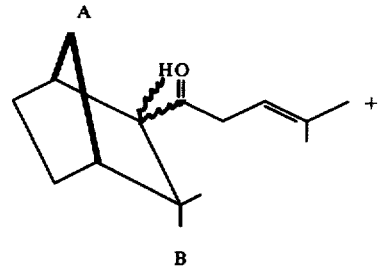

B

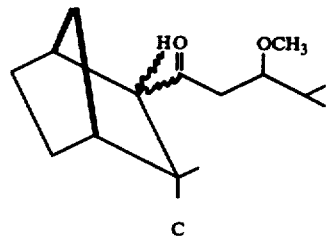

C

The GLC profile is set forth in FIG. 15.

The NMR spectrum for the mixture of compounds having the structures:

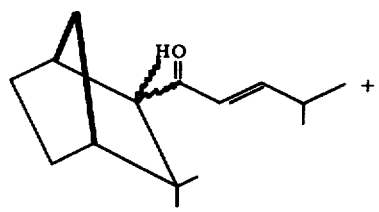

A

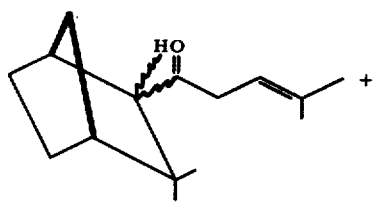

B

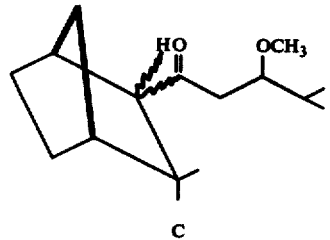

C is set forth in FIG. 16. The infrared spectrum is set forth in FIG. 17.

The NMR spectrum for the mixture of ketones having the structures:

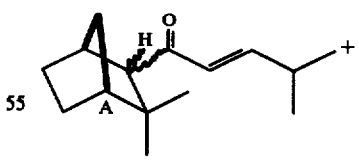

A

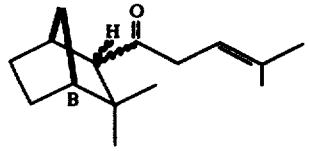

B is set forth in FIG. 18. The Infrared spectrum for this mixture of ketones is set forth in FIG. 19.

The NMR spectrum for the compound having the structure:

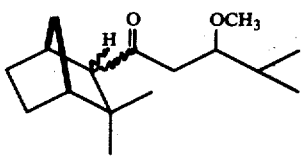

is set forth in FIG. 20. The Infrared spectrum for this keto-ether compound is set forth in FIG. 21.

| Structural Assignments | |
|---|---|
| I. Mixture of A and B | |
| Infrared Data: | |
| 1618 cm$^{-1}$, 1705, 1698 | |
| NMR Data (CDCl$_3$): | |
| ppm | Interpretation |
| 6.70 | doublet of doublets (J ≈ 16 Hz, 7Hz) |
| 6.00 | doublet of doublets (J ≈ 6 Hz, 1 Hz) |
| 5.28 | broad triplet (J ≈ 6 Hz) |
| 3.03 | broad doublet (J ≈ 6 Hz) |
| 1.74, 1.63 | broad singlets |
| 1.23, 0.87, 0.83 | singlets |
| 1.07 | doublet (J ≈ 6 Hz) |

Comparison of the integrals for the signals at 6.70 and 6.00 ppm with the signal at 5.28 ppm shows that the ratio of A/B is approximately 1.1.

| II. Compound C | |
|---|---|
| NMR Data: | |
| ppm | Interpretation |
| 3.50 | 1H multiplet |
| 3.74, 3.31 | 3H two singlets |

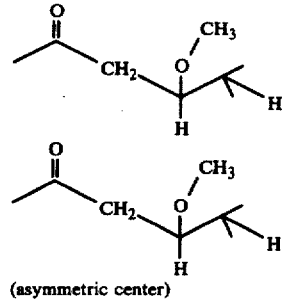
(asymmetric center)

| | | |
|---|---|---|
| II. Compound C | | |
| 1.24 | 3H singlet | |
| 0.85 | 3H singlet | |
| 0.89 | 6H doublet (J ≈ 5 Hz) | |

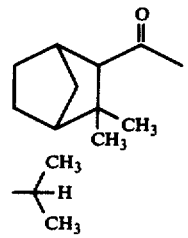

Infrared Datum:
1705 cm$^{-1}$

The overall mixture of the three compounds in Fraction 12, from a food flavor standpoint, has a fruity, raspberry, sweet aroma with a green nuance and a fruity, raspberry, green flavor with a bitter nuance at 5 ppm. The mixture of ketones A and B, from a perfumery standpoint, has a long lasting fruity, berry-like aroma with chocolate, spicey, winey, sweet, balsamic, fruity, pineapple, raspberry, cinammon, ionone-like, musty, floral, woody, salicyl and amyris nuances. When used with tobacco it has a sweet, fruity, raspberry-like, green aroma prior to smoking, and adds a sweet, fruity, green taste to the tobacco smoke flavor when used at 200–500 ppm levels in tobacco.

EXAMPLE XXI

PREPARATION OF 2-(4'-METHYL-2'-PENTENOYL)-3,3-DIMETHYL-5-NORBORNENE

Reaction:

Reaction:

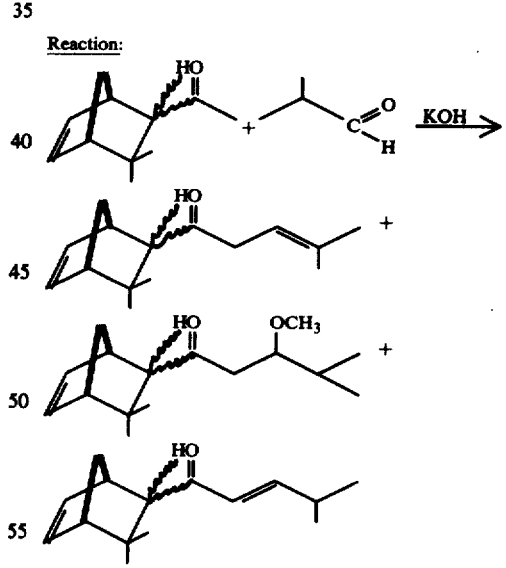

Into a 3 liter reaction flask equipped with a stirrer, thermometer, reflux condenser and addition funnel are placed a solution of 56 g of potassium hydroxide in 500 g of methanol. While maintaining the methanol/KOH solution at 2°–4° C, a solution of 500 g (3 moles) of 2-acetyl-3,3-dimethyl-5-norbornene, 240 g (3.3 moles) of isobutyraldehyde, and 50 g of toluene is added from the addition funnel over a period of 35 minutes.

The reaction mass is then stirred for a period of one hour at 2°–4° C and for a period of 12 hours at 71° C to 73° C, while refluxing. The reaction mass is then cooled and transferred to a separatory funnel and mixed with 1 liter of water and 500 ml toluene. The aqueous layer is separated and extracted with one 250 ml portion of toluene. The organic layer is combined with the toluene extract and is washed with:

one 500 ml portion of water;

one 500 ml portion of 5% sodium bicarbonate solution; and one 500 ml portion of saturated aqueous sodium chloride solution.

The crude organic material is then stripped of solvent and distilled rapidly after adding thereto 25 g Primol ® and 1 gram Ionol ®.

The distilled material is then fractionally distilled on a 12 inch Goodloe column.

GLC, IR, NMR and Mass Spectral analyses yield the information that the resulting material is a mixture of 3 compounds having the structures:

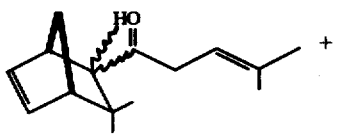

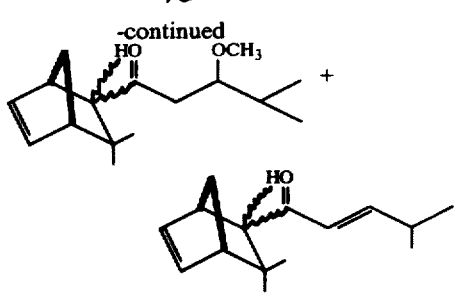

The GLC profile for this mixture is set forth in FIG. 22.

The product, from a food flavor standpoint, has a sweet, red berry jam-like, fruity aroma with citrus, ionone-like, berry, pine-needle and pungent nuances and a fruity, red berry jam flavor with green, fresh raspberry and piney nuances.

From a perfumery standpoint this material has a fruity, berry-like aroma. In tobacco, prior to smoking, this material has a sweet, floral-like, green aroma. On smoking, sweet, fruity and slightly floral nuances are created.

The three materials produced are separarted in a GLC column (conditions: 5 feet × ¼ inch 5% SE-30 column operated at 200° C isothermal).

The NMR spectrum for the mixture of compounds having the structures:

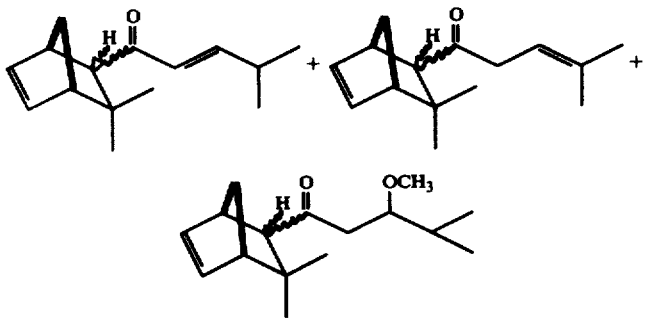

Spectral Data for Total Mixture

Infrared Data:

$1620^{cm-1}$, 1705, 1685, 1660

NMR Data:

| ppm | | Interpretation |
|---|---|---|
| 6.74 | doublet of doublets (J ≈ 16 Hz, 7 Hz) | |
| 5.95 – 6.50 | multiplet | |
| 5.34 | broad triplet | |
| 1.78 1.66 | broad singlets | |
| 1.13, 1.04, 0.81, 0.79 | singlets | |

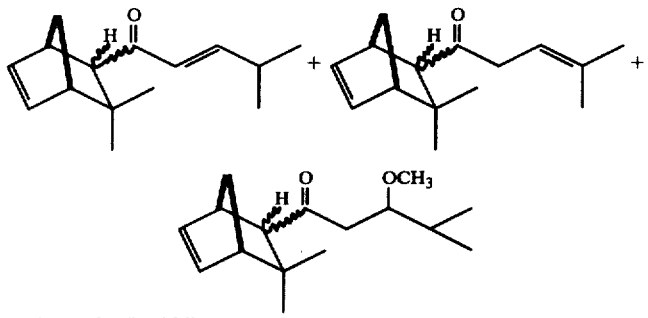

Spectral Data for Total Mixture
Infrared Data:
$1620^{cm-1}$, 1705, 1685, 1660
NMR Data:

| ppm | | Interpretation |
|---|---|---|
| 1.03 | doublet (J ≃ 6 Hz) | CH₃—CH—CH₃ |
| 3.80 3.40 | singlets | O—CH₃ (asymmetric center) |

EXAMPLE XXII

PREPARATION OF 2-(1-HYDROXYBUTYL)-3,3-DIMETHYLNORBORNANE AND 2-BUTYRYL-3,3-DIMETHYLNORBORNANE

Reaction:

Reaction:
PART A

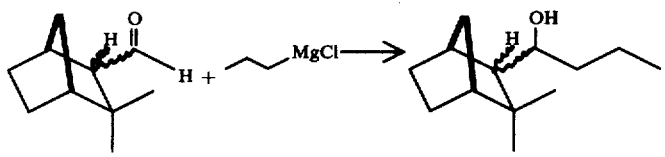

PART B

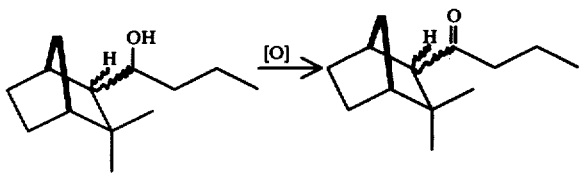

PART A

Into a 200 cc flask equipped with a stirrer, thermometer and reflux condenser is placed 15 g of dimethylnorbornanecarboxyaldehyde, produced according to the process of Example I, and 50 cc diethyl ether. Over a 15 minute period 50 cc of a solution of n-propyl magnesium chloride (2.2 molar in diethyl ether) is added to the aldehyde. The reaction mass is then refluxed for a period of ½ hour whereupon a GLC analysis indicated complete reaction of the norbornanecarboxaldehyde. The resulting reaction mass is then hydrolyzed with saturated aqueous ammonium chloride solution, and water is then added to dissolve the salts. The water phase is extracted with 50 cc of diethyl ether, and the ether extract is combined with the organic phase and stripped. The product is distilled on a micro Vigreux column yielding 13.3 grams in 5 fractions, b.p. 79°-82° C at 1 mm Hg.

NMR Data:

| δ, ppm | Interpretation |
|---|---|
| 0.88 1.02 1.01 | singlets, gem dimethyl protons (2 sets; 2 isomers exo and endo) |
| 1.25 | |
| 1.06 triplet | $CH_3$—$CH_2$— |
| 2.34–1.32 | methylene and methine protons |

-continued 3.56 multiplet $$\begin{matrix} | \\ HC-O- \\ | \end{matrix}$$

1.13 singlet    OH

Infrared Data:
950, 1005, 1055, 1100, 1355, 1375, 1455, 2860, 2920, 2950, 3360 cm$^{-1}$ Mass Spectral Data:
m/e = 41, 135, 55, 67, 43, 27; parent peak = 196

The NMR spectrum is set forth in FIG. 25. The Infrared spectrum is set forth in FIG. 26.

PART B

A 2.5 g portion of the distillate produced in Part A is dissolved in 10 cc of acetone and the resulting solution is cooled to 0°–5° C while a "Jones Reagent" prepared according to Example IV is added dropwise (2 ml total required). GlC analysis indicates one product is formed. 25 cc of water is added to the reaction mass, and the aqueous phase is extracted with diethyl ether. The diethyl ether extract and the organic phase are combined and washed with saturated sodium chloride solution. The washed organic solution is stripped and distilled on a micro Vigreux column yielding 1.3 grams of product, distilling at 90° C and 1.0 mm Hg pressure.

NMR, IR and Mass Spectrual analyses confirm that the compound is 2-butyryl-3,3-dimethylnorbornane.

| NMR Data: δ, ppm | Interpretation |
|---|---|
| 0.84 0.90 0.95 1.14 1.31 | —CH$_2$CH$_3$; —CH$_3$; endo and exo isomers |
| 1.0–1.06 | multiplets |
| 2.3 triplet | $\begin{matrix} O \\ \| \\ -C-CH_2CH_3 \end{matrix}$ |

Infrared Datum:
1700 cm$^{-1}$ (C=O)

Mass Spectral Data:
m/e = 123, 43, 41, 127, 27, 67; parent peak = 194

The NMR spectrum is set forth in FIG. 27. The Infrared spectrum is set forth in FIG. 28.

EXAMPLE XXIII

PREPARATION OF 2-BUTYROYL-3,3-DIMETHYLNORBORNANE

Reaction:

Reaction:

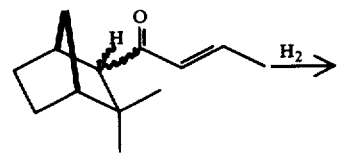

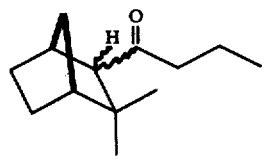

Into a 250 cc Parr shaker the following materials are placed:

| Ingredient | Quantity |
|---|---|
| 2-(trans-2-butenoyl)-3,3-dimethylnorbornane prepared according to the process of Example XII | 90 g |
| 5% palladium-on-carbon catalyst | 1 g |

The Parr shaker is sealed and then pressurized up to 50 psig with hydrogen and periodically repressurized over a period of 7 hours to maintain a pressure of 50 psig. During this period of time the temperature of the reaction mass remains at 25° C. At the end of the 7 hour period the Parr shaker is opened and the contents removed and filtered. To the filtrate, 5.0 g of Primol ® and 0.1 g of Ionol ® is added. The resulting mixture is then distilled on a four foot Vigreux column to give 47 g of oil, b.p. 93-95° C at 3.0 mm Hg.

NMR, IR and Mass Spectral analyses yield the information that the product has the structure:

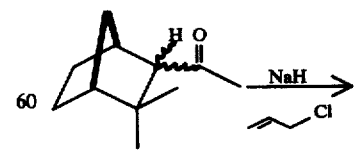

| NMR Data: δ, ppm | Assignments |
|---|---|
| 0.85 0.96 1.14 1.22 | singlets, 2 sets, (2 isomers) |
| 0.89 (t) | CH$_3$—CH$_2$— |
| 2.08 – 1.46 | methylene and methine protons |
| 2.30 | diffuse triplet protons alpha carbonyl |

Infrared Data:
1100, 1115, 1290, 1360, 1400, 1455, 1700, 2870, 2940 cm$^{-1}$

Mass Spectral Data:
m/e = 123, 41, 43, 127, 27, 151; parent peak = 194

The NMR spectrum is set forth in FIG. 29. The infrared spectrum is set forth in FIG. 30.

EXAMPLE XXIV

PREPARATION OF 2-(4'-PENTENOYL)-3,3-DIMETHYLNORBORNANE

Reaction:

Reaction:

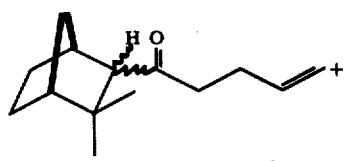

-continued

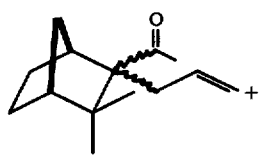

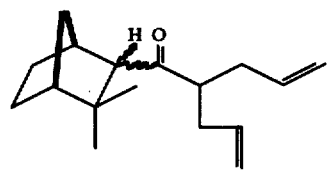

Into a 500 ml reaction flask equipped with a stirrer, thermometer, reflux condenser, addition funnel and nitrogen inlet tube is placed a suspension of 48 g of 55% sodium hydride and 250 ml toluene. Under a nitrogen blanket, 166 g (1mole) of 2-acetyl-3,3-dimethylnorbornane is added over a period of 5 minutes. The resulting mixture is heated to reflux for a period of 70 minutes and then is cooled to 45° C. Allyl chloride (76 g, 1 mole) and 4 g of tricapryl methyl ammonium chloride (Aliquat 336 ®, produced by General Mills Chemical Inc.) is added thereto over a period of 15 minutes. The reaction mass is then stirred at 60° C for a period of 12 hours.

The resulting suspension is allowed to settle, and the reaction mass is filtered through glass wool. The fitrate is washed with water, and the solvent is removed on a rotary evaporator to yield a white milky oil. GLC analysis indicates three peaks. The GLC profile (conditions: 8 feet × ¼ inch SE-30 column, programmed at 200° C isothermal; 40 ml/minute) is set forth in FIG. 31. NMR, IR and Mass Spectral analyses confirm that the 3 compounds produced have the following structures:

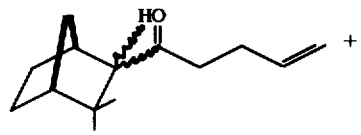

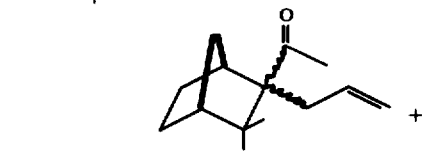

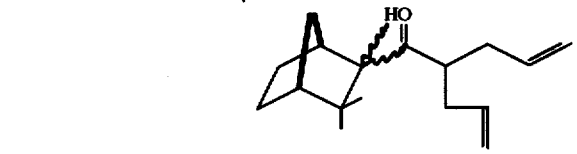

The compound having the structure:

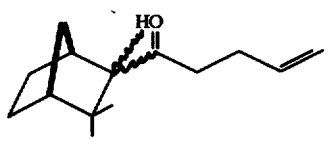

has the following mass spectral data:
m/e= 123, 81, 67, 55, 151, 108, 83; parent peak=206

The NMR data for this compound is as follows:

| δ, ppm | Interpretaton |
|---|---|
| 0.88 singlet | gem dimethyl group |
| 1.22 singlet | |
| 4.92 | |
| 5.05 | —CH=CH₂ |
| 5.12 | |
| 5.65 - 5.95 | —CH₂—CH=CH₂ |

The NMR spectrum is set forth in FIG. 32.
The compound having the structure:

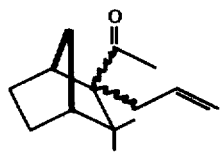

has the following MNR analysis:

| δ, ppm | Interpretation |
|---|---|
| 1.04 singlet | gem dimethyl group |
| 1.02 singlet | |
| 2.05 singlet | O‖ ⟋⟍CH₃ |
| 2.40 J = 7Hz doublet | —CH₂—CH=CH₂ |
| 4.92 multiplet | —CH=CH₂ |
| 5.96 multiplet | |
| 5.3–5.8 multiplet | —CH₂—CH=CH₂ |

The NMR spectrum for this compound is set forth in FIG. 33.
The compound having the structure:

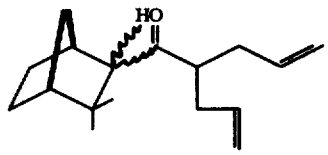

has the following NMR data:

| δ, ppm | Interpretation |
|---|---|
| 0.88 singlet | gem dimethyl group |
| 1.20 singlet | |
| 4.92–5.14 multiplet | —CH=CH₂ |
| 5.5–5.9 multiplet | —CH=CH₂ |

The NMR spectrum is set forth in FIG. 34. The Infrared spectrum is set forth in FIG. 35. The Infrared data is as follows:
1700 cm⁻¹ (C=O); 1635 cm⁻¹ (C=C)

From a perfumery standpoint, the product has a camphoraceous, woody, fruity (orange) aroma with green and piney undertones.

A process similar to that carried out above is carried out with the exception that instead of sodium hydride, a molar equivalent of sodium hydroxide is used. The results are that the same three compounds are produced in the following percentages and in the following ratios:

| Structure | Percent | Ratio |
|---|---|---|
| [norbornyl ketone with pentenyl chain] | 24 | 1.3 |
| [norbornyl ketone with methyl-allyl branch] | 19 | 1 |
| [norbornyl ketone with branched pentenyl] | 57 | 3 |

EXAMPLE XXV

PRODUCTION OF 2-(4'-PENTENOYL)-3,3-DIMETHYLNORBORNANE

Part A Reaction:

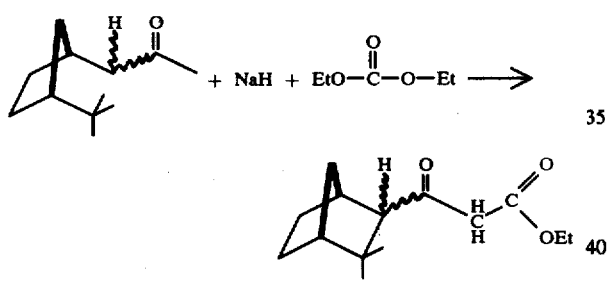

Part B Reaction:

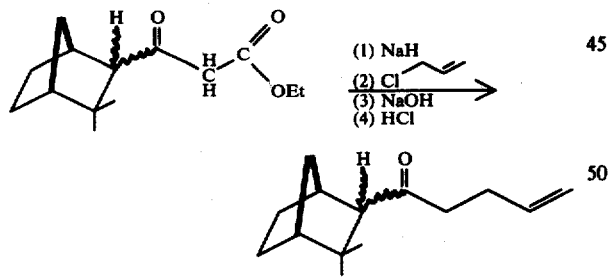

Part B Reaction:

| sodium hydride (55%) | 88 g |
|---|---|
| diethyl carbonate | 236 g |
| benzene | 1 liter |

Part A

Into a 3 liter reaction flask equipped with a nitrogen inlet tube, thermometer, reflux condenser and stirrer the following materials are placed:
sodium hydride (55%): 88 g
diethyl carbonate: 236 g
benzene: 1 liter
Under a nitrogen blanket the resulting mixture is heated to reflux.

Over a period of 30 minutes, 2-acetyl-3,3-dimethyl-norbornane is added to the reaction mass. At the end of the addition, the reaction mass is refluxed for an additional 40 minutes. Two hundred milliliters of acetic acid followed by 1 liter of water are added to the reaction mass. The organic phase is separated, and the resulting crude material is distilled rapidly using a 2 inch splash column to give 205 g of oil, b.p. 80°-160° C at 1 mm Hg.

After 5 g of Primol ® is added to the distilled material, it is fractionally distilled on a 12 inches × 1 inch Goodloe distillation column to give 119 g of product, b.p. 109°-127° C at 1.2 mm Hg.

The distilled material is confirmed by NMR analysis to have the structure:

[structure of norbornane with H, O, HCH, C(=O)OEt side chain]

NMR Data:

| δ, ppm | Interpretation |
|---|---|
| 0.92 singlet | gem dimethyl group |
| 1.22 singlet | |
| 1.24 (J=7Hz) triplet | —CH$_2$CH$_3$ |
| 3.35 singlet | $\overset{O}{\underset{\|\|}{C}}$—CH$_2$—COOEt |
| 4.18 (J=7Hz) quartet | —OCH$_2$CH$_3$ |

The NMR spectrum is set forth in FIG. 36. The Infrared spectrum is set forth in FIG. 37.

Infrared Data:
1650 —C═C (m)
1700 C═O (strong)
1780 O
       ‖
       C—OEt (strong)

Mass Spectral Data:
m/e= 108, 123, 109, 107, 29, 41; parent peak=238

Part B

One hundred grams of toluene are admixed with 24 g (0.55 moles) of sodium hydride and heated to 60° C in a 500 cc reaction flask equipped with a stirrer, thermometer and reflux condenser. Over a period of 80 minutes the carboethoxy compound produced in Part A is added to the toluene/sodium hydride mixture. At the end of the addition of the ketocarboxylic acid ester compound, a mixture of 38.5 g of alllkyl chloride and 7 g of tricapryl methyl ammonium chloride (Aliquat 336 ®, produced by General Mills Chemical Inc.) is added over a 20 minute period while maintaining the reaction mass at 80° C.

Fifty milliliters of 50% sodium hydroxide solution and 50 ml of water is then added to the reaction mass, and the resulting mixture is refluxed for a period of 2 hours. Water (100 ml) is then added to dissolved the resulting precipitate. Then 110 ml of 20% hydrochloric acid is added with the evolution of carbon dioxide gas.

The resulting product is then distilled rapidly at 100° C and 2 mm Hg pressure, and the distilled product (after adding thereto 10 g of Primol ® and 1 g of Ionox ®) is fractionated to give an oil, b.p. 90° C/1.0 mm Hg.

The product is confirmed by NMR and Infrared analyses to have the structure:

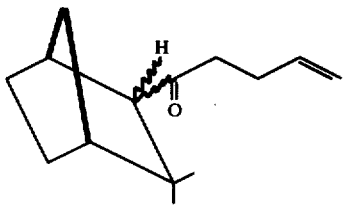

The NMR spectrum is set forth in FIG. 38.

NMR Data:

| δ, ppm | Interpretation |
|---|---|
| 0.88 singlet | |
| 1.22 singlet | gem dimethyl group |
| 4.92–5.12 multiplet | —CH=CH$_2$ |
| 5.65–5.95 multiplet | —CH$_2$—CH=CH$_2$ |

The Infrared spectrum is set forth in FIG. 39.
Infrared Data:
  1630 (C=C), 1700 cm$^{-1}$ (C=O)

EXAMPLE XXVI

PREPARATION OF 2-PENTANOYL-3,3-DIMETHYLNORBORNANE

Reaction:

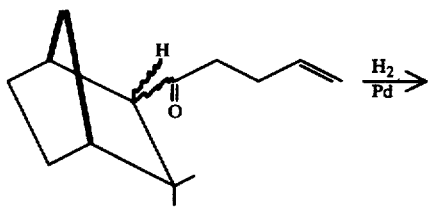

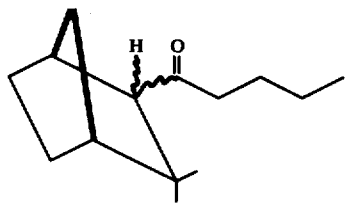

10 g of 2-(4'-pentenoyl)-3,3-dimethylnorbornane produced according to Part B of Example XXV and 50 ml of isopropyl alcohol is placed in a Parr shaker along with 0.5 g of palladium catalyst. The Parr shaker is sealed and pressurized with hydrogen up to 30 psig and over a 2 hour period is repressurized with hydrogen as needed to maintain the pressure at 30 psig. During this period of time the temperature of the reaction mass remains at 25° C. At the end of the 2 hour period the mass is filtered. The solvent is then evaporated and the product is isolated using preparative GLC.

NMR, Mass Spectral and Infrared analyses confirm that the resulting product has the structure:

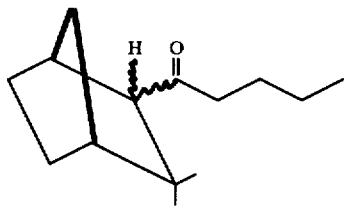

This material has a sweet, berry, mandarin orange aroma with piney nuances.

NMR Data:

| δ, ppm | Interpretation |
|---|---|
| 1.86 singlet | |
| 2.24 singlet | gem dimethyl group |
| 0.88 (J≈6Hz) triplet | —CH$_2$CH$_3$ |
| 2.30 (J≈7Hz) triplet | $\overset{O}{\underset{\|}{C}}$CH$_2$CH$_2$CH$_3$ |
| 2.30 singlet | 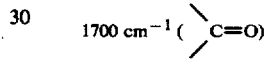 |

Mass Spectral Data:
  m/e = 123, 41, 67, 81, 57, 108, parent peak = 208
Infrared Datum:

1700 cm$^{-1}$ ( \C=O/ )

The NMR spectrum is set forth in FIG. 40. The Infrared spectrum is set forth in FIG. 41.

EXAMPLE XXVII

PREPARATION OF ALPHA-METHALLYL-ALPHA, 3,3-TRIMETHYL-5-NORBORNENE-2-METHANOL

Reaction:

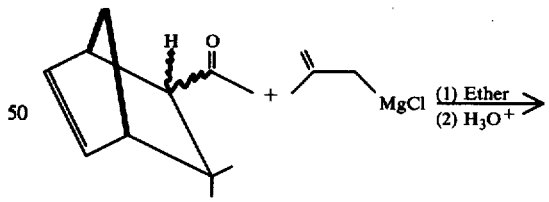

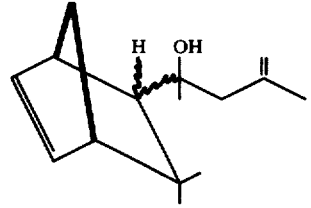

Into a 1 liter reaction flask equipped with a reflux condensor, thermometer, stirrer, dropping funnel and nitrogen inlet tube are placed 12 g (0.5 moles) of magnesium turnings and 250 cc anhydrous diethyl ether. Over a 2 hour period, 45.3 g (0.5 moles) of methallyl chloride is added. The Grignard solution is stirred for ½ hour and 28 g of 2-acetyl-3,3-dimethyl-5-norbornene is added over a 20 minute period. The mixture is stirred at reflux for ¼ hour and then is hydrolyzed by the addition of saturated ammonium chloride solution. The organic layer is washed with water and dried over magnesium sulfate. The mixture is then filtered and the solvent evaporated to yield 40 g of an oil, which is then fractionated on a micro Vigreux column after adding thereto 5 g Primol ® and a trace quantity of Ionox ®.

Mass Spectral, Infrared and NMR analyses confirm that the resulting compound has the structure:

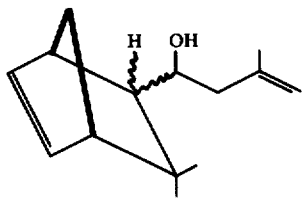

NMR Data:

| δ, ppm | Interpretation |
|---|---|
| 1.40–0.97 | methyl protons |
| 1.86 | =C—CH$_3$ |
| 2.36–1.48 | methylene and methine protons |
| 4.48–4.78 | $\underset{\mid}{-\text{C}}=\text{CH}_2$ |
| 6.24–1.12 | olefinic protons of norbornene ring |

Infrared Data:
700, 880, 1080, 1320, 1360, 1450, 2950, 3500 cm$^{-1}$.

The NMR spectrum is set forth in FIG. 42. The Infrared spectrum is set forth in FIG. 43.

EXAMPLE XXVIII

PREPARATION OF ALPHA-ALLYL-ALPHA,3,3-TRIMETHYL-2-NORBORNANEMETHANOL

Reaction:

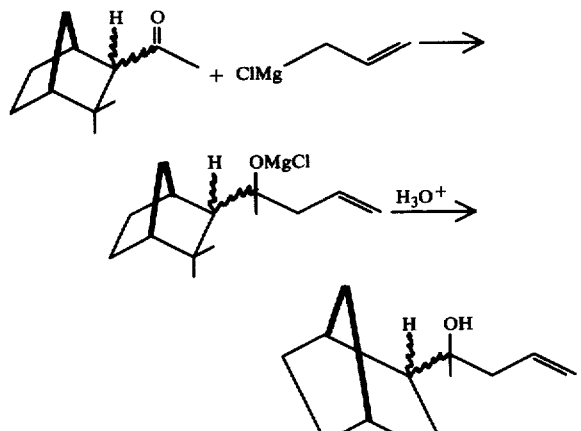

| Ingredient | Quantity |
|---|---|
| 2-acetyl-3,3-dimethyl-norbornane | 28.5 g (0.17 moles) |
| magnesium | 12.0 g (0.5 moles) |
| allyl chloride | 38.25 g (0.5 moles) |
| anhydrous ether | 200 cc |

The magnesium turnings are placed into a 1 liter, 3 neck reaction flask, followed by 200 cc of anhydrous ether. Approximately 6 cc of allyl chloride is added to initiate formation of the Grignard reagent. When the reaction is initiated, the remaining allyl chloride is added dropwise over a 2 hour period, with moderate reflux. After the addition, reflux is continued for 1 hour; at which time 28.5 g 2-acetyl-3,3-dimethylnorborane is introduced over a 20 minuted period. The reaction is very exothermic during this addition. At the end of the addition, refluxing is continued for 1 hour. The work up is carried out by hydrolyzing with NH$_4$Cl solution, filtering and separating the layers. The organic layer is washed with two 200 cc portions of water, dried over MgSO$_4$, filtered and concentrated to give 34 grams of oil which is distilled to give 26 g of product, b.p. 90–105° C at 1-2 mm Hg.

NMR Data:

| δ, ppm | Assignment |
|---|---|
| 1.06 | |
| 1.10 | |
| 1.20 | |
| 1.24 | methyl protons |
| 1.26 | |
| 1.30 | |
| 2.18–1.56 | methylene protons |
| 2.32 | |
| 5.16–5.00 | $\underset{\mid}{\text{H}}$<br>—C=CH$_2$ |
| 6.08–5.64 | HC=CH$_2$ |

Infrared Data:
910, 1085, 1160, 1200, 1250, 1300, 1330, 1360, 1385, 1460, 2860, 2940, 3070, 3480 cm$^{-1}$.

The NMR spectrum is set forth in FIG. 44. The Infrared spectrum is set forth in FIG. 45.

EXAMPLE XXIX

PREPARATION OF ALPHA-ALLYL-ALPHA,3,3-TRIMETHYL-5-NORBORNENE-2-METHANOL

Reaction:

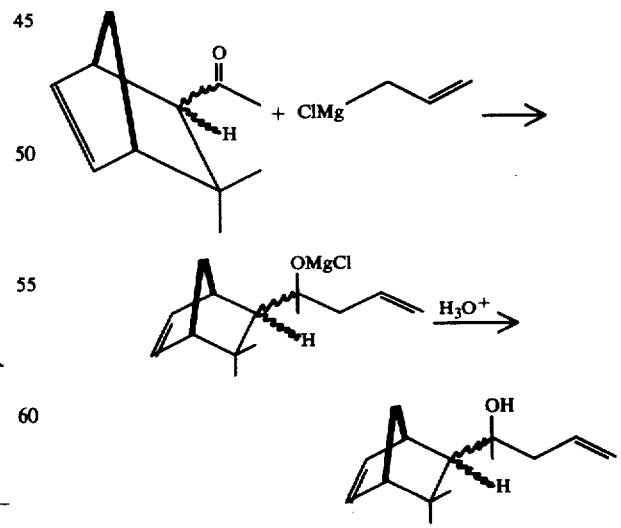

Into a 1 liter 3 necked reaction flask equipped with a stirrer, thermometer, condenser, drying tube and nitrogen inlet are placed the following materials:

| Ingredients | Quantity |
|---|---|
| 2-acetyl-3,3-dimethyl-5-norbornene | 29.2 g (0.17 moles) |
| magnesium | 12.0 g (0.5 moles) |
| allyl chloride | 38.25 g (0.5 moles) |
| anhydrous ether | 200 cc |

This reaction is carried out under the same conditions as the reaction of Example XXVIII. The work up is carried out by hydrolyzing with NH$_4$Cl solution, filtering and separating the layers. The organic layer is washed with two 200 cc portions of water, dried over MgSO$_4$, filtered and concentrated to give 37.0 grams of crude product. The crude product is distilled on a micro Vigreux column after adding thereto 5 grams of Primol ® and a trace quantity of Ionoz ® to give 23 g of oil, b.p. 90°–98° C at 1.0-1.16 mm Hg.

| NMR Data: | |
|---|---|
| δ, ppm | Interpretation |
| 1.38–0.94 | methyl protons |
| 2.40–1.50 | methylene and methine protons |
| 5.20–5.00 | HC=CH$_2$ |
| 6.02–5.66 | HC=CH$_2$ |
| 6.28–6.04 | norbornene olefinic protons |

Infrared Data:
710, 910, 995, 1085, 1140, 1250, 1325, 1360, 1460, 1635, 2960, 3060, 3470 cm$^{-1}$.

The NMR spectrum is set forth in FIG. 46. The Infrared spectrum is set forth in FIG. 47.

EXAMPLE XXX
PREPARATION OF ALPHA-METHALLYL-ALPHA,3,3-TRIMETHYL-2-NORBORANEMETHANOL

Reaction:

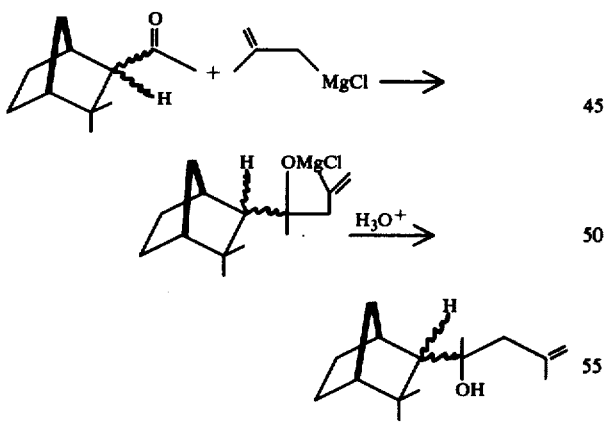

Into a 1 liter 3 necked flask equipped with a stirrer, thermometer, condenser, drying tube and nitrogen inlet are placed the following materials:

| Ingredients | Quantity |
|---|---|
| 2-acetyl-3,3-dimethyl-norbornane | 28.5 g (0.17 moles) |
| magnesium | 12.0 g (0.5 moles) |
| methallyl chloride | 45.27 g (0.5 moles) |

This reaction is carried out under the same conditions as the reaction of Example XXVIII. The work up is carried out by hydrolyzing with NH$_4$Cl solution, filtering and separating the layers. After stripping off the solvent, 34 grams of product remains. The resulting product is then distilled on a micro Vigreux column after adding thereto 5 grams Primol ® and a trace quantity of Ionox ®.

| NMR Data: | |
|---|---|
| δ, ppm | Interpretation |
| 1.27–1.06 | methyl protons |
| 1.86 | =C—CH$_3$ |
| 2.12–1.32 | |
| | —CH$_2$— + HC— |
| 4.74–4.94 | |
| | —C=CH$_2$ |

Infrared Data:
880, 1080, 1105, 1360, 1380, 1455, 1630, 2860, 2940, 3500 cm$^{-1}$.

The NMR spectrum is set forth in FIG. 48. The Infrared spectrum is set forth in FIG. 49.

EXAMPLE XXXI
PREPARATION OF 3,3-DIMETHYL-2-(4-METHYL-4-PENTENOYL)-NORBORNANE

Reaction:

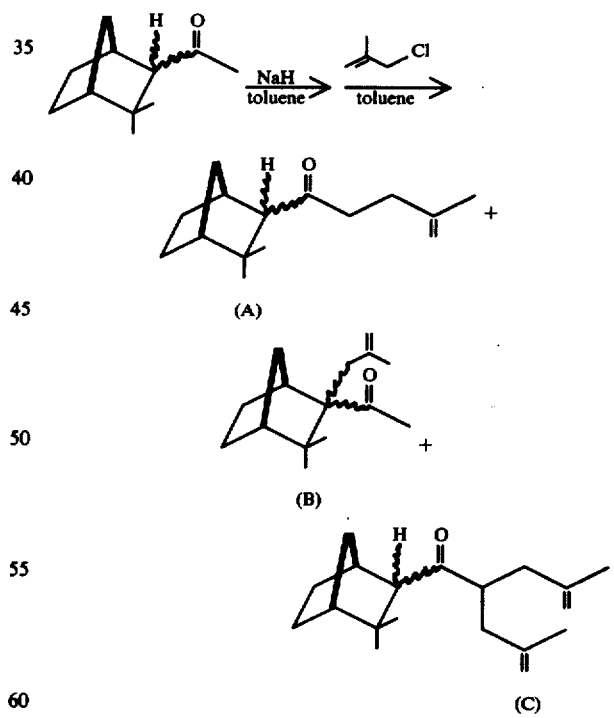

A suspension of 146 g of sodium hydride (55% mineral oil dispersion) in 1500 g of toluene is heated to 100° C and a solution of 500 g of 2-acetyl-3,3-dimethylnorbornane in 250 g of toluene is added over a period of 1 hour. The mixture is stirred at 100°–103° C until no further hydrogen gas is evolved (total gas evolved = 66 liters at 1 atmosphere).

A solution of 280 g of methallyl chloride in 250 g of toluene is then added over a period of 1 hour at 100°–105° C. The mixture is stirred at 100°–110° C for an additional 14 hours and then cooled to room temperature. The mixture is washed several times with water and the solvent is recovered at atmospheric pressure. The solvent free material is distilled rapidly through a short column under reduced pressure, and the distillate is carefully fractionated using a 12 inches × 1 inch Goodloe packed column to give (i) 214 g of an oil, b.p. 100-111° C/0.9 mm Hg, which is shown by GLC profile illustrated in FIG. 50 to be a mixture of (A) 3,3-dimethyl-2-(4'-methyl-4'-pentenoyl)-norbornane and (B) 2-acetyl-2-methallyl-3,3-dimethylnorbornane in the approximate ratio of 3:1 and (ii) 78 g of an oil, b.p. 122° C/0.8mm Hg, which was essentially pure (C) 3,3-dimethyl-2-(2'-methallyl-4'-methyl-4'-pentenoyl)-norbornane.

The NMR data for compound A are set forth below:

| δ, ppm | Interpretation | Structure |
|---|---|---|
| 4.70 | multiplet | 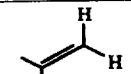 |
| 1.74 | broadened singlet | 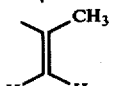 |
| 1.24 0.86 | singlet | 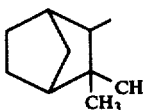 |

The Infrared datum for Compound A is set forth below: 1701 cm$^{-1}$

The NMR spectrum for this compound is set forth in FIG. 51. The Infrared spectrum for this compound is set forth in FIG. 52.

The NMR data for Compound B are set forth below:

| δ, ppm | Interpretation | Structure |
|---|---|---|
| 4.82 4.67 | broad singlet | 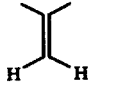 |
| 2.09 | singlet | 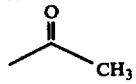 |
| 1.69 | broad singlet | 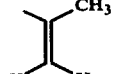 |
| 1.10 1.03 | singlet | 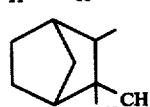 |

The infrared datum for Compound B is set forth below: 1690 cm$^{-1}$

The NMR spectrum for this compound is set forth in FIG. 53. The Infrared spectrum for this compound is set forth in FIG. 54.

The NMR analysis for Compound C are set forth below:

| δ, ppm | Interpretation | Structure |
|---|---|---|
| 4.77 | multiplet |  |
| 1.76 1.63 | 2 broad singlets |  |
| 1.22 0.87 | 2 singlets |  |

The Infrared datum for Compound C is set forth below: 1695 cm$^{-1}$

The NMR spectrum for this compound is set forth in FIG. 55. The Infrared spectrum for this compound is set forth in FIG. 56.

The mixture of compounds having the structures:

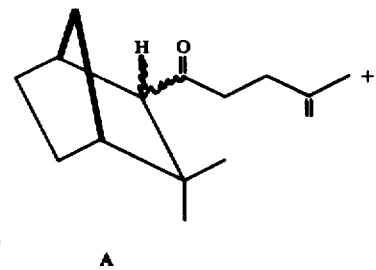

A

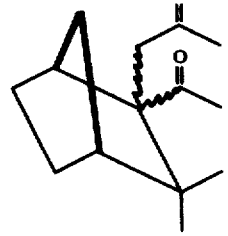

B from a flavor use standpoint, at the level of 10 ppm, has a camphoraceous, woody, minty aroma with a strong cooling nuance making it useful in dentrifices and mouthwashes. In tobacco, at the level of 200 ppm, it gives cooling and floral notes on smoking. From a perfumery use standpoint, this material has a fruity, woody note which is surprisingly long lasting.

The compound having the structure:

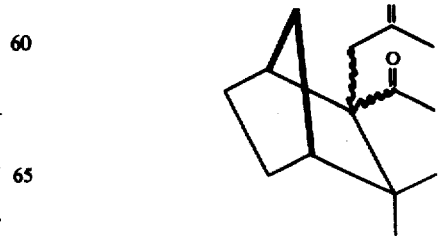

has a low-keyed, sweet, camphoraceous, cedarwoody aroma with green herbal and piney notes, from a perfumery use standpoint.

The compound having the structure:

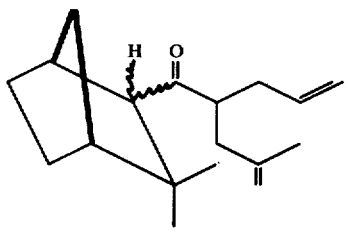

from a perfumery use standpoint, has a low-keyed, sweet, green woody, herbal aroma.

EXAMPLE XXXII

PREPARATION OF A COSMETIC POWDER COMPOSITION

A cosmetic powder is prepared by mixing in a ball mill, 100 g of talcum powder with 0.25 g of the composition prepared according to Example XV. It has an excellent pine needle aroma with green, melony, herbal, twiggy and cut wood characteristics.

EXAMPLE XXXIII

PERFUMED LIQUID DETERGENT

Concentrated liquid detergents (lysine salt of n-dodecyl benene sulfonic acid as more specifically described in U.S. Pat. No. 3,948,818, issued on Apr. 6, 1976) with intense pine needle aromas are prepared containing 0.10%, 0.15% and 0.20% of the perfume composition according to Example XV. The detergents are prepared by adding and homogeneously mixing the appropriate quantity of perfume oil composition of Example XV. The detergents all possess intense pine needle aromas, with green, melony, herbal, twiggy and cut wood characteristics, with the intensity increasing with greater concentrations of the formulations of Example XV.

EXAMPLE XXXIV

PREPARATION OF A COLOGNE AND HANDKERCHIEF PERFUME

The composition produced according to Example XV is incorporated into a cologne at a concentration of 2.5% in 85% aqueous ethanol. A distinct and definite pine needle fragrance with green, melony, herbal, twiggy and cut wood notes is imparted to the cologne. The composition of Example XV is also added to a handkerchief at a concentration of 20% (in 95% aqueous ethanol) and a distinct and definite pine needle fragrance with green, melony, herbal, twiggy and cut wood characteristics is imparted to the handkerchief perfume.

EXAMPLE XXXV

PREPARATION OF A SOAP COMPOSITION

100 Grams of soap chips are mixed with 1 gram of the perfume composition of Example XV until a substantially homogeneous composition is obtained. The perfumed soap composition manifests an excellent pine needle fragrance with green, melony, herbal, twiggy and cut wood characteristics.

EXAMPLE XXXVI

PREPARATION OF A COSMETIC POWDER COMPOSITION

A cosmetic powder is prepared by mixing in a ball mill, 100 g of talcum powder with 0.25 g of the composition prepared according to Example XII. It has an excellent pine needle aroma with sweet, woody, fruity, spicey (nutmeg, pepper), and herbaceous characteristics.

EXAMPLE XXXVII

PERFUMED LIQUID DETERGENT

Concentrated liquid detergents (lysine salt of n-dodecyl benene sulfonic acid as more specifically described in U.S. Pat. No. 3,948,818, issued on Apr. 6, 1976) with intense pine needle aromas are prepared containing 0.10%, 0.15% and 0.20% of the perfume composition produced according to Example XII. The detergents are prepared by adding and homogeneously mixing the appropriate quantity of perfume oil composition of Example XII. The detergents all possess intense pine needle aromas, with sweet, woody, fruity, spicey (nutmeg, pepper), and herbaceous characteristics, with the intensity increasing with greater concentrations of the formulations of Example XII.

EXAMPLE XXXVIII

PREPARATION OF A COLOGNE AND HANDKERCHIEF PERFUME

The composition produced according to Example XII is incorporated into a cologne at a concentration of 2.5% in 85% aqueous ethanol. A distinct and definite pine needle fragrance with sweet, woody, fruity, spicey (nutmeg, pepper), and herbaceous characteristics is imparted to the cologne. The composition of Example XII is also added to a handkerchief at a concentration of 20% (in 95% aqueous ethanol) and a distinct and definite pine needle fragrance with sweet, woody, fruity, spicey (nutmeg, pepper), and herbaceous characteristics is imparted to the handkerchief perfume.

EXAMPLE XXXIX

PREPARATION OF A SOAP COMPOSITION

100 Grams of soap chips are mixed with 1 gram of the perfume composition of Example XII until a substantially homogeneous composition is obtained. The perfumed soap composition manifests an excellent pine needle fragrance with sweet, woody, fruity, spicey (nutmeg, pepper), and herbaceous characteristics.

EXAMPLE XL

PREPARATION OF A COSMETIC POWDER COMPOSITION

A cosmetic powder is prepared by mixing in a ball mill, 100 g of talcum powder with 0.25 g of the composition prepared according to Example III. It has an excellent pine needle aroma with fruity, herbaceous, armois and fir-balsam characteristics.

EXAMPLE XLI

PERFUMED LIQUID DETERGENT

Concentrated liquid detergents (lysine salt of n-dodecyl benzene sulfonic acid as more specifically described in U.S. Pat. No. 3,948,818, issued on Apr. 6, 1976) with intense pine needle aromas are prepared containing 0.10%, 0.15% and 0.20% of the perfume composition produced according to Example III. The detergents are prepared by adding and homogeneously mixing the appropriate quantity of the perfume oil composition of Example III. The detergents all possess intense pine needle aromas, with fruity, herbaceous, armois and fir-balsam characteristics, with the intensity increasing with greater concentrations of the formulations of Example III.

EXAMPLE XLII
PREPARATION OF A COLOGNE AND HANDKERCHIEF PERFUME

The composition produced according to Example III is incorporated into a cologne at a concentration of 2.5% in 85% aqueous ethanol. A distinct and definite pine needle fragrance with fruity, herbaceous, armois and fir-balsam characteristics is imparted to the cologne. The composition of Example III is also added to a handkerchief at a concentration of 20% (in 95% aqueous ethanol) and a distinct and definite pine needle fragrance with fruity, herbaceous, armois and fir-balsam characteristics is imparted to the handkerchief perfume.

EXAMPLE XLIII
PREPARATION OF A SOAP COMPOSITION

100 Grams of soap chips are mixed with 1 gram of the perfume composition of Example III until a substantially homogeneous composition is obtained. The perfumed soap composition manifests an excellent pine needle fragrance with fruity, herbaceous, armois and fir-balsam characteristics.

EXAMPLE XLIV
PREPARATION OF A COSMETIC POWDER COMPOSITION

A cosmetic powder is prepared by mixing in a ball mill, 100 g of talcum powder with 0.25 g of the composition prepared according to Example II. It has an excellent pine needle aroma with sweet, woody, thujone-like, armoise, cedarleaf and camphoraceous characteristics.

EXAMPLE XLV
PERFUMED LIQUID DETERGENT

Concentrated liquid detergents (lysine salt of n-dodecyl benzene sulfonic acid as more specifically described in U.S. Pat. No. 3,948,818, issued on Apr. 6, 1976) with intense pine needle aromas are prepared containing 0.10%, 0.15% and 0.20% of the perfume composition produced according to Example II. The detergents are prepared by adding and homogeneously mixing the appropriate quantity of the perfume oil composition of Example II. The detergents all possess intense pine needle aromas, with sweet, woody, thujone-like, armoise, cedar-leaf and camphoraceous characteristics, with the intensity increasing with greater concentrations of the formulations of Example II.

EXAMPLE XLVI
PREPARATION OF A COLOGNE AND HANDKERCHIEF PERFUME

The composition produced according to Example II is incorporated into a cologne at a concentration of 2.5% in 85% aqueous ethanol. A distinct and definite pine needle fragrance with sweet, woody, thujone-like, armoise, cedar-leaf and camphoraceous characteristic is imparted to the cologne. The composition of Example II is also added to a handkerchief at a concentration of 20% (in 95% aqueous ethanol) and a distinct and definite pine needle fragrance with sweet, woody, thujone-like, armoise, cedar-leaf and camphoraceous characteristics is imparted to the handkerchief perfume.

EXAMPLE XLVII
PREPARATION OF A SOAP COMPOSITION

100 Grams of soap chips are mixed with 1 gram of the perfume composition of Example II until a substantially homogeneous composition is obtained. The performed soap composition manifests an excellent pine needle fragrance with sweet, woody, thujone-like, armoise, cedar-leaf and camphoraceous characteristics.

EXAMPLE XLIX
PERFUMED LIQUID DETERGENT

Concentrated liquid detergents (lysine salt of n-docedyl benzene sulfonic acid as more specifically described in U.S. Pat. No. 3,948,818, issued on Apr. 6, 1976) with intense pine needle aromas are prepared containing 0.10%, 0.15% and 0.20% of the perfume composition produced according to Example XIX. The detergents are prepared by adding and homogeneously mixing the appropriate quantity of the perfume oil composition of Example XIX. The detergents all possess intense pine needle aromas, with fruity, musty, sweet, woody, minty nuances with fresh cut pine/spruce characteristics, with the intensity increasing with greater concentrations of the formulations of Example XIX.

EXAMPLE L
PREPARATION OF A COLOGNE AND HANDKERCHIEF PERFUME

The composition produced according to Example XIX is incorporated into a cologne at a concentration of 2.5% in 85% aqueous ethanol. A distinct and definite pine needle fragrance with fruity, musty, sweet, woody, minty, fresh cut pine/spruce notes is imparted to the cologne. The composition of Example XIX is also added to a handkerchief at a concentration of 20% (in 95% aqueous ethanol) and a distinct and definite pine needle fragrance with fruity, musty, sweet, wody, minty, fresh cut pine/spruce characteristics is imparted to the handkerchief perfume.

EXAMPLE LI
PREPARATION OF A SOAP COMPOSITION

100 Grams of soap chips are mixed with 1 gram of the perfume composition of Example XIX until a substantially homogeneous composition is obtained. The perfumed soap composition manifests an excellent pine needle fragrance with fruity, musty, sweet, woody, minty and fresh cut pine/spruce characteristics.

EXAMPLE LII
PREPARATION OF A COSMETIC POWDER COMPOSITION

A cosmetic powder is prepared by mixing in a ball mill, 100 g of talcum powder with 0.25 g of the composition prepared according to Example XVII. It has an excellent pine needle aroma with musty, sweet fruity, woody and artemesia characteristics.

EXAMPLE LIII

PERFUMED LIQUID DETERGENT

Concentrated liquid detergents (lysine salt of n-dodecyl benzene sulfonic acid as more specifically described in U.S. Pat. No. 3,948,818, issued on Apr. 6, 1976) with intense pine needle aromas are prepared containing 0.10%, 0.15% and 0.20% of the perfume composition produced according to Example XVII. The detergents are prepared by adding and homogeneously mixing the appropriate quantity of the perfume oil composition of Example XVII. The detergents all possess intense pine needle aromas, with musty, sweety fruity, woody and artemesia characteristics, with the intensity increasing with greater concentrations of the formulations of Example XVII.

EXAMPLE LIV

PREPARATION OF A COLOGNE AND HANDKERCHIEF PERFUME

The composition produced according to Example XVII is incorporated into a cologne at a concentration of 2.5% in 85% aqueous ethanol. A distinct and definite pine needle fragrance with musty, sweet fruity, woody and artemesia notes is imparted to the cologne. The composition of Example XVII is also added to a handkerchief at a concentration of 20% (in 95% aqueous ethanol) and a distinct and definite pine needle fragrance with musty, sweet fruity, woody and artemesia characteristics is imparted to the handkerchief perfume.

EXAMPLE LV

PREPARATION OF A SOAP COMPOSITION

100 Grams of soap chips are mixed with 1 gram of the perfume composition of Example XVII until a substantially homogeneous composition is obtained. The perfumed soap composition manifests an excellent pine needle fragrance with musty, sweet fruity, woody and artemesia characteristics.

EXAMPLE LVI

PREPARATION OF A COSMETIC POWDER COMPOSITION

A cosmetic powder is prepared by mixing in a ball mill, 100 g of talcum powder with 0.25 g of the composition prepared according to Example XI. It has an excellent pine needle aroma with woody, piney, natural-like nuances with fruity, spicey, cresylic, borneol characteristics with a definitive berry top note.

EXAMPLE LVII

PERFUMED LIQUID DETERGENT

Concentrated liquid detergents (lysine salt of n-dodecyl benzene sulfonic acid as more specifically described in U.S. Pat. No. 3,948,818, issued on Apr. 6, 1976) with intense pine needle aromas are prepared containing 0.10%, 0.15% and 0.20% of the perfume composition produced according to Example XI. The detergents are prepared by adding and homogeneously mixing the appropriate quantity of the perfume oil composition of Example XI. The detergents all possess intense pine needle aromas, with woody, piney, natural-like nuances with fruity, spicey, cresylic, borneol characteristics with a definitive berry top note, with the intensity increasing with greater concentrations of the formulations of Example XI.

EXAMPLE LVIII

PREPARATION OF A COLOGNE AND HANDKERCHIEF PERFUME

The composition produced according to Example XI is incorporated into a cologne at a concentration of 2.5% in 85% aqueous ethanol. A distinct and definite pine needle fragrance with woody, piney, natural-like nuances with fruity, spicey, cresylic, borneol characteristics with a definitive berry top note is imparted to the cologne. The composition of Example XI is also added to a handkerchief at a concentration of 20% (in 95% aqueous ethanol) and a distinct and definite pine needle fragrance with woody, piney, natural-like nuances with fruity, spicey, cresylic, borneol characteristics with a definitive berry top note is imparted to the handkerchief perfume.

EXAMPLE LIX

PREPARATION OF A SOAP COMPOSITION

100 Grams of soap chips are mixed with 1 gram of the perfume composition of Example XI until a substantially homogenous composition is obtained. The perfumed soap composition manifests an excellent pine needle fragrance with woody, piney, natural-like nuances with fruity, spicey, cresylic, borneol characteristics with a definitive berry top note.

EXAMPLE LX

TOBACCO FILTER

Into a 20 mm cellulose acetate filter is added:
alpha-ethyl-3,3-dimethyl-2-norbornanemethanol at the rate of 1,000 ppm (10 micro liter of a 10% solution of said norbornanemethanol is added to the filter)

The filter is then attached to a full flavor cigarette on the market, e.g. (1) Marlboro ®, (2) Winston ® or (3) Viceroy ®, as well as on a Kentucky 1A3 reference cigarette (produced by the University of Kentucky), yielding the following results:

1. Both cigarettes containing said norbornanemethanol additive, when compared to a cigarette having a filter without said norbornanemethanol additive, give rise to sweet, woody, piney aromas on smoking, with a pleasant, cooling effect and rather noticeable reduced harshness.

2. Both cigarettes containing said norbornanemethanol additive have a lesser degree of "hotness" and give rise to a "fresh" taste on smoking.

(1) Registered trademark of the Phillip Morris Company.
(2) Registered trademark of the R. J. Reynolds Company.
(3) Registered trademark of the Brown & Williamson Company.

EXAMPLE LXI

SODIUM BOROHYDRIDE REDUCTION OF 2-(2-BUTENOYL)-3,3-DIMETHYLNORBORNANE

Reaction:

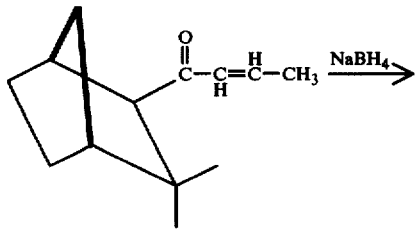

-continued

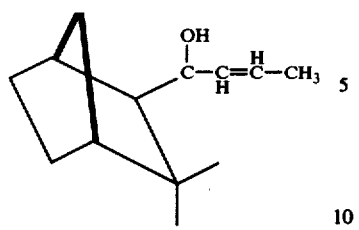

Into a 500 cc three necked reaction flask equipped with a stirrer, condenser and thermometer is placed 82 g (43 moles) of a material containing more than 90% 2-(trans-2-butenoyl)-3,3-dimethylnorbornane (produced according to Example XII) and 250 g of anhydrous methanol. Over a period of 1 hour, 7 g of sodium borohydride is added to the reaction mass, while the reaction mass remains at 25°-26° C.

The reaction mass is then stirred for a period of 3 hours at 25°-28° C, whereupon another 7 grams of sodium borohydride is added. The reaction mass is then stirred for another 3 hours until no further change in the GLC profile is observed. The resulting mixture is then transferred to a 1 liter flask, and the methanol is stripped off leaving a slurry. To the slurry is added 500 ml water, and the resulting mixture is extracted with 150 ml of cyclohexane. The cyclohexane extract is stripped and distilled rapidly at 100°-115° C and a vacuum of 2.4-2.6 mm Hg. After adding to the resulting material 5 g Primol ® and 0.1 g of Ionol ®, the rushed over material is fractionally distilled on a 8 plate Vigreaux column at 113°-120° C vapor temperature and 2.7-4.4 mm Hg pressure (reflux ratio 20:1). Ten fractions are produced of which fractions 2-8 are used for flavor and perfumery work.

The resulting material is primarily a mixture of three compounds having the structures:

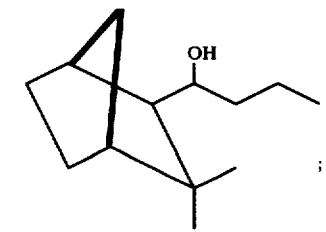

;

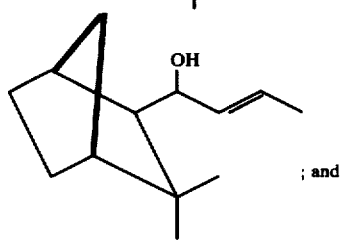

; and

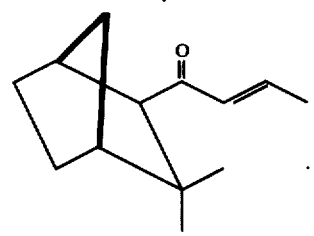

as confirmed by NMR, IR and Mass Spectral analyses.

The resulting mixture is evaluated at 10% in food grade ethanol, from a perfumery standpoint, and has sweet piney, bornyl acetate-like, berry and somewhat woody notes.

From a flavor standpoint, it has a spicey, valerian oil-like, calamus-like, pine needle-like, herbaceous and fruity aroma character with a valerian oil-like, calamus, pine needle, herbaceous and fruity flavor character at 1 ppm.

The resulting mixture has uses in spice flavors, cordial flavors, pine needle flavors and root beer flavors.

Figure 57:
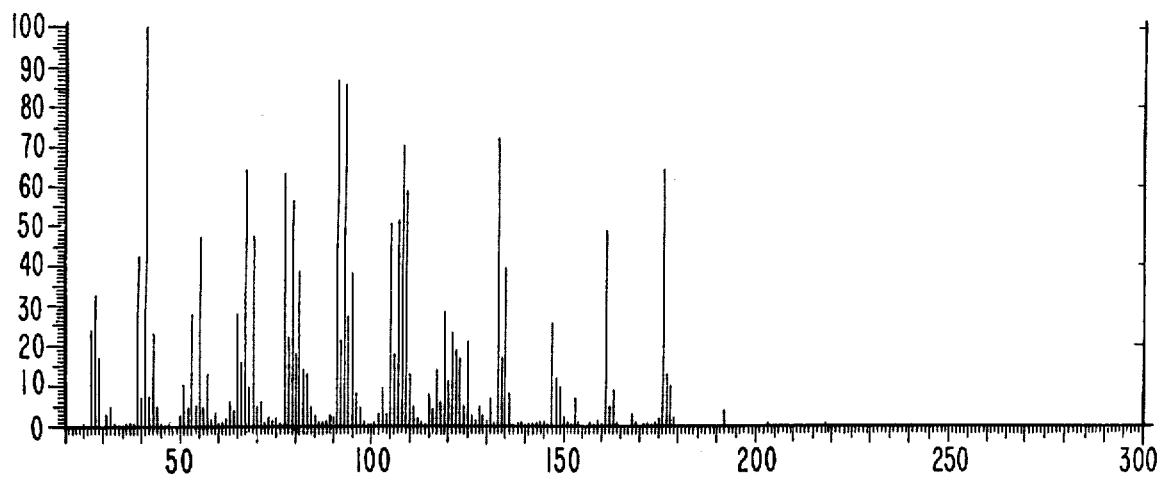

The GC-MS profile for the compound having the structure:

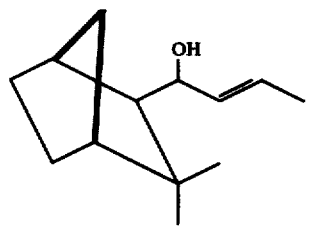

is set forth in FIG. 57.

Figure 58:
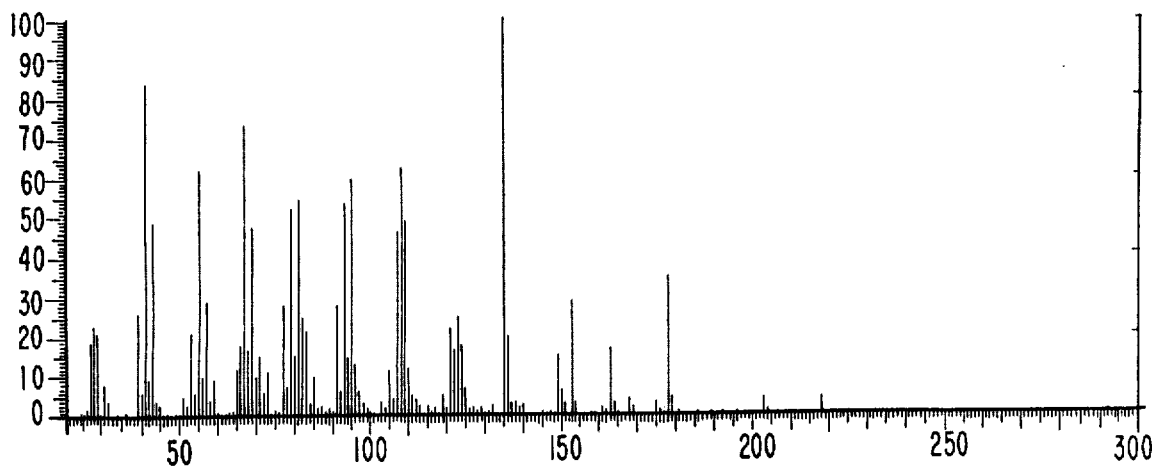

The GC-MS profile for the compound having the structure:

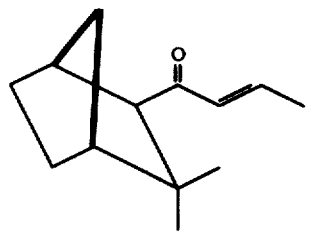

is set forth in FIG. 58.

Figure 59:
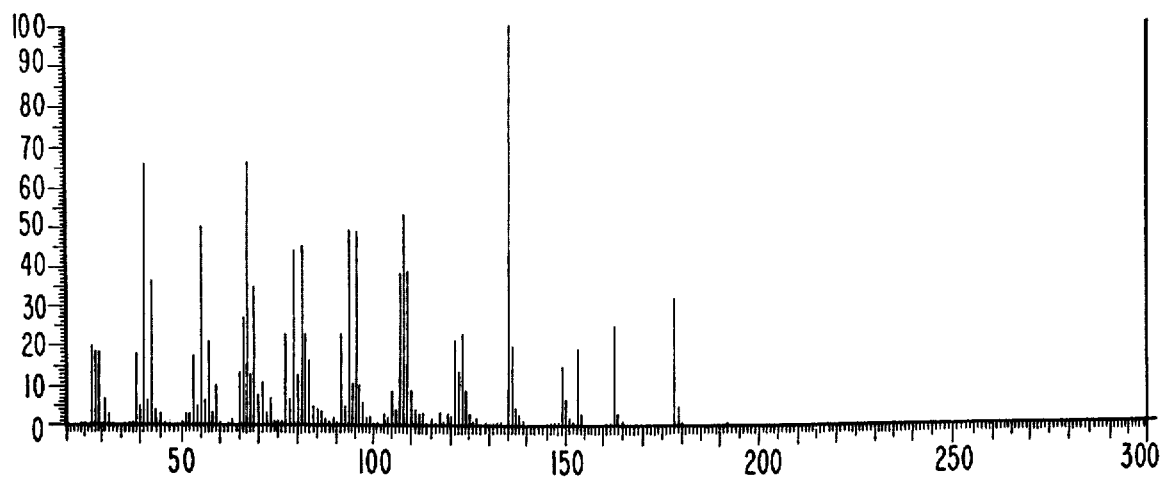

The GC-MS profile for the compound having the structure:

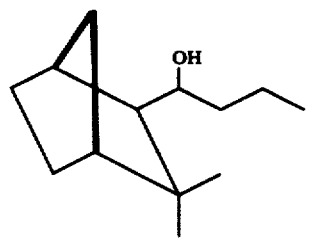

is set forth in FIG. 59.

Figure 60:
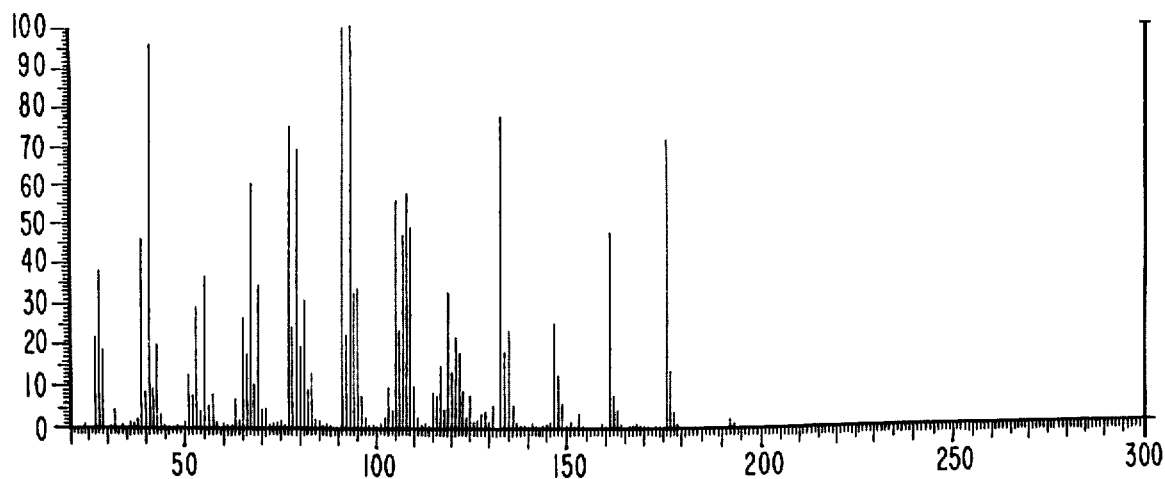

The GC-MS profile for the mixture of remaining compounds in the reaction product is set forth in FIG. 60.

What is claimed is:

1. A process for augmenting or enhancing the aroma of a liquid detergent comprising the step of intimately admixing with said detergent a norbornane derivative either (i) having a structure selected from the group consisting of:

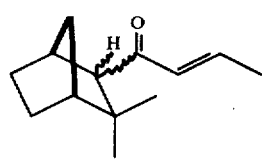

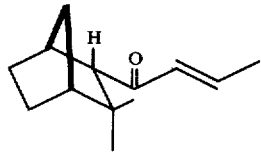

and

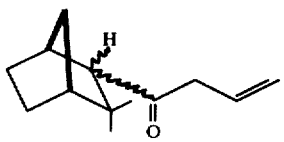

and

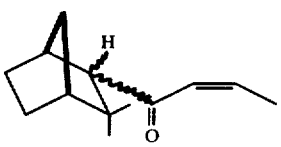

and mixtures of same or (ii) a mixture of 2-(2-butenoyl)-3,3-dimethylnorbornane; 2-(3-butenoyl)-3,3-dimethylnorbornane; 2-(2-butenoyl)-3,3-dimethylnorbornane and alpha-allyl-3,3-dimethyl-norbornanemethanol until a substantially homogenous composition is obtained, said norbornane derivative or said mixture being present in said liquid detergent in an amount of from 1% up to 3% by weight.

2. The process of claim 1 wherein the norbornane derivative has the structure:

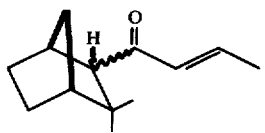

3. The process of claim 1 wherein the norbornane derivative has the structure:

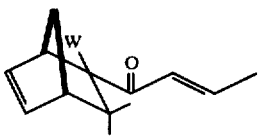

4. The process of claim 1 wherein the norbornane derivative has the structure:

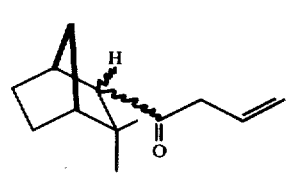

5. The process of claim 1 wherein the norbornane derivative has the structure:

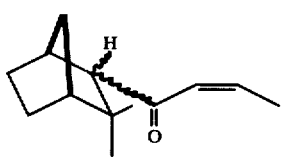

6. The process of claim 1 wherein the substance added to the liquid detergent is a mixture of 2-(2-butenoyl)-3,3-dimethylnorbornane; 2-(3-butenoyl)-3,3-dimethylnorbornane; 2-(2-butenoyl)-3,3-dimethylnorbornane and α-allyl-3,3-dimethyl-2-norbornanemethanol.

* * * * *